United States Patent
Ding et al.

(10) Patent No.: US 9,872,866 B2
(45) Date of Patent: Jan. 23, 2018

(54) VITAMIN D RECEPTOR/SMAD GENOMIC CIRCUIT GATES FIBROTIC RESPONSE

(71) Applicants: Salk Institute for Biological Studies, La Jolla, CA (US); The University of Sydney, Darlington, NSW (AU)

(72) Inventors: Ning Ding, Riverside, CA (US); Michael Downes, San Diego, CA (US); Christopher Liddle, Chertswood (AU); Ronald M. Evans, La Jolla, CA (US)

(73) Assignees: Salk Institute for Biological Studies, San Diego, CA (US); The University of Sydney, Sydney (AU)

( * ) Notice: Subject to any disclaimer, the term of this patent is extended or adjusted under 35 U.S.C. 154(b) by 0 days.

(21) Appl. No.: 14/921,230

(22) Filed: Oct. 23, 2015

(65) Prior Publication Data

US 2016/0106762 A1    Apr. 21, 2016

Related U.S. Application Data

(63) Continuation of application No. PCT/US2014/035235, filed on Apr. 24, 2014.

(60) Provisional application No. 61/815,575, filed on Apr. 24, 2013.

(51) Int. Cl.

| A61K 31/592 | (2006.01) |
|---|---|
| A61K 31/07 | (2006.01) |
| A61K 31/59 | (2006.01) |
| A61K 31/593 | (2006.01) |
| A61K 45/06 | (2006.01) |
| A61K 31/7068 | (2006.01) |
| G01N 33/50 | (2006.01) |
| G01N 33/82 | (2006.01) |
| A61K 9/16 | (2006.01) |
| A61K 47/54 | (2017.01) |
| A61K 47/62 | (2017.01) |
| A61K 47/69 | (2017.01) |

(52) U.S. Cl.
CPC ............ *A61K 31/592* (2013.01); *A61K 9/167* (2013.01); *A61K 31/07* (2013.01); *A61K 31/59* (2013.01); *A61K 31/593* (2013.01); *A61K 31/7068* (2013.01); *A61K 45/06* (2013.01); *A61K 47/542* (2017.08); *A61K 47/62* (2017.08); *A61K 47/6929* (2017.08); *A61K 47/6931* (2017.08); *G01N 33/5058* (2013.01); *G01N 33/82* (2013.01); *G01N 2500/10* (2013.01); *G01N 2800/085* (2013.01)

(58) Field of Classification Search
None
See application file for complete search history.

(56) References Cited

U.S. PATENT DOCUMENTS

| 6,358,939 B1 | 3/2002 | Hayes et al. |
| 8,318,708 B2 | 11/2012 | Evans et al. |
| 2005/0009793 A1 | 1/2005 | Curd |
| 2005/0124591 A1 | 6/2005 | Tian et al. |
| 2005/0148557 A1 | 7/2005 | Tian et al. |
| 2006/0074109 A1 | 4/2006 | Polvino et al. |
| 2006/0135610 A1 | 6/2006 | Bortz et al. |
| 2006/0178351 A1 | 8/2006 | Curd et al. |
| 2006/0240150 A1 | 10/2006 | Delaney et al. |
| 2007/0197517 A1* | 8/2007 | Jani ............... A61K 31/282 514/229.5 |
| 2007/0275934 A1* | 11/2007 | Curd ............... A61K 31/59 514/167 |
| 2009/0209500 A1 | 8/2009 | Evans et al. |
| 2010/0099640 A1 | 4/2010 | Geuns et al. |
| 2011/0014126 A1 | 1/2011 | Evans et al. |

FOREIGN PATENT DOCUMENTS

| CN | 102 342 914 A | 2/2012 |
| JP | 2013-56834 A | 3/2013 |
| WO | WO 2008/024485 A2 | 2/2008 |
| WO | WO 2008/057363 A2 | 5/2008 |
| WO | WO-2009/061961 A1 | 5/2009 |
| WO | WO 2010/143986 A1 | 12/2010 |
| WO | WO 2011/143209 A1 | 11/2011 |
| WO | WO 2012/127037 A2 | 9/2012 |

OTHER PUBLICATIONS

Demetter et al., "Molecular Changes in Pancreatic Cancer: Implications for Molecular Targeting Therapy," *Acta Gastro-Enterological Belgica* 75:210-214, 2012.
Fearon, "The Carcinoma-Associated Fibroblast Expressing Fibroblast Activation Protein and Escape from Immune Surveillance," *Cancer Immunol Res.* 2:187-193, 2014.
Feig et al., "Targeting CXCL12 from FAP-Expressing Carcinoma-Associated Fibroblasts Synergizes with Anti-PD-L1 Immunotherapy in Pancreatic Cancer," *Proc Natl Acad Sci. USA* 110:20212-20217, 2013.
International Search Report and Written Opinion of the International Searching Authority issued by Australian Patent Office dated Sep. 5, 2014 for PCT/US2014/041063.
Johnson et al., "The Antitumor Efficacy of Calcitriol: Preclinical Studies," *Anticancer Res.* 26:2543-2500, 2006.
Wehr et al., "Analysis of the Human Pancreatic Stellate Cell Secreted Proteome," *Pancreas* 40:557-566, 2011.
Abramovitch et al., "Vitamin D inhibits proliferation and profibrotic marker expression in hepatic stellate cells and decreases thioacetamide-induced liver fibrosis in rats," *Gut*, 60:1728-1737, 2011.
Cao et al., "Leptin Stimulates Tissue Inhibitor of Metalloproteinase-1 in Human Hepatic Stellate Cells," *J. Biol. Chem.*, vol. 279, pp. 4292-4304, 2004.
Cohen-Lahav et al., "The Anti-Inflammatory Activity of 1,25-Dihydroxyvitamin D3 in Macrophages," *J. Steroid. Biochem. Mol. Biol.*, vol. 103, pp. 558-562, 2007.

(Continued)

*Primary Examiner* — Jennifer A Berrios
(74) *Attorney, Agent, or Firm* — Klarquist Sparkman, LLP

(57) ABSTRACT

The present disclosure provides compositions that include a nanoparticle and a compound that increases the biological activity of the vitamin D receptor (VDR) (e.g., a VDR agonist), and methods of using such compounds to increase retention or storage of vitamin A, vitamin D, and/or lipids by a cell, such as an epithelial or stellate cell. Such methods can be used to treat or prevent fibrosis.

5 Claims, 15 Drawing Sheets

(56) References Cited

OTHER PUBLICATIONS

Dai et al., "PPAR gamma is an important transcription factor in 1 alpha, 25-dihydroxyvitaim D3-induced involucrin expression," *J. Derm. Sci*, vol. 51, No. 1, pp. 53-60, Apr. 2008.

Ding et al., "A vitamin D receptor/SMAD genomic circuit gates hepatic fibrotic response," *Cell*, vol. 153, No. 3, pp. 601-613, Apr. 25, 2013.

Dunlop et al., "The human peroxisome proliferator-activated receptor δ gene is a primary target of $1\alpha,25$-dihydroxyvitamin $D_3$ and it nuclear receptor," *J. Mol. Biol.*, vol. 349, No. 2, pp. 248-260, Jun. 2005.

Gascon-Barré et al., "The Normal Liver Harbors the Vitamin D Nuclear Receptor in Nonparenchymal and Biliary Epithelial Cells," *Hepatology*, 37:1034-1042, 2003.

International Search Report and Written Opinion of the International Searching Authority issued by Australian Patent Office dated Sep. 17, 2014 for PCT/US2014/035235.

Johnson et al., "The Activated Mesangial Cell: A Glomerular 'Myofibroblast'?," *J. Am. Soc. Nephrol.*, vol. 2, pp. S190-S197, 1992.

Jonas et al., "Measurement of Parenchymal Function and Bile Duct Flow in Primary Sclerosing Cholangitis Using Dynamic $^{99m}$Tc-HIDA SPECT," *J. Gastroenterol. Hepatol.* vol. 21, pp. 674-681, 2006.

Klöppel et al., "Fibrosis of the pancreas: the initial tissue damage and the resulting pattern," *Virchows Arch*, vol. 445, pp. 1-8, May 2004.

Ma et al., "$1.25D_3$ enhances antitumor activity of gemcitabine and cisplatin in human bladder cancel models," *Cancer*, 116:3294-3303, Jul. 1, 2010.

Omary et al., "The Pancreatic Stellate Cell: A Star on the Rise in Pancreatic Diseases," *J. Clin. Invest.* vol. 117, pp. 50-59, 2007.

Petta et al., "Low Vitamin D Serum Level Is Related to Severe Fibrosis and Low Responsiveness to Interferon-Based Therapy in Genotype 1 Chronic Hepatitis C," *Hepatology*, vol. 51, pp. 1158-1167, 2010.

Samer et al., "Rat Primary and Immortalized Human Hepatocytes Express an Inducible and Functional Vitamin D Receptor," Abstract, Hepatology & Luminal Research Workshop & Clinical Update on Non-Invasive Markers of Liver Injury and Early Diagnosis of Liver Disease, 1-3, Yarra Valley, Victoria, Australia, May 2009.

Suda et al., "Pancreatic fibrosis in patients with chronic alcohol abuse: correlation with alcoholic pancreatitis," *Am J Gastroenterol*, 89:2060-2062, Nov. 1994.

Tan et al., "Paricalcitol Attenuates Renal Interstitial Fibrosis in Obstructive Nephropathy," *J. Am. Soc. Nephrol*, vol. 17, pp. 3382-3393, 2006.

Tan et al., "Therapeutic Role and Potential Mechanisms of Active Vitamin D in Renal Interstitial Fibrosis," *J. Steroid. Biochem. Mol. Biol.*, 103:491-496, 2007.

Whitcomb, "Genetic aspects of pancreatitis," *Annual Review of Medicine*, vol. 61, pp. 413-424, Palo Alto, 2010.

Zehnder et al., "Expression of 25-Hydroxyvitamin D3-1alpha-hydroxylase in the Human Kidney," *J. Am. Soc. Nephrol.*, vol. 10, pp. 2465-2473, 1999.

Zollner et al., "Role of Nuclear Receptors in the Adaptive Response to Bile Acids and Cholestasis: Pathogenetic and Therapeutic Considerations," *Mol. Pharm.*, vol. 3, pp. 231-251, 2006.

Mahadevan & Hoff, "Tumor-stroma interactions in pancreatic ductual adenocarcinoma," *Mol Cancer Ther*. 6:1186-1197, 2007.

Li et al., "Mannose 6-Phosphate-Modified Bovine Serum Albumin Nanoparticles for Controlled and Targeted Delivery of Sodium Ferulate for Treatment of Heptatic Fibrosis," *J Pharm Pharmacol*. 61:1155-1161, 2009.

Zhang et al., "Interactions of Nanomaterials and Biological Systems: Implications to Personalized Nanomedicine," *Adv Drug Deilv*. 64:1363-1384, 2012.

EP14787709.6 Communication Pursuant to Rule 164(1) EPC dated Sep. 13, 2016 with Supplementary Partial European Search Report dated Aug. 19, 2016 (9 pages).

Milczarek et al., "Vitamin D Analogs Enhance the Anticancer Activity of 5-Fluorouracil in an in vivo Mouse Colon Cancer Model," *BMC Cancer* 13:294 (2013).

EP14806812.5 Rule 164(1) EPC Communication dated Nov. 3, 2016 with Supplementary Partial European Search Report dated Oct. 25, 2016 (11 pages).

* cited by examiner

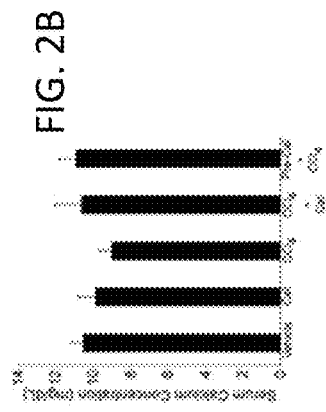
FIG. 2A
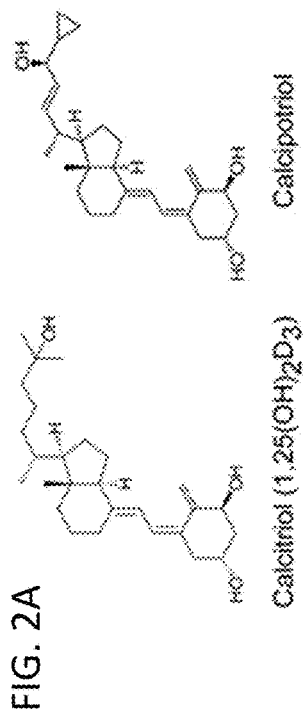
FIG. 2B
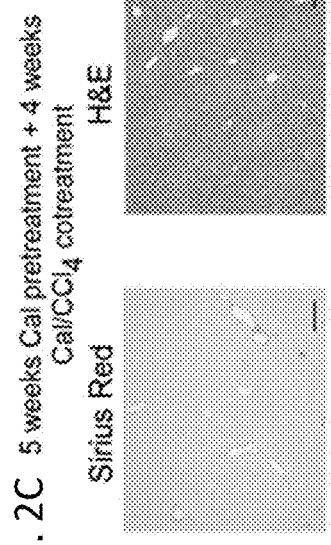
FIG. 2C 5 weeks Cal pretreatment + 4 weeks Cal/CCl$_4$ cotreatment
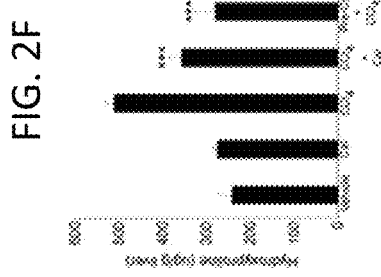
FIG. 2D
FIG. 2E
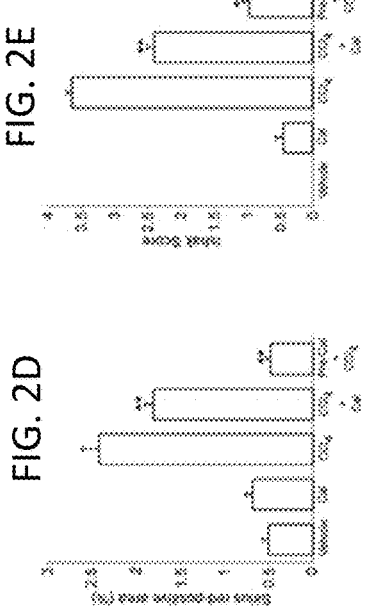
FIG. 2F

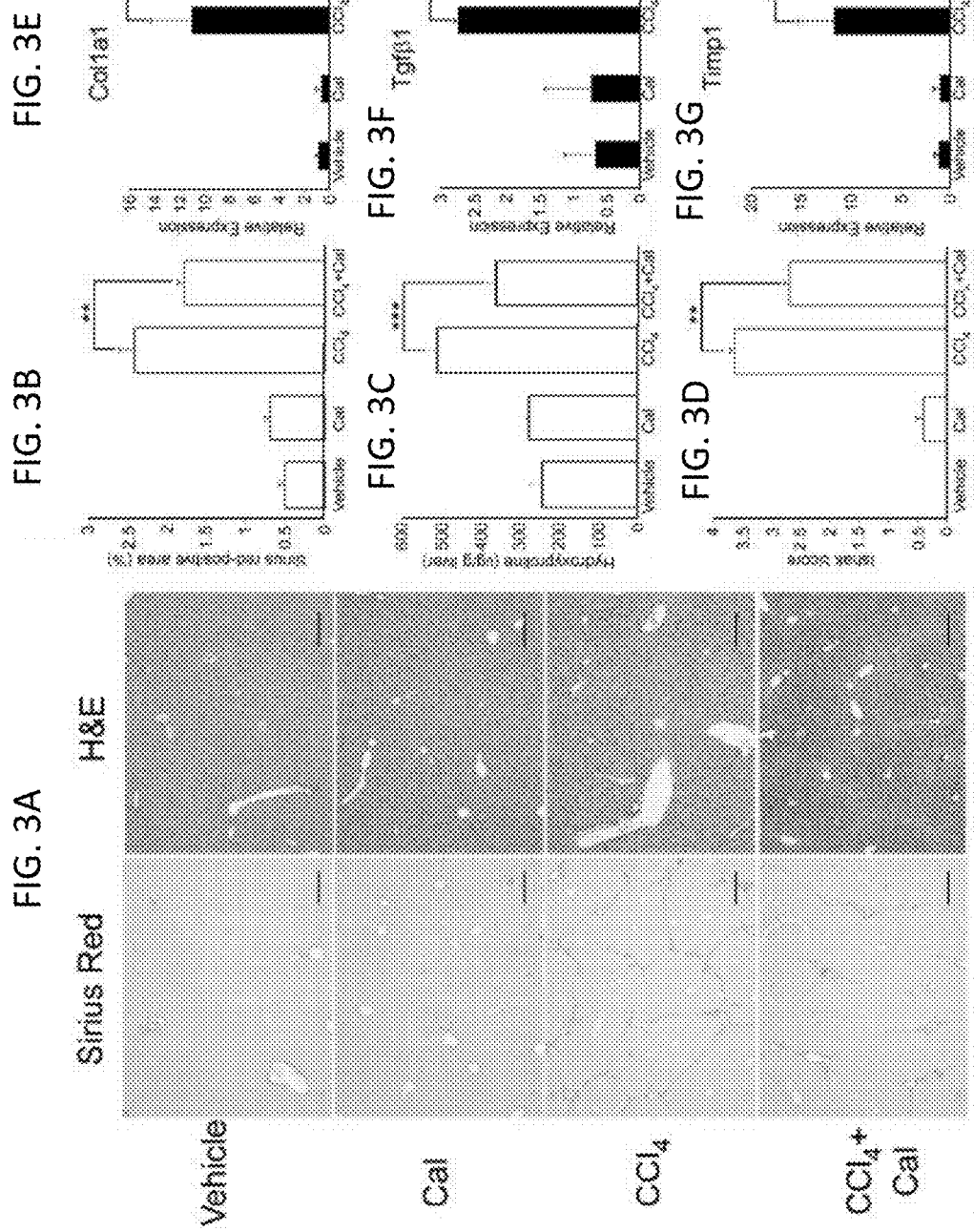

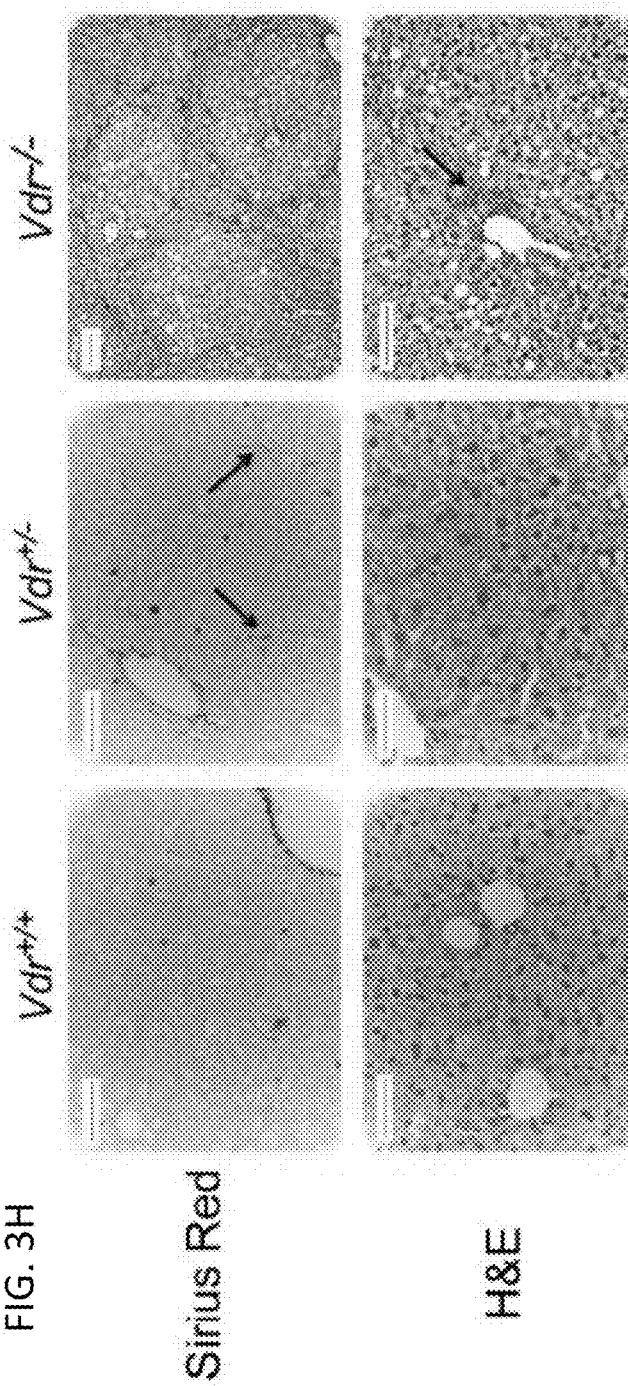
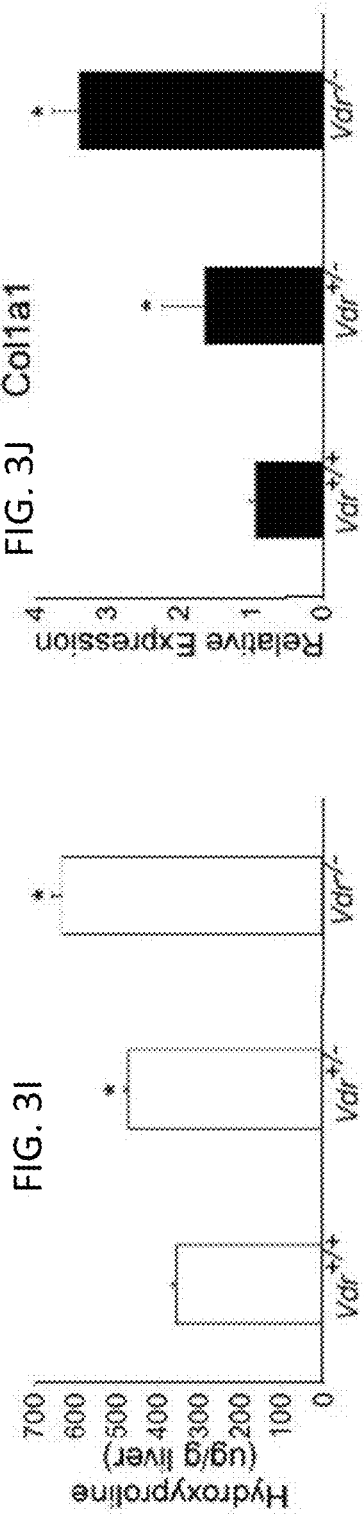
FIG. 3H
FIG. 3I
FIG. 3J

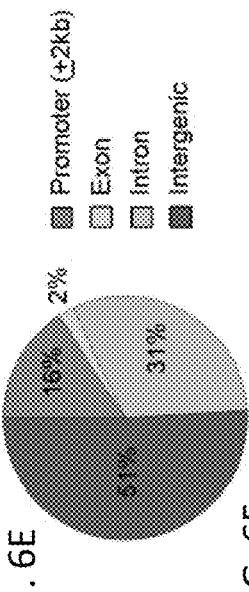
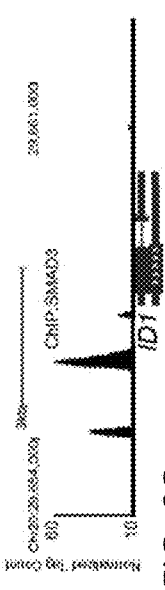
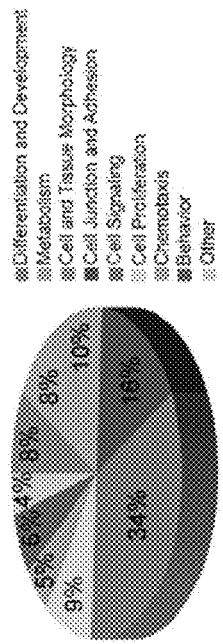
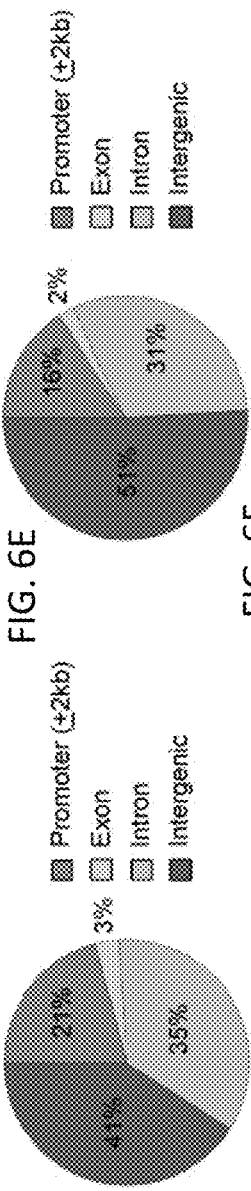
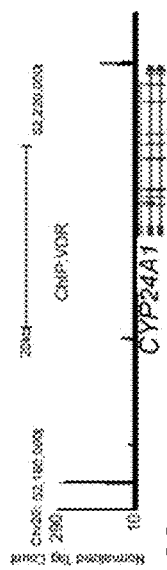
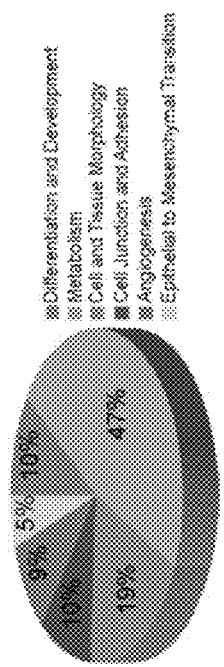
FIG. 6A – FIG. 6H

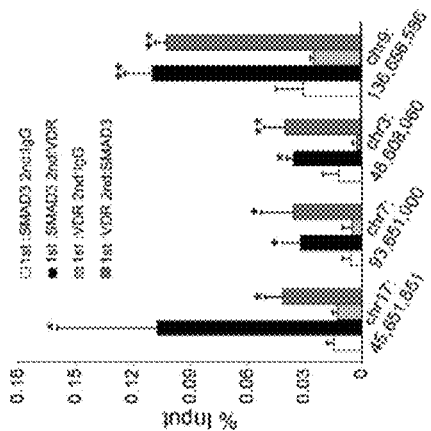
FIG. 8A
FIG. 8B
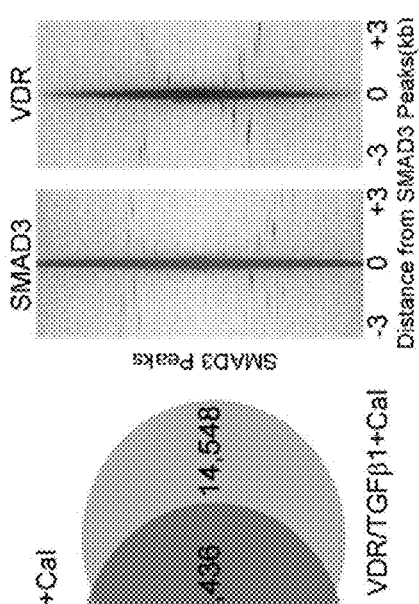
FIG. 8C
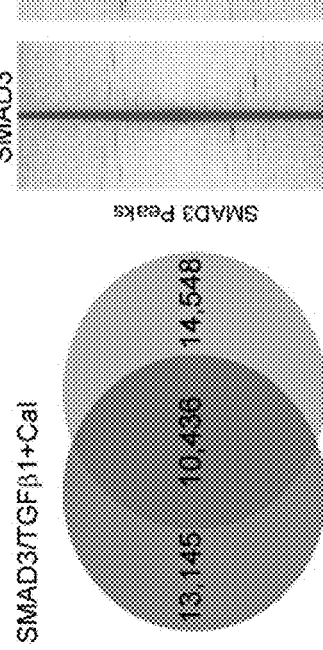
FIG. 8D
FIG. 8E
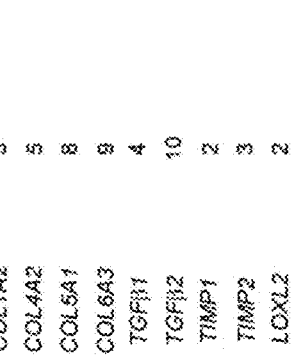
FIG. 8F
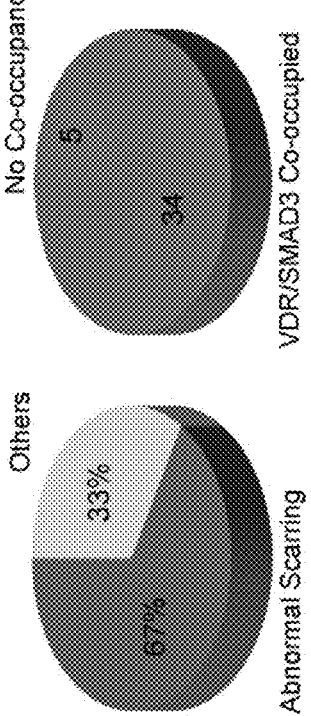

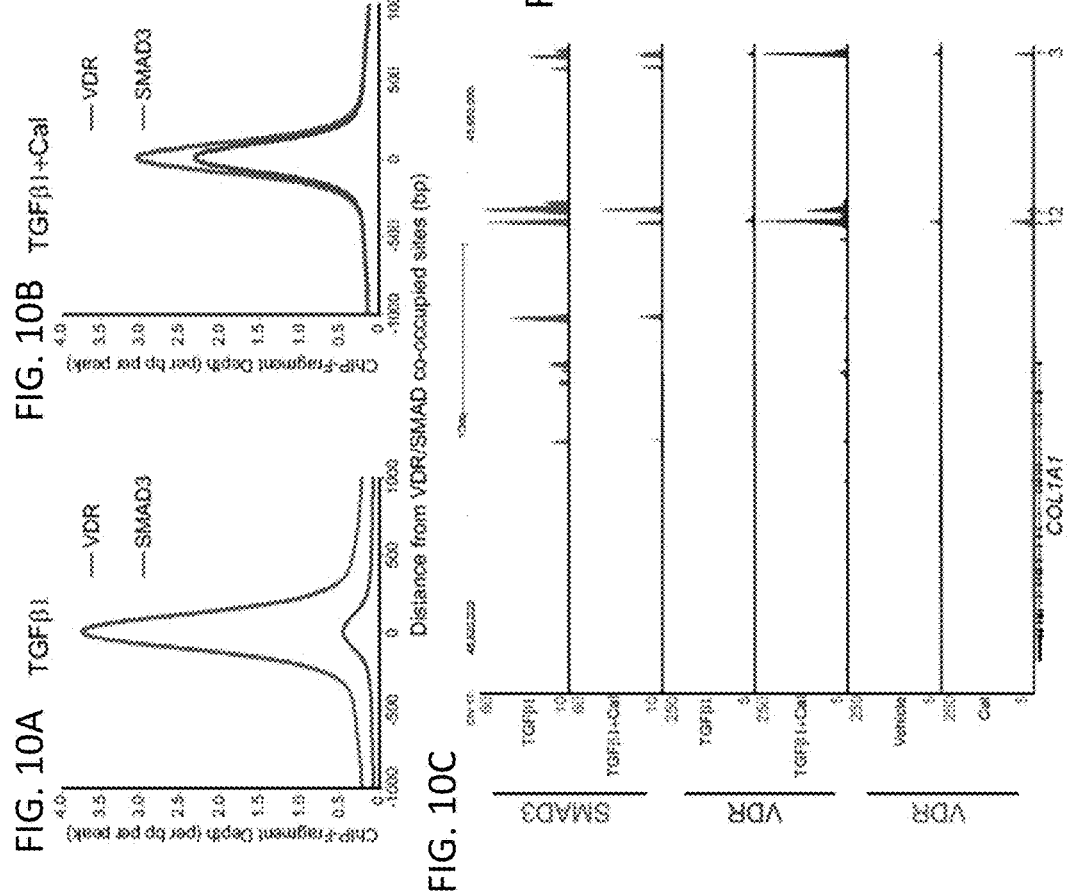
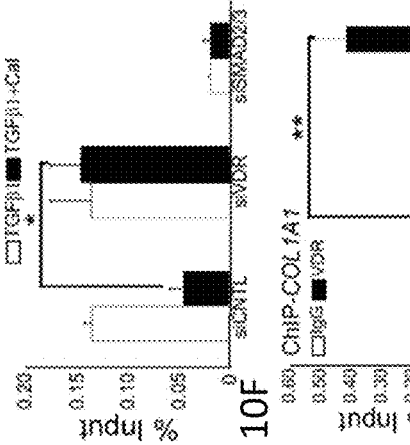
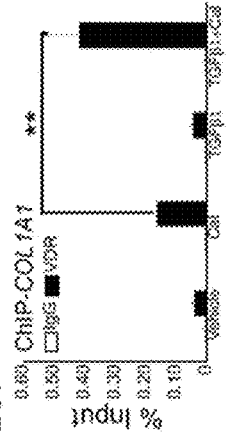
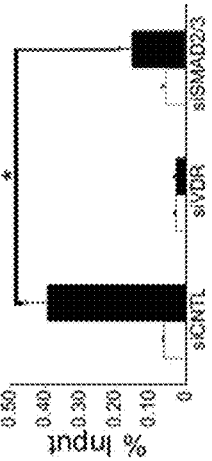

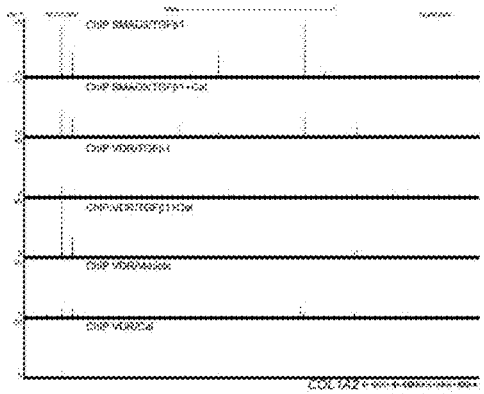

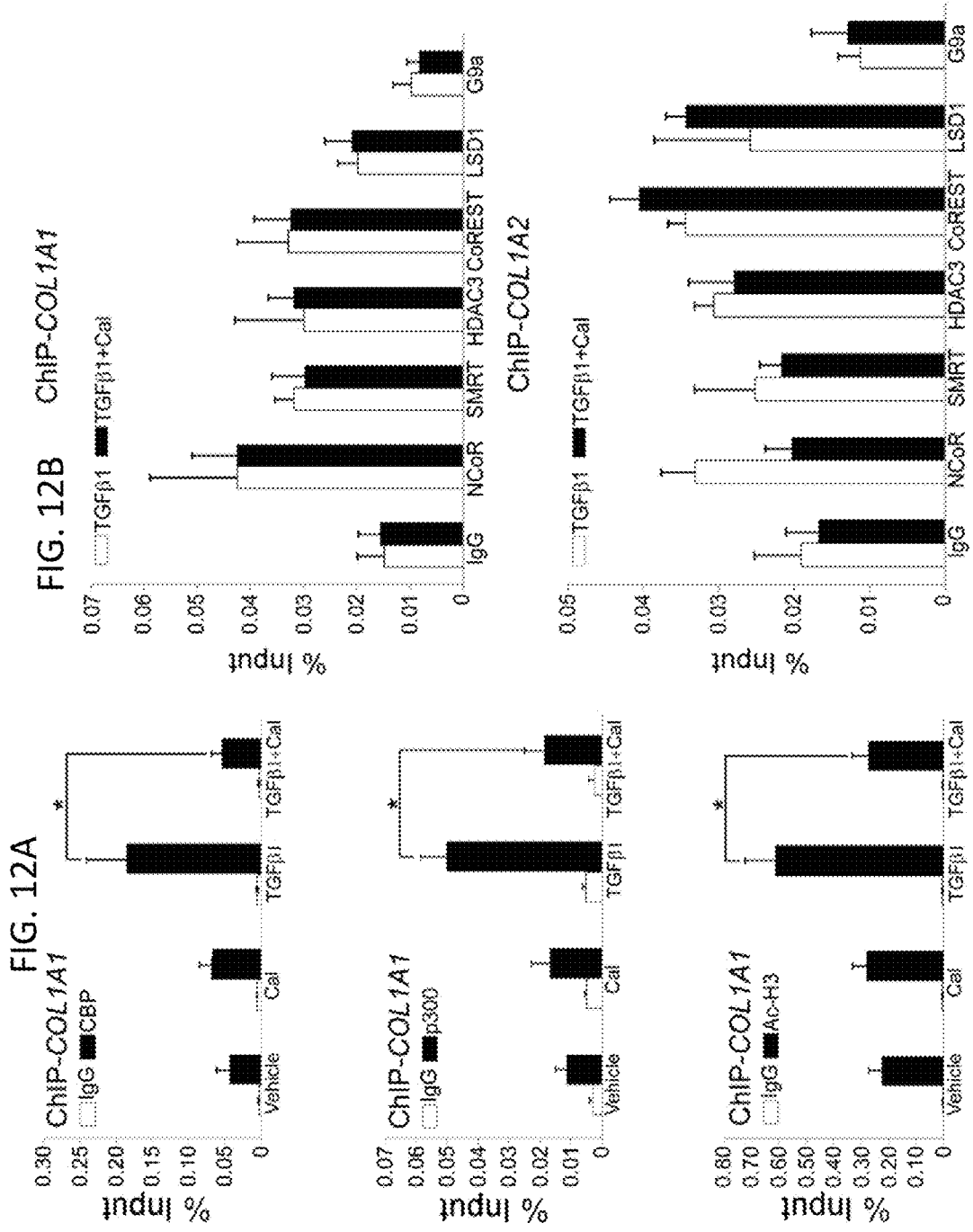

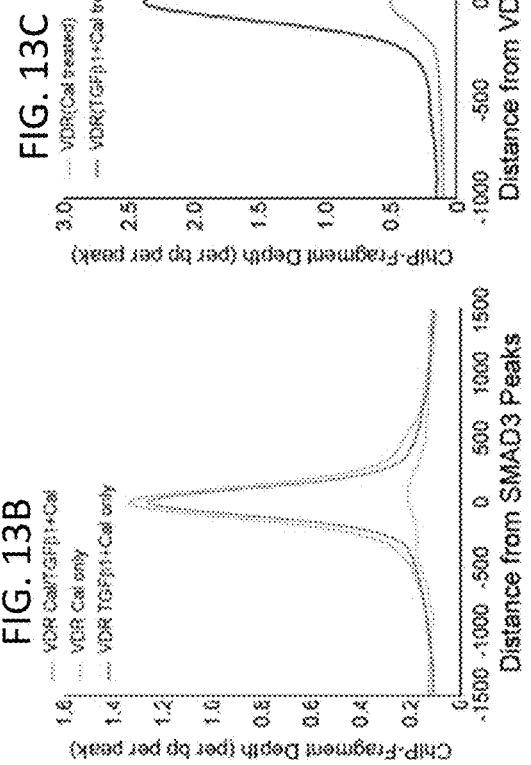
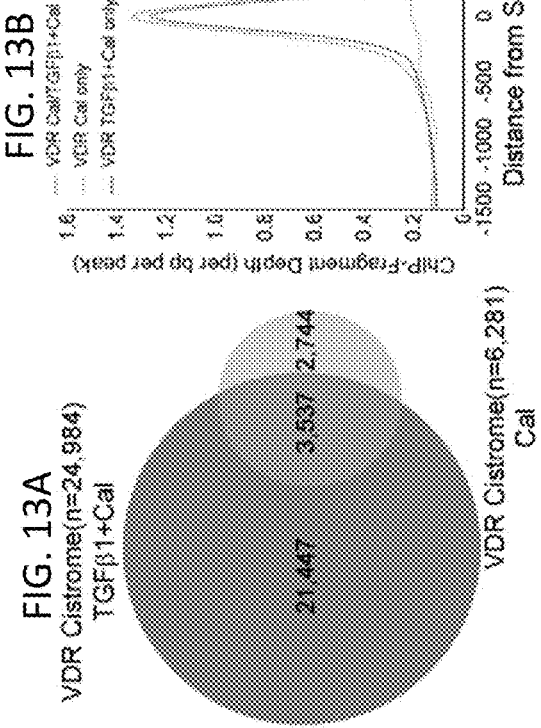
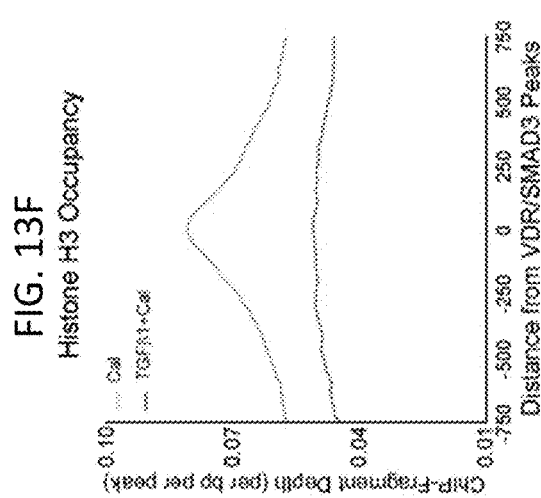
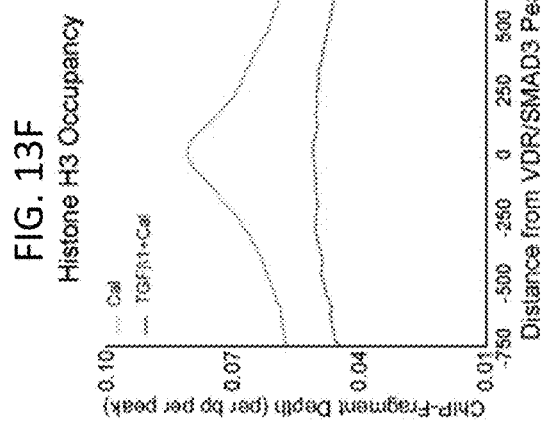
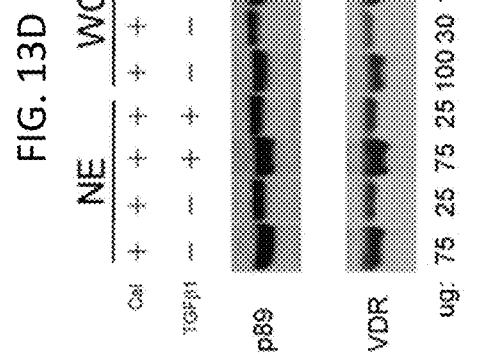

VITAMIN D RECEPTOR/SMAD GENOMIC CIRCUIT GATES FIBROTIC RESPONSE

CROSS REFERENCE TO RELATED APPLICATIONS

This application is a continuation of International Application No. PCT/US2014/035235, filed Apr. 24, 2014, which claims the benefit of the earlier filing date of U.S. Provisional Application No. 61/815,575 filed Apr. 24, 2013, both herein incorporated by reference.

ACKNOWLEDGMENT OF GOVERNMENT SUPPORT

This invention was made with government support under DK057978, HL105278, DK090962, HL088093, ES010337 and CA014195 awarded by The National Institutes of Health. The government has certain rights in the invention.

FIELD

This disclosure provides compositions that include a nanoparticle and a compound that increases the biological activity of a vitamin D receptor (VDR) (e.g., a VDR agonist), as well as methods of using such compounds, for example to retain or increase storage of vitamin A, vitamin D, and/or lipid in a cell, for example to treat or prevent fibrosis.

BACKGROUND

Hepatic fibrosis, defined by excessive accumulation of extracellular matrix (ECM) and resultant loss of pliability and liver function, is the result of wound-healing responses triggered by either acute or chronic liver injury (Bataller and Brenner, 2005; Hernandez-Gea and Friedman, 2011; Lee and Friedman, 2011). The main causes of liver injury leading to fibrosis in industrialized countries include chronic hepatitis virus (HBV/HCV) infection, alcohol abuse, and increasingly, nonalcoholic steatohepatitis (NASH) (Friedman, 1999, 2003; Friedman and Bansal, 2006; Siegmund et al., 2005). With persistent injury, there is progressive deposition of fibrillar collagens, eventually leading to parenchymal nodules surrounded by collagen bands, the histological signature of hepatic cirrhosis (Bataller and Brenner, 2005; Friedman, 2003).

Chronic liver disease and cirrhosis represents a major global health concern (Bataller and Brenner, 2005). In Australia and the UK, chronic liver disease is the $5^{th}$ most common cause of death, after heart disease, cancer, stroke and chest disease (Williams, 2006). In the US, they are ranked as the $8^{th}$ most common cause of mortality (Kim et al., 2002). Currently, no anti-fibrotic therapies for chronic liver disease have been approved by the FDA (Cohen-Naftaly and Friedman, 2011), and where the underlying cause of the liver disease cannot be ameliorated, therapeutic options are limited to addressing the consequent complications, such as portal hypertension, hepatocellular carcinoma and liver failure. Therefore, a greater understanding of molecular mechanisms regulating the hepatic fibrogenic response in liver is needed for identification of novel targets for successful anti-fibrotic therapies.

The central players in liver fibrosis are non-parenchymal cells (NPCs) such as hepatic stellate cells (HSCs) (Bataller and Brenner, 2005; Bouwens et al., 1992), which are the main producers of ECM (Friedman, 2008; Friedman et al., 1985; Reynaert et al., 2002). In the healthy liver, HSCs are retinoid (Vitamin A) storage cells located in the space of Disse, between the sinusoidal endothelium and hepatocytes (Friedman, 2008). Following injury, paracrine stimuli cause HSCs to undergo dramatic phenotypic changes (in a process called activation), whereby they exhibit proliferation, contractility and loss of retinoid stores, accompanied by secretion of chemokines, cytokines and pathological extracellular matrix components (Friedman, 2008; Geerts, 2001). While the precise mechanisms regulating this process have yet to be elucidated, transforming growth factor β1 (TGFβ1) signaling is recognized as one of the most potent pro-fibrotic pathways responsible for ECM synthesis (Breitkopf et al., 2006; Inagaki and Okazaki, 2007).

TGFβ is a multifunctional cytokine with profound effects on cell division, differentiation, migration, adhesion, organization and death. There are three major isoforms of TGFβ (TGFβ1, TGFβ2 and TGFβ3) and TGFβ1 is the principal isoform implicated in liver fibrosis (Inagaki and Okazaki, 2007). Following liver injury, TGFβ 1, derived from both paracrine and autocrine sources, binds to type I and type II serine/threonine receptor kinases on the cell surface of HSCs (Inagaki and Okazaki, 2007). Subsequently, its downstream effectors SMAD2 and SMAD3 are phosphorylated and released into the cytosol, where they form a complex with SMAD4.

This SMAD complex can then translocate into the nucleus, recognize SMAD-binding elements (SBE) on the genome and directly regulate target genes (Feng and Derynck, 2005; Massague et al., 2005). Thus, deciphering the TGFβ-SMAD transcriptional network in HSCs and understanding how it can be controlled by extracellular and intracellular factors is key to development of effective anti-fibrotic strategies.

SUMMARY

Although a physiological role for vitamin D in hepatic function has long been dismissed due to low levels of VDR expression in liver (Bookout et al., 2006; Han et al., 2010), it is shown herein that VDR is a modulator of liver fibrosis. For example, in a standard mouse model of hepatic injury, administration of the synthetic VDR agonist calcipotriol reduces both collagen deposition and fibrotic gene expression. It is also shown that Vdr knockout mice develop spontaneous liver fibrosis, proving a role for this receptor in normal liver homeostasis. Mechanistic studies revealed that activation of VDR signaling antagonizes a wide range of TGFβ/SMAD-dependent transcriptional responses on pro-fibrotic genes in hepatic stellate cells (HSCs). Mapping of genome-wide binding sites of VDR and SMAD3 revealed overlapping DNA occupancy of these transcription factors on cis-regulatory elements of pro-fibrotic genes. In addition, TGFβ-SMAD signaling enhanced the accessibility of liganded VDR with these genomic loci, which in turn antagonized recruitment of SMAD3. This dynamic VDR/SMAD genomic feedback circuit represents a previously unrecognized mechanism for regulating hepatic fibrogenesis.

Based on these observations, provided herein are compositions that include a nanoparticle and a compound that increases the biological activity of a vitamin D receptor (VDR), such as a compound that increases one or more of storage of vitamin A, vitamin D and/or lipids by a cell. The nanoparticles can be used to deliver the vitamin D agonists to the liver, pancreas, or kidney. In one example, the nanoparticles include one or more of albumin, retinol binding protein, mannose-6-phosphate modified albumin (e.g., see Li et al., *J. Pharm. Pharmacol.* 2009, 61(9): 1155-61, for example to target the nanoparticle to a hepatic stellate cell), fatty acid ester, or retinyl ester. Such agents can be present the surface of the nanoparticle (e.g., coated with one or more of these agents). In some examples, the nanoparticle is a lipid nanoparticle or polymeric nanoparticle. Examples of VDR agonists that can be present in or on the nanoparticle include but are not limited to vitamin D, a vitamin D precursor, a vitamin D analog, a vitamin D receptor ligand, a vitamin D receptor agonist precursor, and combinations thereof. The disclosed compositions can include other therapeutic agents, such as a chemotherapeutic (e.g., gemcitabine), a biologic (e.g., monoclonal antibody), or combinations thereof.

Also provided are methods of using a therapeutically effective amount of the disclosed compositions to increase or retain vitamin A, vitamin D, and/or lipid in a cell, such as an epithelial or stellate cell. Such methods can be performed in vitro or in vivo. For example, a therapeutically effective amount of the composition can be administered to a subject in need thereof, thereby increasing or retaining vitamin A, vitamin D, and/or lipid in epithelial and/or stellate cells in the subject. In some examples, the subject has a liver disease, kidney disease, or pancreatic disease, such as one or more of alcohol liver disease, fatty liver disease, liver fibrosis/cirrhosis, biliary fibrosis/cirrhosis, liver cancer, hepatitis B virus infection, hepatitis C virus infection, sclerosing cholangitis, Budd-Chiari syndrome, jaundice, nonalcoholic steatohepatitis, hemochromatosis, Wilson's disease, hepatocellular carcinoma, cholangiocarcinoma, angiosarcoma, hemangiosarcoma, pancreatic fibrosis, pancreatic ductal adenocarcinoma (PDA), or fibrosis of the kidney.

Also provided are methods of increasing expression of VDR by a stellate cell (such as a hepatic, pancreatic, lung, heart, or kidney stellate cell). Such methods can include contacting the stellate with an amount of a VDR agonist sufficient to enhance binding of VDR agonist to the VDR by at least 10-fold.

The disclosure also provides methods of screening for an agent that can treat fibrosis, such as liver, pancreatic, or kidney fibrosis. Such methods can include contacting a stellate cell (such as a hepatic, pancreatic, lung, heart, or kidney stellate cell) with one or more test agents and optionally TGF-β1. Subsequently, production of a VDR agonist by the stellate cell, production or expression of CYP24A1 by the stellate cell, production, post-translational modification (phosphorylation), or expression of SMAD3 by the stellate cell, binding of a VDR agonist to the VDR, or combinations thereof, are detected. Test agents are selected that increase production of the VDR agonist by the stellate cell by at least 5-fold relative to the absence of the one or more test agents, increase production of CYP24A1 by the stellate cell by at least 5-fold relative to the absence of the one or more test agents, reduce production, post-translational modification (phosphorylation), or expression of SMAD3 by the stellate cell by at least 1.5-fold relative to the absence of the one or more test agents, or combinations thereof. The selected test agents are agents that can treat fibrosis. In some examples, the method also includes determining whether the one or more test agents have hypercalcemic effects in vitro or in vivo.

The foregoing and other objects and features of the disclosure will become more apparent from the following detailed description, which proceeds with reference to the accompanying figures.

BRIEF DESCRIPTION OF THE DRAWINGS

FIGS. 2A-2F. Preventive Effect of Calcipotriol during Liver Fibrosis in $CCl_4$-Treated Mice. (A) Molecular structure of calcitriol ($1,25(OH)_2D_3$) and calcipotriol. (C) Sirius red (left) and H&E (right) staining of a representative liver from wild type C57BL/6J mice pre-treated with calcipotriol (Cal, 20 µg/kg, oral gavage) prior to $CCl_4$/calcipotriol co-treatment for 4 weeks (n=5). (D) and (E) Quantification of fibrosis based on Sirius red staining (D) and the Ishak score evaluating hepatic fibrosis based on H&E staining (E). (F) and (B) Hepatic hydroxyproline content (F) and serum calcium concentration (B) in C57BL/6J mice treated with vehicle (DMSO) (n=3), carbon tetrachloride ($CCl_4$, 0.5 ml/kg, n=6), calcipotriol (Cal, 20 µg/kg, n=3) and $CCl_4$ plus calcipotriol (n=6) for 4 weeks (see FIG. 3).

FIG. 3A-3J. Systemic Administration of Calcipotriol Attenuates Liver Fibrosis in $CCl_4$-Treated Mice while Genetic Abrogation of Vdr Results in Spontaneous Liver Fibrosis. (A) Livers from 4 wk-treated C57BL/6J mice (vehicle (DMSO) (n=3), carbon tetrachloride ($CCl_4$, 0.5 ml/kg i.p., n=6), calcipotriol (Cal, 20 µg/kg oral gavage, n=3) and $CCl_4$ plus calcipotriol (n=6)) stained with Sirius red (left) and H&E (right). Scale bar, 200 µm. Fibrosis quantified by (B) Sirius red staining, (C) hydroxyproline content and (D) H&E staining (Ishak score). Asterisks denote statistically significant differences (Student's unpaired t-test, p<0.01,*p<0.001). (E)-(G) RT-qPCR measurement of hepatic gene expression levels of Col1a1, Tgfβ1 and Timp1. Data represents the mean±SEM. Asterisks denote statistically significant differences (Student's unpaired t-test, p<0.01,*p<0.001). (H) Sirius red (top) and H&E (bottom) stained liver sections from $Vdr^{+/+}$ (n=3), $Vdr^{+/-}$ (n=4) and $Vdr^{-/-}$ (n=2 of 4) mice maintained on a calcium- and phosphate-supplemented rescue diet (2% Calcium, 1.25% Phosphorus, 20% Lactose) for 6 months prior to sacrifice. Arrows indicate peri-sinusoidal fibrosis ($Vdr^{+/-}$ mice) and inflammatory cell infiltrate ($Vdr^{-/-}$ mice), respectively. Scale bar, 50 km. (I) Fibrosis quantified by hydroxyproline content and (J) Col1a1 mRNA expression using the two of four livers from $Vdr^{-/-}$ mice exhibiting the least fibrosis on Sirius red staining (refer to results). Data represents the mean±SEM. Asterisks denote statistically significant differences (Student's unpaired t-test, *p<0.05).

Figure 5A:
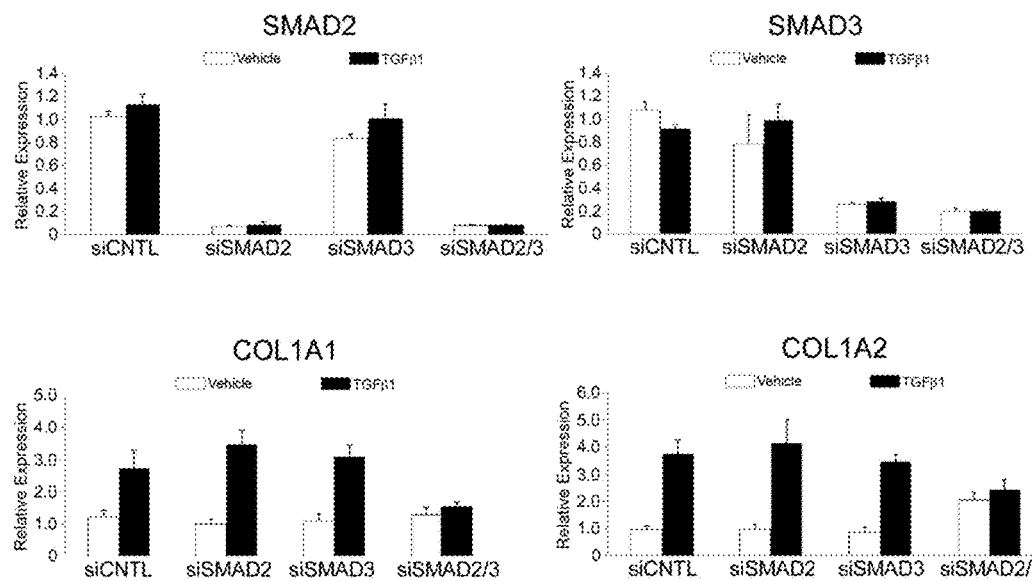
Figure 5B:
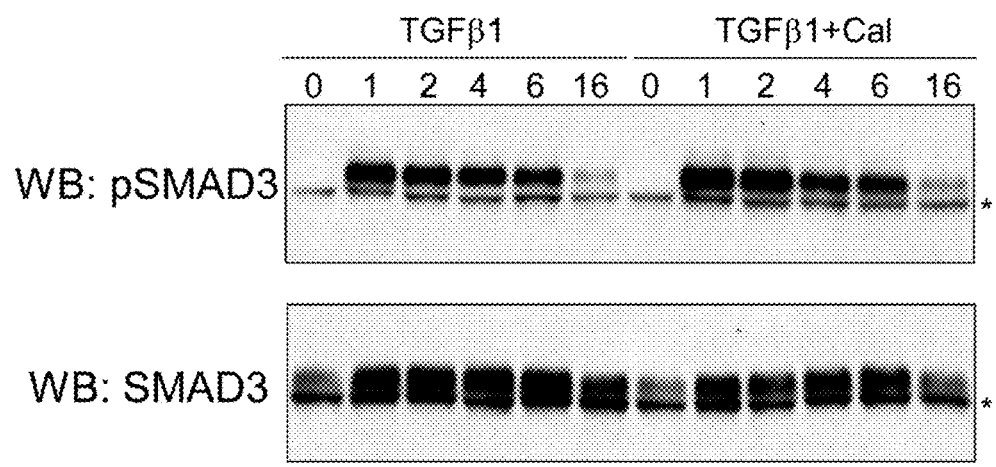

FIGS. 5A-5B. SMAD2/3 Are Required for TGFβ-Induced Fibrotic Gene Expression.

FIG. 5A Relative expression determined by RT-qPCR of SMAD2, SMAD3, COL1A1 and COL1A2 in LX-2 cells transfected with control (CNTL), SMAD2, SMAD3 or SMAD2/3-specific siRNAs 48 hours prior to a 24 hour treatment with vehicle or TGFβ1 (1 ng/ml).

FIG. 5B Total and phosphorylated SMAD3 in LX-2 cells treated with TGFβ1 (1 ng/ml)+/−calcipotriol (100 nM) for the indicated times. Nuclear extracts were immunoprecipitated using a SMAD2/3 antibody prior to Western blot analysis. Asterisks denote non-specific bands.

FIGS. 6A-6H. VDR and SMAD3 Cistromes in Hepatic Stellate Cells. (A) and (E) Pie charts illustrating genomic locations of VDR and SMAD3 binding sites in treated LX-2 cells (calcipotriol (100 nM) and TGFβ1 (1 ng/ml) for 4 hours following 16 hours calcipotriol (100 nM) pretreatment, FDR<0.0001). Promoter regions, <2 kb from TSS; intergenic regions, not promoter, intron or exon. (B) and (F) Representative ChIP-Seq reads for VDR and SMAD3 aligned to the CYP24A1 and ID1 genes, respectively. (C) and (G) Gene ontology (GO) classification of genes annotated with VDR and SMAD3 binding sites. (D) and (H) De novo motif analysis performed on sequences located within 100 bp of VDR and SMAD3 peaks (FDR<0.0001).

FIGS. 7A-7D. Gene Tracks Depicting Normalized VDR and SMAD3 ChIP-Seq Tags for Their Target Genes. (A) SPP1, (B) BGLAP, (C) SMAD7 and (D) TGFβ1.

Figure 4C:
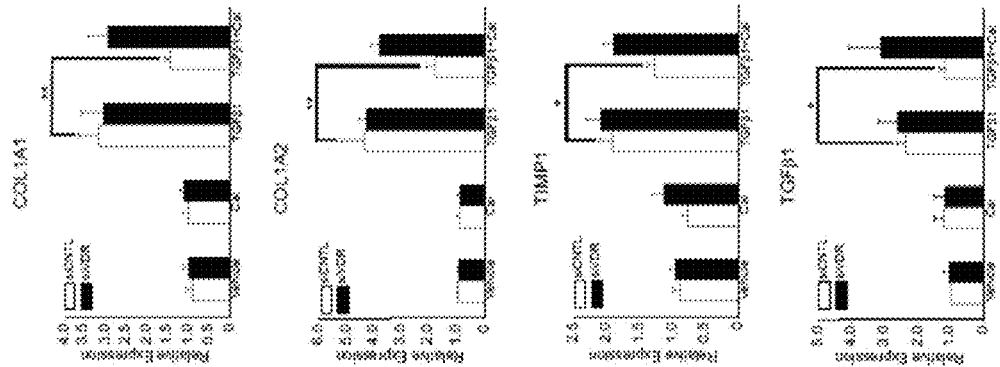
FIGS. 4A-4C. VDR Signaling Suppresses TGFβ-induced Pro-Fibrotic Genes. (A) Heat map comparing 519 differentially expressed genes in freshly isolated rat HSCs (quiescent HSCs, Q-HSCs), activated HSCs (A-HSCs, 3 days culture on plastic) and cells cultures in the presence of 10 nM 1,25(OH)$_2$D$_3$(A-HSCs+1,25(OH)$_2$D$_3$). Euclidean clustering of both rows and columns using log 2 transformed microarray expression data, n=2 per treatment group. (B) Heat map of fold expression change of genes involved in fibrosis in primary rat HSCs treated with TGFβ1 (1 ng/ml) and TGFβ1 plus 1,25(OH)$_2$D$_3$(100 nM) for 24 hours, n=2 per treatment group. (C) Fibrotic gene expression in control (siCNTL) or VDR-specific (siVDR) siRNA transfected LX-2 cells treated with Vehicle (DMSO), calcipotriol (Cal, 100 nM), TGFβ1 (1 ng/ml), or TGFβ1+Cal for 16 hours. Data represents the mean±SEM of at least three independent experiments performed in triplicate. Asterisks denote statistically significant differences (Student's unpaired t-test, *p<0.05, **p<0.01).

FIGS. 8A-8F. Antagonism of TGFβ Signaling via VDR/SMAD3 Genomic Crosstalk. (A) Venn diagram depicting overlap of VDR and SMAD3 genomic binding sites in LX-2 cells treated as in FIG. 4. (B) Intensity plots showing hierarchical clustering of ChIP-fragment densities as a function of distance from the center of statistically significant SMAD3 binding peaks (23,532 peaks, FDR=0.0001). Intensity around position 0 of VDR (blue) indicates overlapping VDR/SMAD3 sites with SMAD3 (red) acting as a positive control. (C) ChIP-re-ChIP of treated LX-2 cells analyzed by qPCR at VDR and SMAD3 co-bound sites. Occupancy is expressed relative to input chromatin. (D) Common human phenotypes enriched in genes co-occupied by VDR and SMAD3. (E) The number of TGFβ1/VDR-coregulated pro-fibrotic genes harboring genomic sites co-occupied by VDR and SMAD3. (F) The number of VDR/SMAD3 co-occupied sites observed in pro-fibrotic genes coregulated by TGFβ1 and VDR in LX-2 cells treated as in FIGS. 6A-6H. Data represents the mean±SEM of at least three independent experiments performed in triplicate. Asterisks denote statistically significant differences (Student's t-test, *p<0.05, **p<0.01). See also Table 3 & FIGS. 9A-9B.

Figure 9A:
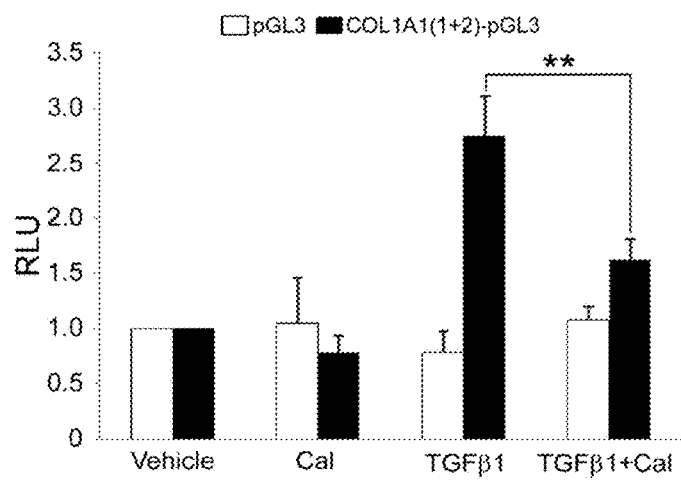
Figure 9B:
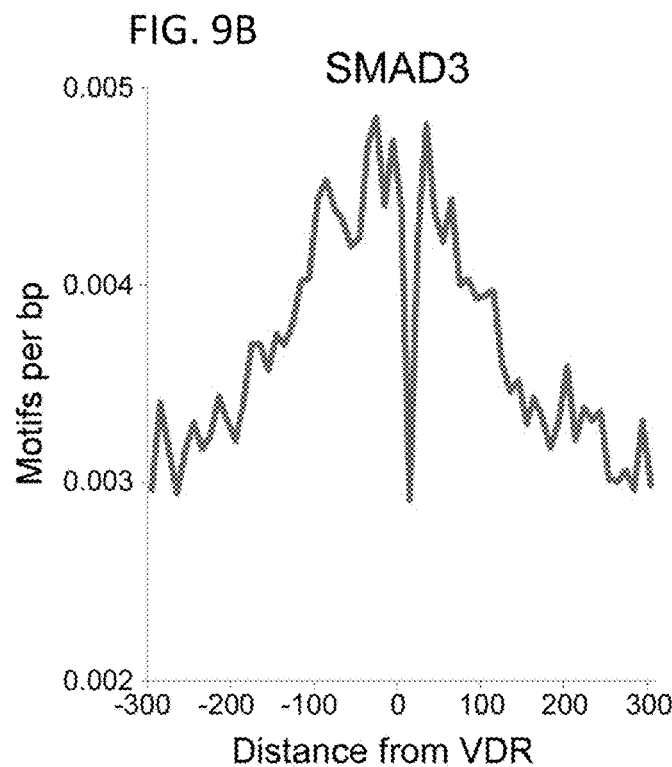

FIGS. 9A and 9B. The VDR/SMAD3 Co-Bound Sites Mediate Antagonistic Actions Between Vitamin D and TGFβ.

FIG. 9A LX-2 cells transfected with an empty pGL3 reporter or pGL3 reporter bearing two (1+2) VDR/SMAD co-bound sites of COL1A1 depicted in FIG. 10C and an internal control β-galactosidase expression vector (pCMX-LacZ) were treated with different conditions as indicated. Transfected whole-cell lysates were assayed for normalized luciferase activities using β-galactosidase activity as an internal control. Luciferase activities (RLU) are expressed relative to the normalized luciferase activity obtained in cells transfected with the same reporter and treated with vehicle, which was arbitrarily assigned a value of 1. Data represents the mean±SEM of at least three independent transfections performed in triplicate. Asterisks denote statistically significant differences (Student's t test, **p<0.01).

FIG. 9B Moving averages of SMAD3 binding frequency within a 200 bp window are centered on VDR binding sites within the genomic regions co-bound by VDR and SMAD3.

FIGS. 10A-10G. Genomic Antagonism between VDR and SMAD. (A) and (B) Plots of VDR and SMAD3 ChIP-Seq signal intensity relative to the center of VDR/SMAD3 co-occupied sites in LX-2 cells (TGFβ1 (1 ng/ml)±calcipotriol (100 nM) for 4 hours). (C) Representative ChIP-Seq reads aligned to COL1A1 for VDR and SMAD3 in treated LX-2 cells (Vehicle (DMSO), Calcipotriol (Cal, 100 nM), TGFβ1 (1 ng/ml), or TGFβ1+calcipotriol). The three co-occupied sites are designated as 1, 2 and 3. (D) and (F) ChIP-qPCR at COL1A1 regulatory region #1 co-bound by VDR and SMAD3 in LX-2 cells treated as above. (E) and (G) ChIP-qPCR at COL1A1 regulatory region #1 of control (siCNTL), VDR-specific (siVDR), or SMAD3-specific (siSMAD3) siRNA transfected LX-2 cells treated as above. Occupancy is expressed relative to input chromatin. Data represents the mean±SEM of at least three independent experiments performed in triplicate. Asterisks denote statistically significant differences (Student's t-test, *p<0.05, **p<0.01).

FIGS. 11A-11F. Gene Tracks Depicting Normalized VDR and SMAD3 ChIP-Seq Tags for Fibrotic Genes under Different Conditions as Indicated (A)-(F).

FIGS. 12A-12B. Coactivator/Corepressor Recruitment and Histone H3 Acetylation Status at Regulatory Regions of Fibrotic Genes Co-occupied by VDR and SMAD. (A) Treated LX-2 cells (Vehicle (DMSO), Calcipotriol (Cal, 100 nM), TGFβ1 (1 ng/ml), or TGFβ1+calcipotriol) were immunoprecipitated using antibodies recognizing CBP, p300 and acetylated histone H3, and analyzed by qPCR using primers flanking COL1A1 regulatory region #1 co-bound by VDR and SMAD3. The level of occupancy is expressed relative to input chromatin in LX-2 cells treated with corresponding conditions. Data represents the mean+/−SEM of at least three independent experiments performed in triplicate. Asterisks denote statistically significant differences (Student's t test, *p<0.05). (B) Treated LX-2 cells (TGFβ1 (1 ng/ml)+/−calcipotriol (100 nM)) were immunoprecipitated with the indicated antibodies, and analyzed by qPCR using primers flanking either COL1A1 or COL1A2 regulatory regions. The level of occupancy is expressed relative to input chromatin in LX-2 cells treated with corresponding conditions.

FIGS. 13A-13F. TGFβ Unmasks a Signal Dependent VDR Citrome. (A) Venn diagram displaying overlapping VDR cistromes in treated LX-2 cells (FDR<0.0001). (B) Plot of VDR ChIP-Seq peak locations depicted in (A) categorized as VDR Cal/TGFβ1+Cal (3,537 overlapping), VDR Cal only (2,744 calcipotriol-only), or VDR TGFβ1+Cal only (21,447 calcipotriol+TGFβ1-only) relative to the center of SMAD3 binding sites in LX-2 cells. (C) Plot of VDR ChIP-Seq signal intensity relative to the center of VDR/SMAD3 co-occupied sites in LX-2 cells treated as indicated. (D) Western blot for VDR in nuclear and whole cell extracts (NE, WCE) from LX-2 cells treated as above. TFIIH (p89) was used as a loading control. (E) The percentages of calcipotriol-only, calcipotriol+TGFβ 1-only or calcipotriol/calcipotriol+TGFβ1-overlapping VDR ChIP-Seq peaks containing VDREs. (F) Plot of histone H3 ChIP-Seq signal intensity relative to the center of VDR/SMAD3 co-occupied sites in LX-2 cells treated as indicated.

FIGS. 14A-14D. VDR/SMAD Genomic Circuit. (A) and (B) Time course of VDR and SMAD3 binding at the COL1A1 regulatory region #1 in treated LX-2 cells (vehicle (DMSO), calcipotriol (100 nM), TGFβ1 (1 ng/ml), TGFβ1 (1 ng/ml)+calcipotriol (100 nM)) determined by ChIP-qPCR. LX-2 cells were pretreated with calcipotriol (100 nM) for 16 hours prior to time course assay and occupancy is expressed relative to input chromatin. Data represents the mean±SEM of at least three independent experiments performed in triplicate. Asterisks denote statistically significant differences compared to calcipotriol-induced VDR occupancy or TGFβ1-induced SMAD3 occupancy of corresponding time point (Student's unpaired t-test, *p<0.05, **p<0.01). (C) Time course of TGFβ1+calcipotriol-induced VDR and SMAD3 binding, normalized to calcipotriol alone or TGFβ1 alone, respectively. Data represents the mean±SEM of at least three independent experiments performed in triplicate. (D) Model depicting proposed VDR/SMAD genomic circuit controlling pro-fibrogenic responses in HSCs.

SEQUENCE LISTING

The nucleic acid sequences are shown using standard letter abbreviations for nucleotide bases as defined in 37 C.F.R. 1.822. Only one strand of each nucleic acid sequence is shown, but the complementary strand is understood as included by any reference to the displayed strand.

SEQ ID NOS: 1-34 are primer sequences used to measure expression of various genes.

DETAILED DESCRIPTION

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All GenBank® Accession numbers referenced herein are incorporated by reference for the sequence available on Apr. 24, 2014. All references, including patents and patent applications, and GenBank® Accession numbers cited herein are incorporated by reference.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

Suitable methods and materials for the practice or testing of the disclosure are described below. However, the provided materials, methods, and examples are illustrative only and are not intended to be limiting. Accordingly, except as otherwise noted, the methods and techniques of the present disclosure can be performed according to methods and materials similar or equivalent to those described and/or according to conventional methods well known in the art and as described in various general and more specific references that are cited and discussed throughout the present specification.

In order to facilitate review of the various embodiments of the disclosure, the following explanations of specific terms are provided:

Administration: The compositions provided herein can be delivered to a subject in need thereof using any method known in the art, such as oral, nasal, inhalational, rectal, vaginal, transdermal, and parenteral administration. Generally, parenteral formulations are those that are administered through any possible mode except ingestion. This term also refers to injections, whether administered intravenously, intrathecally, intramuscularly, intraperitoneally, intra-articularly, intratumorally, or subcutaneously, and various surface applications including intranasal, inhalational, intradermal, and topical application, for instance.

Contact: To bring one agent into close proximity to another agent, thereby permitting the agents to interact. For example, a composition containing a nanoparticle and a VDR agonist can be applied to a cell (for example in tissue culture), or administered to a subject, thereby permitting the nanoparticle/VDR agonist to interact with cells in vitro or in vivo.

Fibrosis: Refers to the formation or development of excess fibrous connective tissue in an organ or tissue as a reparative or reactive process, as opposed to a formation of fibrous tissue as a normal constituent of an organ or tissue. The term fibrosis includes at least liver/hepatic fibrosis, kidney/renal fibrosis, and pancreatic fibrosis. In particular examples the subjects treated herein have a fibrosis, such as a liver fibrosis.

Hepatic fibrosis is the accumulation of abnormal extracellular matrix (ECM) proteins and a resultant loss of liver function, and is an accompaniment of an inflammation-driven wound healing process triggered by chronic liver injury (Bataller & Brenner 2005 *J Clin Invest.*, 115(2):209-18). Common causes of liver injury that lead to fibrosis include chronic hepatitis C virus (HCV) infection, alcohol abuse, chronic hepatitis B infection (HBV) and nonalcoholic steatohepatitis (NASH), which represents the hepatic metabolic consequence of rising obesity and associated insulin resistance in the setting of an increasingly sedentary lifestyle (Bataller & Brenner 2005 *J Clin Invest.*, 115(2):209-18; Friedman 1999 *Am J Med.*, 107(6B):27S-30S; Siegmund et al., 2005 *Dig Dis.*, 23(3-4):264-74; Friedman & Bansal *Hepatology.*, 43(2 Suppl 1):S82-8). The inflammatory process that results from hepatic injury triggers a variety of cellular responses that include cell repair, regeneration, increased extracellular matrix turnover, and ultimately, in some patients, significant fibrosis. Progressive fibrosis of the liver eventually can result in cirrhosis, loss of liver function (decompensated cirrhosis), portal hypertension, and hepatocelluar carcinoma (Bataller & Brenner 2005 *J Clin Invest.* 115(2):209-18; Friedman 2003 *J. Hepatol.* 38(Suppl. 1):S38-S53).

Without being bound by theory, hepatic fibrogenesis is thought to be the result of a wound healing process that occurs after continued liver injury in which parenchymal cells proliferate to replace necrotic or apoptotic cells. This process is associated with an inflammatory response and a limited deposition of ECM. If the hepatic injury persists, eventually hepatocytes are replaced by abundant ECM components, including fibrillar collagen. The distribution of this fibrous material within the lobular architecture of the liver depends on the origin of the liver injury. In chronic viral hepatitis and chronic cholestatic disorders, the fibrotic tissue is initially located around the portal tracts, while in alcohol-induced liver disease and NASH, it is found in the pericentral and perisinusoidal areas (Friedman 2003 *J. Hepatol.*, 38(Suppl. 1):S38-S53; Popper & Uenfriend 1970. *Am. J. Med.*, 49:707-721). As fibrotic liver diseases advance, the pathology progresses from isolated collagen bands to bridging fibrosis, and ultimately, established cirrhosis with regenerative nodules of hepatocytes encapsulated within type I collagen bands (Popper & Uenfriend 1970. *Am. J. Med.*, 49:707-721).

Renal fibrosis causes significant morbidity and mortality as the primary acquired lesion leading to the need for dialysis or kidney transplantation. Renal fibrosis can occur in either the filtering or reabsorptive component of the nephron, the functional unit of the kidney. Experimental models have identified a number of factors that contribute to renal scarring, particularly derangements of physiology involved in the autoregulation of glomerular filtration. This in turn leads to replacement of normal structures with accumulated extracellular matrix (ECM). A spectrum of changes in the physiology of individual cells leads to the production of numerous peptide and non-peptide fibrogens that stimulate alterations in the balance between ECM synthesis and degradation to favor scarring. Almost all forms of end stage renal disease (ESRD) are characterized by significant renal fibrosis.

Fibrosis of the pancreas is a characteristic feature of chronic pancreatitis of various etiologies, and is caused by such processes as necrosis/apoptosis, inflammation, and duct obstruction. The initial event that induces fibrogenesis in the pancreas is an injury that may involve the interstitial mesenchymal cells, the duct cells and/or the acinar cells. Damage to any one of these tissue compartments of the pancreas is associated with cytokine-triggered transformation of resident fibroblasts/pancreatic stellate cells into myofibroblasts and the subsequent production and deposition of extracellular matrix. Depending on the site of injury in the pancreas and the involved tissue compartment, predominantly inter(peri)lobular fibrosis (as in alcoholic chronic pancreatitis), periductal fibrosis (as in hereditary pancreatitis), periductal and interlobular fibrosis (as in autoimmune pancreatitis) or diffuse inter- and intralobular fibrosis (as in obstructive chronic pancreatitis) develops.

Hepatic stellate cells (HSCs): Include pericytes found in the perisinusoidal space (a small area between the sinusoids and hepatocytes) of the liver. The hepatic stellate cell is the major cell type involved in liver fibrosis, which is the formation of scar tissue in response to liver damage. Stellate cells can be selectively stained with gold chloride, but their distinguishing feature in their quiescent (non-activated) state in routine histological preparations is the presence of multiple vitamin A-rich lipid droplets in their cytoplasm, which auto-fluoresce when exposed to ultraviolet (UV) light.

In the normal liver, stellate cells exist in a quiescent state. Quiescent stellate cells represent 5-8% of the total number of liver cells. Each cell has several long protrusions that extend from the cell body and wrap around the sinusoids. The lipid droplets in the cell body store vitamin A. Without being bound by theory, quiescent hepatic stellate cells are thought to play a role in physiological (normal) ECM production and turnover as well as acting as a liver-resident antigen-presenting cell, presenting lipid antigens to and stimulating proliferation of NKT cells.

When the liver is damaged, stellate cells can change into an activated state. The activated stellate cell is characterized by proliferation, contractility, and chemotaxis. The amount of stored vitamin A decreases progressively in liver injury. The activated stellate cell is also responsible for secreting excessive and pathological ECM components as well as reduced production of matrix degrading enzymes, which leads to fibrosis.

Hypercalcemia: An elevated calcium level in the blood, which can be caused by, for instance, elevated levels of $1\alpha,25(OH)_2$—VitD3 (Normal range: about 8.5 to 10.5 mg/dL or 2.2-2.6 mmol/L). It can be due to excessive skeletal calcium release, increased intestinal calcium absorption, or decreased renal calcium excretion.

Hypercalcemia per se can result in fatigue, depression, confusion, anorexia, nausea, vomiting, constipation, pancreatitis or increased urination. Abnormal heart rhythms also can result, and EKG findings of a short QT interval and a widened T wave suggest hypercalcemia.

Symptoms are more common at high calcium levels (12.0 mg/dL or 3 mmol/l). Severe hypercalcemia (above 15-16 mg/dL or 3.75-4 mmol/l) is considered a medical emergency: at these levels, coma and cardiac arrest can result.

Isolated: An "isolated" biological component (such as a nucleic acid molecule, peptide, or cell) has been purified away from other biological components in a mixed sample (such as a cell extract). For example, an "isolated" peptide or nucleic acid molecule is a peptide or nucleic acid molecule that has been separated from the other components of a cell in which the peptide or nucleic acid molecule was present (such as an expression host cell for a recombinant peptide or nucleic acid molecule).

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the compositions herein disclosed. For example a composition provided herein can be administered in the presence of one or more pharmaceutically acceptable carriers.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (for instance, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. Embodiments of other pharmaceutical compositions can be prepared with conventional pharmaceutically acceptable carriers, adjuvants, and counter-ions, as would be known to those of skill in the art. The compositions in some embodiments are in the form of a unit dose in solid, semi-solid, and liquid dosage forms, such as tablets, pills, capsules, lozenges, powders, liquid solutions, or suspensions.

SMAD3 (mothers against decapentaplegic homolog 3): OMIM 603109. Includes SMAD3 nucleic acid molecules and proteins. The SMAD3 protein is involved in cell signally and modulates TGFβ signals. SMAD3 sequences are publically available, for example from the GenBank® sequence database (e.g., Accession Nos. NP_001138574.1 and AAB81755.1 provide exemplary SMAD3 protein sequences, while Accession Nos. AH011390.1, NM_001145102.1, and AF016189.1 provide exemplary SMAD3 nucleic acid sequences). One of ordinary skill in the art can identify additional SMAD3 nucleic acid and protein sequences, including SMAD3 variants that retain SMAD3 biological activity (such as those variant sequences having at least 80%, at least 90%, at least 95%, at least 98%, or at least 99% sequence identity to these publicly available sequences or having such amounts of identity to a mature form of SMAD3).

Subject: Living multi-cellular vertebrate organisms, a category that includes both human and non-human mammals. The methods and compositions disclosed herein have equal applications in medical and veterinary settings. Therefore, the general term "subject" is understood to include all animals, including, but not limited to, humans or veterinary subjects, such as other primates (including monkeys), dogs, cats, horses, and cows. In one example, a subject is one that has, or is a risk to develop, fibrosis of the liver, pancreas, or kidney.

Therapeutically effective amount: An amount of a therapeutic agent (such as a composition provided herein that includes a VDR agonist), alone or in combination with other agents sufficient to prevent advancement of a disease, to cause regression of the disease, or which is capable of relieving symptoms caused by the disease, such as a symptom associated with fibrosis of the liver, pancreas or kidney, for example fever, respiratory symptoms, fibrotic content, pain or swelling. In one example, a therapeutically effective amount is an amount of a composition provided herein that includes a VDR agonist and a nanoparticle sufficient to reduce symptoms of fibrosis by at least 10%, at least 20%, at least 50%, at least 70%, or at least 90%. In one example, a therapeutically effective amount is an amount of a composition provided herein that includes a VDR agonist and a nanoparticle sufficient to increase an amount of vitamin A, vitamin D, and/or lipid in an epithelial or stellate cell by at least 10%, at least 20%, at least 50%, at least 70%, or at least 90%. In one example, a therapeutically effective amount is an amount of a composition provided herein that includes a VDR agonist and a nanoparticle sufficient to retain an amount of vitamin A, vitamin D, and/or lipid in an epithelial or stellate cell, such the amount does not decrease by more than 20%, such as no more than 10%, no more than 5%, or no more than 1%.

Transforming growth factor beta 1 (TGF-β1): OMIM 190180. Includes TGF-$β_1$ nucleic acid molecules and proteins. The TGFβ-1 protein helps control the growth and division (proliferation) of cells, the process by which cells mature to carry out specific functions (differentiation), cell movement (motility), and the self-destruction of cells (apoptosis). TGF-$β_1$ sequences are publically available, for example from the GenBank® sequence database (e.g., Accession Nos. NP_000651.3 and NP_035707.1 provide exemplary TGF-$β_1$ protein sequences, while Accession Nos. NM_000660 and NM_011577 provide exemplary TGF-$β_1$ nucleic acid sequences). One of ordinary skill in the art can identify additional TGF-$β_1$ nucleic acid and protein sequences, including TGF-β variants that retain TGF-$β_1$ biological activity (such as those variant sequences having at least 80%, at least 90%, at least 95%, at least 98%, or at least 99% sequence identity to these publicly available sequences or having such amounts of identity to a mature form of TGF-$β_1$).

Treating a disease: "Treatment" refers to a therapeutic intervention that ameliorates a sign or symptom of a disease or pathological condition (for instance, fibrosis) after it has begun to develop. "Prevention" refers to inhibiting the full development of a disease, for example in a person who is known to have a predisposition to a disease such as a person who has been or is at risk for developing fibrosis of the liver, pancreas or kidney.

Vitamin D: A group of fat-soluble secosteroid prohormones and hormones, the two major forms of which are vitamin D2 (ergocalciferol) and vitamin D3 (cholecalciferol), which are converted to 1α, 25 dihydroxyvitamin $D_3$ (1α, 25-$(OH)_2$-D3), also known as calcitriol, the physiologically active form of vitamin D.

Vitamin D agonist or analog: Any compound, synthetic or natural, that binds to and activates the VDR, such as a VDR ligand (e.g., calcitriol), VDR agonist precursor, vitamin D analogs, vitamin D precursors.

Specific, non-limiting examples of natural and synthetic vitamin D agonists and analogs include 1α,25$(OH)_2D_3$, calcipotriol, LG190090, LG9190119, LG190155, LG190176, and LG190178 (see, for instance, Boehm et al., (1999) *Chemistry & Biology*, 6:265-275); LY2108491, and LY2109866 (Ma et al., (2006) *J Clin. Invest.*, 116:892-904); 2β-(β-Hydroxypropoxy) 1α,25-Dihydroxyvitamin $D_3$ (ED-71) (Tsurukami et al., (1994) *Calcif Tiss. Int.* 54:142-149); EB 1089 (Pepper et al., (2003) *Blood*, 101:2454-2460); OCT(22-oxa-calcitrol) (Makibayashi et al., (2001) *Am. J. Path.*, 158:1733-1741); (laOH-2,19-nor-25hydroxyvitamin$D_3$) and (1,3-Deoxy-2-CHCH$_2$OH-19-nor-25-hydroxyvitaminD3) (Posner et al., (2005) Bioorganic & Medicinal Chemistry, 13:2959-2966) and any of the vitamin D analogs disclosed in Rey et al., (1999) *J. Organic Chem.*, 64:3196-3206; and bile acid derivatives such as lithochoic acid (LCA) and ursodoxycholic acid (UDCA) (see, for instance, Nehring et al., (2007) *PNAS*, 104:10006-10009; Makishima et al., (2002) *Science*, 296:1313-1316; Copaci et al., (2005) *Rom. J. Gastroenterol.*, 14:259-266). Each of these references is hereby incorporated by reference in its entirety.

Vitamin D precursor: Any compound capable of being converted to an agonist of the vitamin D receptor by an enzyme. In certain, non-limiting examples, that enzyme is CYP27B1. Specific, non-limiting examples of vitamin D precursors include vitamin $D_3$ (cholecalciferol), 25-hydroxy-vitamin $D_3$ (25-OH-$D_3$) (calcidiol), as well as vitamin D2 (ergocalciferol) and its precursors.

Vitamin D receptor (VDR): A member of the nuclear hormone receptor (NHR) superfamily and is a key regulator of calcium homeostasis and skeletal health (Bouillon et al., 2008; Goltzman et al., 2004). VDR possesses the common nuclear receptor structure, for example, is comprised of an N-terminal activation domain, a DNA-binding region (DBD) with two zinc finger domains, a hinge region and a ligand-binding domain (LBD). VDR activated gene transcription requires initial nuclear translocation via importin-α, heterodimerization with RXR, and binding to response elements present in target genes. VDR regulates genes associated with the maintenance of calcium and phosphate homeostasis in the intestine and kidney. The signal initiated by VDR/RXR heterodimers is modulated by the association of co-activating or co-repressing proteins and also depends on other signaling partners in the nuclear compartment. The VDR/RXR heterodimer is non-permissive, in that the presence or absence of RXR ligands is not known to affect VDR responses.

The closest structural and functional relatives of VDR within the NHR superfamily include farnesoid X receptor (FXR), constitutive androstane receptor (CAR) and pregnane X receptor (PXR), all of which are regulators of bile acid homeostasis and xenobiotic detoxification in the liver (Bookout et al., 2006; Bouillon et al., 2008).

The endogenous activators of VDR include the biologically active form of vitamin D ($1\alpha,25(OH)_2D3$ (calcitriol)) and bile acids such as lithocholic acid (LCA) and its derivatives (LCA-acetate, LCA-formate, 3-keto LCA) (Makishima et al., 2002; Nagpal et al., 2005).

Overview

Liver fibrosis is a reversible wound-healing response involving $TGF\beta1$ activation of hepatic stellate cells (HSCs). It is shown herein that vitamin D receptor (VDR) ligands inhibit HSC activation and abrogate liver fibrosis, while Vdr knockout mice spontaneously developed hepatic fibrosis. Mechanistically, a pronounced redistribution of genome wide VDR binding sites (VDR cistrome) in HSCs elicited by a $TGF\beta1$ pro-fibrotic insult is shown. This $TGF\beta1$-induced VDR cistrome overlaps extensively with SMAD3 binding sites, with co-occupancy at numerous cis-regulatory elements identified on a large set of pro-fibrotic genes. Addition of VDR ligand reduces SMAD3 occupancy at co-regulated genes, revealing an intersecting VDR/SMAD genomic circuit that regulates hepatic fibrogenesis. These results provide a role for VDR as an endocrine checkpoint to modulate the wound healing response in liver, and indicate VDR ligands as a therapy for liver fibrosis, as well as fibrosis of other organs such as the kidney and pancreas.

The establishment of HSCs as the primary effector cell for the deposition of ECM in normal and fibrotic liver in the early 1990s was a milestone discovery in understanding the pathogenesis of hepatic fibrosis (Friedman, 1993). Since then, a wide spectrum of cellular signaling molecules, hormones, cell membrane receptors and transcription factors in HSCs have been investigated and found to promote hepatic fibrogenesis (Hernandez-Gea and Friedman, 2011). However, the factors and signaling cascades that actively prevent this pathological process are poorly understood.

Figure 14A:
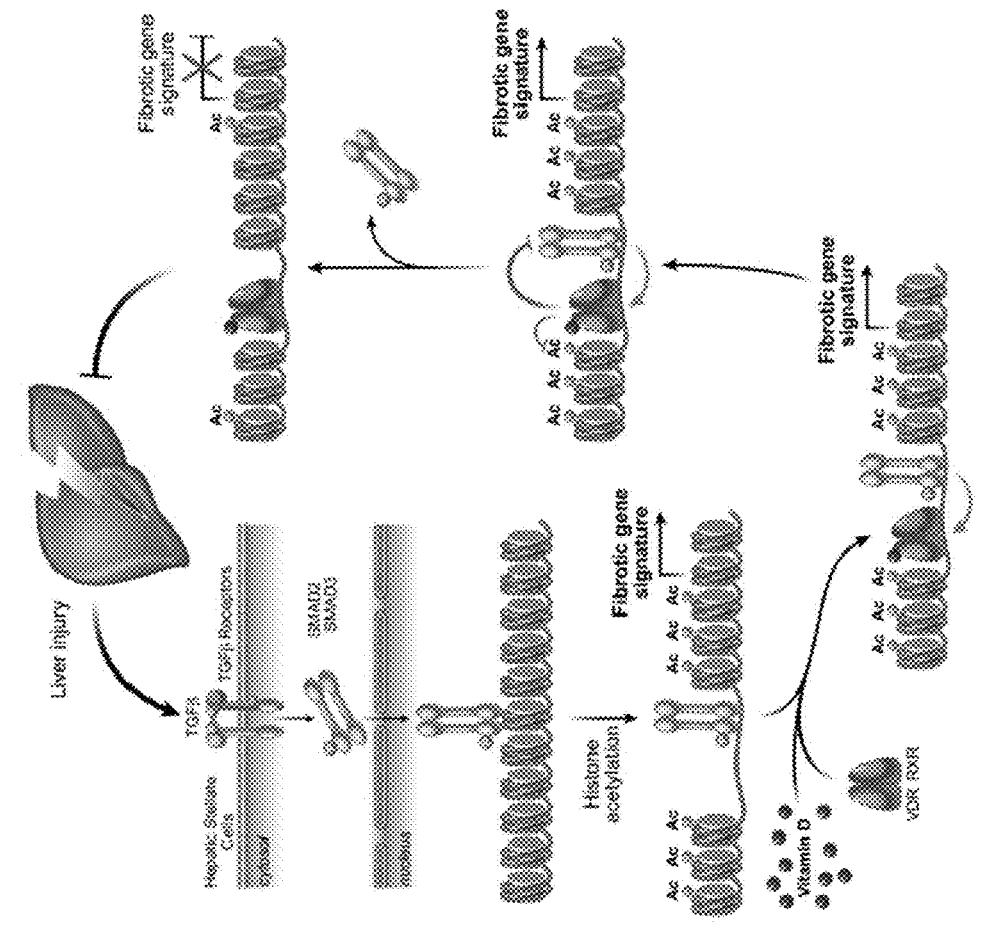
Figure 14B:
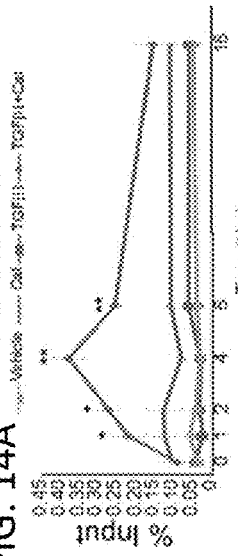
Figure 14C:
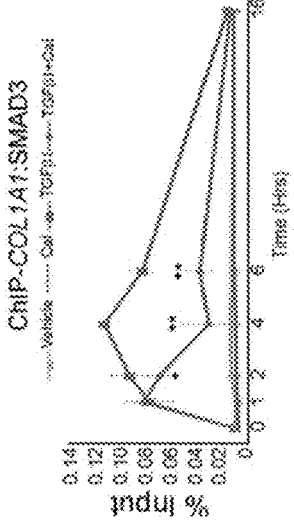
Figure 14D:
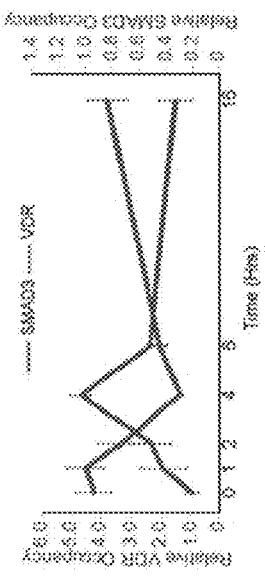

Here, it is shown that pharmacological activation of VDR attenuates the progression of liver fibrosis in an experimental animal model while genetic abrogation of VDR expression results in the spontaneous development of liver fibrosis, thus implicating VDR in an endocrine checkpoint that negatively modulates the wound healing response in liver. Mechanistically a previously unrecognized and temporally controlled genomic circuit composed of the opposing action of VDR and SMAD transcription factors that is able to restrain the intensity of the fibrogenic response in HSCs and govern fibrogenesis in liver is provided. Specifically, in response to liver injury, HSC activation by $TGF\beta1$ induces pro-fibrotic gene expression via SMAD translocation to the nucleus and chromatin remodeling. By increasing accessibility to adjacent vitamin D response elements (VDREs), SMAD activation facilitates VDR recruitment to previously cryptic genomic sites. Liganded VDR subsequently antagonizes SMAD residency on chromatin and compromises acetylation of histone H3 to ultimately suppress pro-fibrotic gene expression (FIG. 14D). Notably, the proximal location of nearly 10,500 $TGF\beta1$-induced SMAD and VDR binding sites identifies a global chromatin architecture and indicates that the integrated VDR/SMAD genomic circuit functions as a master regulator of the hepatic fibrotic response.

The identification of a chromatin basis for inhibiting $TGF\beta$ signaling places a direct focus on SMAD-dependent transcription as a regulatory target. This is relevant as $TGF\beta$-SMAD signaling plays an essential role in almost every aspect of metazoan biology and its dysregulation can result in a diversity of human diseases ranging from autoimmunity to fibrosis and cancer (Hernandez-Gea and Friedman, 2011; Li and Flavell, 2008; Massague, 2008). This finding of genomic antagonism between VDR and SMAD not only establishes VDR as the first DNA-binding transcription factor that attenuates $TGF\beta$-SMAD signaling at a chromatin interface but also adds specificity (a cistromic layer) for the more general concept of 'transcriptional crosstalk'.

The observation that $TGF\beta$-SMAD activation enables subsequent recruitment of ligand-bound VDR to repress SMAD targets reveals a means by which two endogenous signaling pathways can cross-regulate each other's activity. Thus, this genomic relay allows positive activation by SMAD to be subsequently inhibited by VDR and thus constitutes a self-adjusting genomic circuit, which is highly distinguishable from the previously reported genomic crosstalk between transcription factors in a mutually exclusive manner (Barish et al., 2010; Hua et al., 2009). This circuit may confer on HSCs the ability to orchestrate ECM synthesis in both the normal and fibrotic liver.

In addition to the $TGF\beta$-SMAD pathway, fibrosis is almost always preceded by persistent inflammation clinically (Hernandez-Gea and Friedman, 2011; Lee and Friedman, 2011). Hence, a broader anti-inflammatory role for VDR signaling may contribute to its anti-fibrotic property in liver. In this regard, VDR has been documented for its expression in several cell types central to the inflammatory response (Barish et al., 2005; Griffin et al., 2001; von Essen et al., 2010), and both vitamin D deficiency and polymorphisms of VDR itself as well as genes involved in vitamin D metabolism have been linked to both risk and severity of inflammatory diseases (Agmon-Levin et al., 2012; Janssens et al., 2011; Munger et al., 2006; Ramagopalan et al., 2011). However, the role of VDR signaling's anti-inflammatory action in the context of hepatic fibrogenesis is less clear. On one hand, the dysregulated inflammatory response coupled with the spontaneous development of liver fibrosis in $Vdr^{-/-}$ mice indicates that VDR signaling might control hepatic fibrogenesis through an anti-inflammatory mechanism (FIG. 3H, right). On the other hand, this notion is blunted by the modest peri-sinusoidal liver fibrosis phenotype without any inflammatory response found in $Vdr^{+/-}$ mice (FIG. 3H, center). Furthermore, the causable relationship between inflammation and fibrosis remains to be fully established and the major pro-fibrogenic role of inflammation during hepatic fibrogenesis appears to be to sensitize HSCs for $TGF\beta$-SMAD activation (Seki et al., 2007; Seki and Schnabl, 2012). Therefore, the anti-inflammatory property of VDR signaling may not play a major role in its anti-fibrotic function.

The results herein clarify an unappreciated function of VDR signaling in liver pathophysiology. Due to its exceptionally low expression, VDR has received much less attention than its highly expressed cognate clade members that include FXR, PXR and CAR that impact nearly every aspect of hepatic function including lipid and glucose metabolism, drug disposition, cholesterol efflux and bile acid homeostasis (Bookout et al., 2006; Chawla et al., 2001). However, recent studies showing that low vitamin D levels are linked to increased hepatic fibrosis in patients with chronic liver disease (Abramovitch et al., 2011; Lim and Chalasani, 2012; Petta et al., 2010; Terrier et al., 2011) and that vitamin D can inhibit liver fibrosis in rats (Abramovitch et al., 2011) indicate a potential physiologic role for hepatic VDR. However, whether and how VDR directly or indirectly regulates hepatic fibrogenesis remained unresolved. The observations herein that VDR promotes HSC quiescence and controls TGFβ signaling identify a new mechanism through which vitamin D can exert its anti-fibrotic effects. These results are consistent with studies suggesting that a polymorphism in VDR is correlated with increased progression of liver fibrosis and evolution of cirrhosis (Baur et al., 2011; Tanaka et al., 2009).

Up to 45% of deaths in the developed world can be attributed to fibrotic diseases, yet few anti-fibrotic drugs are currently approved for clinical use (Wynn, 2008). Though therapies designed to neutralize TGFβ show broad anti-fibrotic activity (Rosenbloom et al., 2010) the benefits are compromised by unnecessarily blocking TGFβ in non-diseased tissue. The identification of the VDR/SMAD genomic circuit provides a safer anti-fibrotic strategy by restricting TGFβ inhibition to VDR-positive cells instead of perturbing signaling body-wide.

In summary, the results herein provide an intersecting genomic circuit comprising VDR and SMAD transcription factors that governs hepatic fibrogenesis. This finding extends the understanding of how two distinct signal-dependent transcription factors interact with each other to establish cell identity and function. Through the use of genetic and inducible models, new insight is provided into how global programs responding to TGFβ1 signaling are established and regulated. Furthermore, these studies establish VDR as a drug target to treat liver fibrosis and provide a new paradigm of VDR-dependent gene expression regulation. Given the ubiquitous expression patterns of VDR and TGFβ, the VDR/SMAD genomic circuit is applicable to many other cell types which can impact the pathogenesis of a wide range of human diseases.

Based on these findings, provided herein are compositions that include a nanoparticle and a compound that increases the biological activity of a vitamin D receptor (VDR) (referred to herein as a VDR agonist). For example, such compositions can include two or more different types of nanoparticles and/or two or more different VDR agonists. In one example, the nanoparticle is or includes a lipid nanoparticle and/or a polymeric nanoparticle. The disclosed compositions can further include other therapeutic agents, such as a chemotherapeutic (e.g., gemcitabine), a biologic (e.g., monoclonal antibody), or combinations thereof. In some examples, the composition includes a pharmaceutically acceptable carrier.

In one example, the nanoparticles include agents on their surface to target to a cell of interest, such as a stellate cell (such as a hepatic, renal, pancreatic, heart or lung stellate cell). In one example the nanoparticles include on their surface one or more of albumin, retinol binding protein, mannose-6-phosphate modified albumin (e.g., see Li et al., *J. Pharm. Pharmacol.* 2009, 61(9):1155-61, herein incorporated by reference, for example to target the nanoparticle to a hepatic stellate cell), a fatty acid ester, or a retinyl ester (e.g., retinyl palmitate). In one example albumin is serum albumin (such as human [OMIM 103600, e.g., GenBank® Accession No. NP_000468.1] or bovine [e.g., GenBank® Accession No. NP_851335]). In another example, albumin is from chicken egg white. Albumin is commercially available, for example from Sigma-Aldrich (e.g., catalog numbers A2153, 05470, A9731, and A5503). In some examples, the albumin is modified to include mannose 6-phosphate. Retinol binding proteins (RBP) that can be used with the nanoparticles include those that are publically available, for example from the GenBank® sequence database (e.g., Accession Nos. AAA59188.1, AAB06955.1, CAA24959.1, and AAA42018.1, as well as RBP variants that retain RBP biological activity, such as those variant sequences having at least 80%, at least 90%, at least 95%, at least 98%, or at least 99% sequence identity to these publicly available sequences or having such amounts of identity to a mature form of RBP). Any methods known in the art can be used to attach such molecules to a nanoparticle.

In some examples, the nanoparticles is at least 1 nm in diameter, such as at least 10 nm, at least 100 nm, or at least 500 nm, such as 1 to 1000 nm, 10 to 1000 nm, 50 to 500 nm, or 100 to 500 nm.

For example, in some examples the compound that increases the biological activity of VDR (or composition containing such) can increase the biological activity of the VDR by at least 25%, at least 50%, at least 75%, at least 90%, at least 95%, at least 100%, at least 200%, at least 300%, at least 400% or at least 500%, as compared to the biological activity in the absence of the compound. In some examples, the biological activity of the VDR that is increased is one or more of storage of vitamin A, vitamin D and/or lipids by a cell (for example by reducing release of such agents). Thus for example, the compound that increases the biological activity of VDR (or composition containing such) increases by at least 25%, at least 50%, at least 75%, at least 90%, at least 95%, at least 100%, at least 200%, at least 300%, at least 400% or at least 500%, storage of vitamin A, vitamin D and/or lipids by a cell as compared to the storage in the absence of the compound. In some examples, the compound that increases the biological activity of VDR (or composition containing such) reduces release of vitamin A, vitamin D and/or lipids by a cell by at least 50%, at least 75%, at least 90%, at least 95%, at least 98%, or at least 99% as compared to the release in the absence of the compound. In some examples, the compound that increases the biological activity of VDR (or composition containing such) increases the biological activity of the VDR in a stellate cell, an epithelial cell, or both. Examples of such cells include pancreatic stellate cells, kidney stellate cells, hepatic stellate cells, heart stellate cells, and lung stellate cells.

Examples of VDR agonists include but are not limited to: vitamin D, a vitamin D precursor, a vitamin D analog, a vitamin D receptor ligand, a vitamin D receptor agonist precursor, or combinations thereof. Specific examples of VDR agonists include but are not limited to calcipotriol, 25-hydroxy-$D_3$ (25-OH-$D_3$) (calcidiol); vitamin D3 (cholecalciferol); vitamin D2 (ergocalciferol), 1α,25-dihydroxyvitamin $D_3$ (calcitriol), or combinations thereof.

Also provided are methods of using the disclosed compositions. In one example, methods are provided for increasing or retaining vitamin A, vitamin D, and/or lipid in an epithelial or stellate cell. Such methods can include contacting a therapeutically effective amount of a composition provided herein with an epithelial and/or stellate cell, thereby increasing or retaining vitamin A, vitamin D, and/or lipid in the epithelial and/or stellate cell. Such methods can be performed in vitro or in vivo. For example, the epithelial or stellate cell can be in a subject, and contacting can include administering a therapeutically effective amount of the composition to the subject, thereby increasing or retaining vitamin A, vitamin D, and/or lipid in the epithelial or stellate cell. In some examples, such methods treat a disease, such as a liver disease, kidney disease, or pancreatic disease in the subject. Examples of liver diseases that can be treated using the disclosed methods include one or more of alcohol liver disease, fatty liver disease, liver fibrosis/cirrhosis, biliary fibrosis/cirrhosis, liver cancer, hepatitis B virus infection, hepatitis C virus infection, sclerosing cholangitis, Budd-Chiari syndrome, jaundice, nonalcoholic steatohepatitis, hemochromatosis, and Wilson's disease. In some examples the liver cancer is a hepatocellular carcinoma, cholangiocarcinoma, angiosarcoma, or hemangiosarcoma. Examples of pancreatic diseases that can be treated with the disclosed methods include but are not limited to pancreatic fibrosis and pancreatic ductal adenocarcinoma (PDA). In some examples, the kidney disease is fibrosis of the kidney.

The disclosure also provides methods of reducing binding of SMAD3 to genomic enhancer elements of the VDR coregulated pro-fibrotic genes. Such methods can include contacting a therapeutically effective amount of a composition provided herein (such as one that includes a nanoparticle and VDR against) with an epithelial and/or stellate cell, thereby reducing binding of SMAD3 on genomic enhancer elements of co-regulated pro-fibrotic genes on the epithelial and/or stellate cell. In some examples the composition reduces binding of SMAD3 on genomic enhancer elements of co-regulated pro-fibrotic genes by at least 25%, at least 50%, at least 75%, at least 90%, at least 95%, or at least 99%, as compared to the biological activity in the absence of the composition.

The disclosure also provides methods of increasing expression of VDR in stellate cells (such as pancreatic stellate cells, kidney stellate cells, hepatic stellate cells, heart stellate cells, or lung stellate cells). Such methods can include contacting the stellate cell with an amount of a VDR agonist that is part of a nanoparticle sufficient to enhance binding of VDR agonist to the VDR by at least 10-fold, at least 20-fold, at least 50-fold, or at least 100-fold.

Also provided are methods for screening for an agent that can treat fibrosis, such as fibrosis of the liver, pancreas, or kidney. In particular examples, the method includes contacting a hepatic, renal, lung, heart, kidney, or pancreatic stellate cell with one or more test agents and optionally TGF-β1. Subsequently, one or more of VDR agonist produced by the cell, production or expression of CYP24A1 by the cell, production, post-translational modification, or expression of SMAD3 by the stellate cell, and binding of VDR ligands to the VDR, is detected. Test agents that increase production of a VDR agonist by the cell by at least 5-fold (such as at least 6-fold, at least 8-fold, or at least 10-fold) relative to the absence of the one or more test agents, increase production or expression of CYP24A1 by the cell by at least 1.5-fold (such as at least 6-fold, at least 8-fold, or at least 10-fold) relative to the absence of the one or more test agents, reduce production, post-translational modification, or expression of SMAD3 by the cell by at least 5-fold (such as at least 6-fold, at least 8-fold, or at least 10-fold) relative to the absence of the one or more test agents, or combinations thereof, wherein the selected test agents are agents that can treat fibrosis. In some examples, the selected test agents enhance binding of VDR to the VDR agonist by at least 10-fold, at least 20-fold, at least 50-fold, or at least 100-fold. The screening methods can further include determining whether the one or more selected test agents have hypercalcemic effects in vitro or in vivo. In some examples, the method also includes selecting test agents that did not have hypercalcemic effects in vitro, in vivo, or both.

In some examples, the screening methods further include testing in vivo. For example, the method can include administering one or more of the selected test agents to a mammal having fibrosis (such as an animal model of liver, pancreatic, or kidney fibrosis); and determining whether the one or more test agents treat or prevent the fibrosis (such as decreases fibrosis by at least 25%, at least 50%, at least 75%, at least 90%, at least 95%, or at least 99%, increases vitamin A, vitamin D, lipid storage in a stellate and/or epithelial cell by at least 25%, at least 50%, at least 75%, at least 90%, at least 95%, at least 100%, at least 2-fold, at least 3-fold, at least 5-fold, or at least 10-fold, or combinations thereof, relative to such amounts in the absence of administration of the selected test agents). In some examples, the method also includes selecting test agents that treated the fibrosis.

Compositions Containing Nanoparticles and VDR Agonist

The present disclosure provides compositions that include a nanoparticle and a compound that increases the biological activity of the VDR, that is, a VDR agonist such as vitamin D, a vitamin D precursor, a vitamin D analog, a vitamin D receptor ligand, a vitamin D receptor agonist precursor, or combinations thereof. Such compositions can include additional agents, such as one or more pharmaceutically acceptable carriers, other therapeutic agents, or combinations thereof. In one example, the compositions further include a chemotherapeutic (such as gemcitabine), a biologic (such as a therapeutic antibody), or combinations thereof. Specific examples of VDR agonists that can be used include, but are not limited to: calcipotriol, 25-hydroxy-$D_3$ (25-OH-$D_3$) (calcidiol); vitamin D3 (cholecalciferol); vitamin D2 (ergocalciferol), 1α,25-dihydroxyvitamin $D_3$ (calcitriol), and combinations thereof. The VDR agonist can be in the nanoparticle or attached to the nanoparticle surface.

Examples of nanoparticles that can be used in the disclosed compositions include, but are not limited to those provided in US Publication Nos. 20130287688, 20130287857, 20100233251, 20100092425, 20120027808, 20080226739, and 20050215507 and U.S. Pat. Nos. 7,427,394, 8,343,497, 8,562,998, 7,550,441, 7,727,969, 8,343,498, and 8,277,812, all herein incorporated by reference. In some examples the nanoparticle is a lipid or polymeric nanoparticle. In one example the nanoparticles include on their surface one or more of albumin, retinol binding protein, mannose-6-phosphate modified albumin (e.g., see Li et al., *J. Pharm. Pharmacol.* 2009, 61(9):1155-61), a fatty acid ester, or a retinyl ester (e.g., retinyl palmitate). The nanoparticles can also include a linear-dendritic hybrid polymer for encapsulating biologically active materials, comprising: a ligand for a predetermined target (e.g., a ligand for a stellate cell (such as one residing in the lung, liver, kidney, heart or pancreas), a VDR agonist, or combinations thereof); a dendron; and a polyethylene glycol (PEG) chain linking the ligand to the dendron. In some examples, the nanoparticle is between about 0.1 nm and 5000 nm in diameter, such as 1-100 nm, 0.1-1 nm, 5-20 nm, 5-15 nm, 10-5,000 nm, 20-1,000 nm, 10-500 nm, 10-200 nm, 10-150 nm, 10-100 nm, 10-25 nm, 20-40 nm, or 10, 15, 20, 25, 35, 45, 50, 75, 100, 150 or 200 nm in diameter.

The biological activity of VDR that can be increased by the disclosed compositions can include reducing the release of vitamin A from a cell, release of vitamin D from a cell, release of lipids from a cell, or combinations thereof. In some examples, the cell is a stellate cell (such as a pancreatic, kidney or hepatic stellate cell), an epithelial cell, or both. For example, in response to injury or stress, vitamins A and D and lipids can be released from an activated cell (such as an activated epithelial or stellate cell), which can result in other injury, such as fibrosis. Thus, in order to reduce these other injuries, such as fibrosis, the function of VDR can be increased to revert the cell to a quiescent state.

A composition that includes a nanoparticle and a compound that increases the biological activity of the VDR (e.g., a VDR agonist) can increase VDR activity by at least 20%, at least 25%, at least 40%, at least 50%, at least 75%, at least 80%, at least 90%, at least 95%, at least 100%, at least 200%, at least 300%, at least 400%, or even in some examples at least 500%. Thus in one example, a composition that includes a nanoparticle and a compound that increases the biological activity of the VDR can reduce the release of vitamin A from a cell (such as a stellate or epithelial cell) by at least 10%, at least 20%, at least 25%, at least 40%, at least 50%, at least 75%, at least 80%, at least 90%, or at least 95%, as compared to an absence of the composition. In one example, a composition that includes a nanoparticle and a compound that increases the biological activity of the VDR can reduce the release of vitamin D from a cell (such as a stellate or epithelial cell) by at least 10%, at least 20%, at least 25%, at least 40%, at least 50%, at least 75%, at least 80%, at least 90%, or at least 95%, as compared to an absence of the composition. In one example, a composition that includes a nanoparticle and a compound that increases the biological activity of the VDR can reduce the release of lipids from a cell (such as a stellate or epithelial cell) by at least 10%, at least 20%, at least 25%, at least 40%, at least 50%, at least 75%, at least 80%, at least 90%, or at least 95%, as compared to an absence of the composition.

In some examples, a composition that includes a nanoparticle and a compound that increases the biological activity of the VDR can increase the retention or storage of vitamin A by a cell (such as a stellate or epithelial cell) by at least 10%, at least 20%, at least 25%, at least 40%, at least 50%, at least 75%, at least 80%, at least 90%, or at least 95%, as compared to an absence of the composition. In one example, a composition that includes a nanoparticle and a compound that increases the biological activity of the VDR can increase the retention or storage of vitamin D by a cell (such as a stellate or epithelial cell) by at least 10%, at least 20%, at least 25%, at least 40%, at least 50%, at least 75%, at least 80%, at least 90%, or at least 95%, as compared to an absence of the composition. In one example, a composition that includes a nanoparticle and a compound that increase the biological activity of VDR can increase the retention or storage of lipids by a cell (such as a stellate or epithelial cell) by at least 10%, at least 20%, at least 25%, at least 40%, at least 50%, at least 75%, at least 80%, at least 90%, or at least 95%, as compared to an absence of the composition.

Methods of measuring vitamin A, vitamin D, and lipid in a cell are known and are provided herein, and such assays can be used to determine if a compound increases VDR activity and thus can be used in the compositions provided herein. Exemplary methods for measuring vitamin A in a cell are provided in Vogel et al. (*J. Lipid Res.* 41(6):882-93, 2000) and methods for measuring vitamin D in a cell are provided in Blum et al. (*Endocrine.* 33(1):90-4, 2008). In one example, the ability of a compound or composition to revert a cell, such as a stellate cell, to a quiescent state can be determined by staining the cell in the presence and absence of the compound/composition (for example before and after contact with the compound/composition) with BODIPY® fluorescent dye which binds neutral lipid. Quiescent cells are characterized by cytoplasmic lipid droplets, which are lost in the activated cell state and accumulate upon treatment of activated cells with drugs such as a compound that increases the biological activity VDR, which induce quiescence. Thus, treatment of activated cells followed by BODIPY® staining and fluorescence measurements can be used to identify compounds that increase the biological activity of a VDR which drive cells (such as stellate cells) toward quiescence.

Exemplary VDR Agonists

The disclosed compositions include one or more VDR agonists (such as a VDR ligand) that can bind to and activate the VDR, for example to prevent or attenuate the processes of injury, inflammation, and fibrogenesis in the liver, pancreas and/or kidney. VDR agonists include but are not limited to $1\alpha,25(OH)_2$-D3 and precursors and analogs thereof, VDR ligands, and VDR agonist precursors. The disclosure is not limited to particular vitamin D agonists. A variety of biologically active vitamin D agonists are contemplated. Exemplary agents are known in the art.

In some examples, $1\alpha,25(OH)_2D_3$ or a vitamin D precursor or analog is used as a VDR agonist. It is not necessary to use the most biologically active form of vitamin D to achieve a beneficial therapeutic effect. The naturally occurring ligand of the vitamin D receptor is calcitriol. In one embodiment, precursors of calcitriol (such as calcidiol) are administered to a subject, and are then converted within the target cell population to calcitriol.

In addition, HSCs express CYP24A1, a cytochrome P450 enzyme that terminates the biological effect of calcitriol by side chain hydroxylation. Thus, in one embodiment, a VDR ligand or other VDR agonist or agonist precursor that is resistant to deactivation by CYP24A1 is used to achieve more effective and longer lasting VDR activation in target cell populations. In specific examples, the VDR ligand is one that can be activated by CYP27B1 while being resistant to deactivation by CYP24A1. This permits VDR activation in target cell populations in the liver (for example, HSCs), pancreas and kidney, while minimizing undesirable systemic effects on calcium homeostasis.

In one example a VDR agonist or precursor thereof exhibits the property of high first-pass hepatic clearance due to extensive hepatic metabolism. A molecule with this property, when administered orally, is absorbed and transported to the liver via the portal vein. In the liver, the molecule activates VDR in cell populations such as hepatic stellate cells, Kupffer cells and sinusoidal endothelial cells while exhibiting minimal systemic effects on calcium homeostasis due to low systemic bioavailability.

VDR agonists that can be used include those molecules that activate the VDR. Methods of determining if an agent is a VDR agonist are routine. For example, induction of CYP24A1 expression can be measured in cells that expressing VDR contacted with the agent, wherein an increase in CYP24A1 expression (such as a 10- to 20-fold increase in expression) indicates that the agent is a VDR agonist. Other methods include transfected reporter gene constructs and FRET assays. In some example, binding of an agonist to a purified LBD is detected by measuring induced recruitment for coactivator peptides (e.g., LXXLL). For example VDR agonists can increase CYP24A1 expression in a VDR-expressing cell by at least 20%, at least 50%, at least 75%, at least 80%, at least 90% at least 100%, at least 200% or even at least 1000% or more as compared to the absence of the agonist.

VDR agonists include vitamin D compounds, precursors and analogs thereof. Vitamin D compounds include, but are not limited to compounds which have at least one of the following features: the C-ring, D-ring and 3β-hydroxycyclohexane A-ring of vitamin D interconnected by the 5,7 diene double bond system of vitamin D together with any side chain attached to the D-ring (e.g., compounds with a 'vitamin D nucleus' and substituted or unsubstituted A-, C-, and D-rings interconnected by a 5,7 diene double bond system typical of vitamin D together with a side chain attached to the D-ring).

Vitamin D analogs include those nonsecosteroid compounds capable of mimicking various activities of the secosteroid calcitriol. Examples of such compounds include, but are not limited to, LG 190090, LG190119, LG190155, LG190176, and LG1900178 (See, Boehm et al., *Chemistry & Biology* 6:265-275, 1999).

Vitamin D compounds include those vitamin D compounds and vitamin D analogs which are biologically active in vivo, or are acted upon in a mammalian subject such that the compound becomes active in vivo. Examples of such compounds include, but are not limited to: vitamin D, calcitriol, and analogs thereof [e.g., 1α-hydroxyvitamin $D_3$ (1α-OH-$D_3$), 1,25-dihydroxyvitamin $D_2$ (1,25-$(OH)_2D_2$), 1α-hydroxyvitamin $D_2$ (1α-OH-$D_2$), 1α,25-$(OH)_2$-16-ene-$D_3$, 1α,25-$(OH)_2$-24-oxo-16-ene-$D_3$, 1α,24R$(OH)_2$-$D_3$, 1α,25$(OH)_2$-22-oxa-$D_3$, 20-epi-22-oxa-24a,24b,-dihomo-1α,25$(OH)_2$-$D_3$, 20-epi-22-oxa-24a,26a,27a,-trihomo-1α25$(OH)_2$-$D_3$, 20-epi-22-oxa-24homo-1α,25$(OH)_2$-$D_3$, 1,25-$(OH)_2$-16,23E-diene-26-trifluoro-19-nor-$D_3$, and nonsecosteroidal vitamin D mimics.

In one example, the VDR agonist is one or more of the following vitamin D, 1,α25 dihydroxyvitamin $D_3$, calcipotriol, 1α-hydroxyvitamin $D_3$, 1,25-dihydroxyvitamin $D_2$, 1α-hydroxyvitamin $D_2$, 1α,25-$(OH)_2$-16-ene-$D_3$, 1α,25-$(OH)_2$-24-oxo-16-ene-$D_3$, 1α,24R$(OH)_2$-$D_3$, 1α,25$(OH)_2$-22-oxa-$D_3$, 20-epi-22-oxa-24a,24b,-dihomo-1α,25$(OH)_2$-$D_3$, 20-epi-22-oxa-24a,26a,27a,-trihomo-1α25$(OH)_2$-$D_3$, 20-epi-22-oxa-24homo-1α,25$(OH)_2$-$D_3$, and 1,25-$(OH)_2$-16,23E-diene-26-trifluoro-19-nor-$D_3$.

In a one embodiment, the biologically active vitamin D compound is selected from 1,α25-dihydroxyvitamin $D_3$, 19-nor-1,25-dihydroxyvitamin $D_2$, 19-nor-1,25-dihydroxy-21-epi-vitamin $D_3$, 1,25-dihydroxy-24-homo-22-dehydro-22E-vitamin $D_3$, and 19-nor-1,25-dihydroxy-24-homo-22-dehydro-22E-vitamin $D_3$, and nonsecosteroidal vitamin D mimics. In an additional example, the biologically active VDR agonist is selected from the analogs represented by the following formula:

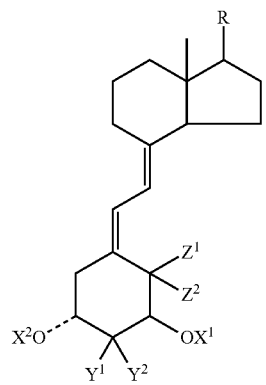

wherein $X^1$ and $X^2$ are each selected from the group consisting of hydrogen and acyl;

wherein $Y^1$ and $Y^2$ can be H, or one can be O-aryl or O-alkyl while the other is hydrogen and can have a β or α configuration, $Z^1$ and $Z^2$ are both H, or $Z^1$ and $Z^2$ taken together are $CH_2$; and wherein R is an alkyl, hydroxyalkyl or fluoroalkyl group, or R may represent the following side chain:

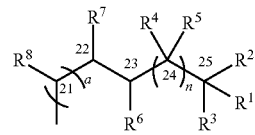

wherein (a) may have an S or R configuration and wherein $R^1$ represents hydrogen, hydroxy or O-acyl, $R^2$ and $R^3$ are each selected from the group consisting of alkyl, hydroxyalkyl and fluoroalkyl, or, when taken together represent the group —$(CH_2)_m$— where m is an integer having a value of from 2 to 5, $R^4$ is selected from the group consisting of hydrogen, hydroxy, fluorine, O-acyl, alkyl, hydroxyalkyl and fluoroalkyl, $R^5$ is selected from the group consisting of hydrogen, hydroxy, fluorine, alkyl, hydroxyalkyl and fluoroalkyl, or, $R^4$ and $R^5$ taken together represent double-bonded oxygen, $R^6$ and $R^7$ taken together form a carbon-carbon double bond and $R^8$ may be H or $CH_3$, and wherein n is an integer having a value of from 1 to 5, and wherein the carbon at any one of positions 20, 22, or 23 in the side chain may be replaced by an O, S, or N atom.

In one example, the VDR agonists used in the methods provided herein do not cause symptoms of hypercalcemia when administered to a subject. In another example, the VDR agonists do not generate as much (i.e., a lesser degree) of a calcemic response as compared to calcitriol when administered to a subject. In one example, VDR agonists have low calcemic response characteristics as compared to calcitriol. In another embodiment, these compounds are selected from 1α,25-$(OH)_2$-24-epi-$D_2$, 1α,25-$(OH)_2$-24a-Homo-$D_3$, 1α,25-$(OH)_2$ 24a-Dihomo-$D_3$, 1α,25-$(OH)_2$-19-nor-$D_3$, and 20-epi-24-homo-1α,25-$(OH)_2$-$D_3$.

Other exemplary VDR agonists that can be used are provided in Tables 1A and 1B.

TABLE 1A 1,25-(OH)$_2$D$_3$ and its synthetic analogs (taken from Nagpal et al., *Endocr. Rev.* 2005; 26:662-687).
Vitamin D Analogs

| Compound | R | Compound | R |
|---|---|---|---|
| 1α,25-(OH)$_2$D$_3$ (Calcitriol) | | 1α,25-(OH)$_2$-22,24-diene-24a,26a,27a-trihomo-D$_3$ (EB 1089) | |
| 1α-(OH)D$_3$ (Alfacalcidol) | | 1α-25-(OH)$_2$-22-ene-25-oxa-D$_3$ (ZK 156718) | |
| 1α,24-(OH)$_2$-24-cyclopropyl-D$_3$ (Calcipotriol) | | 25-(4-methylthiazol-2-yl)-calcipotriol (ZK 191732) | |
| 1α-25-(OH)$_2$-22-oxa-D$_3$ (Maxacalcitol) | | 1α,24R-(OH)$_2$D$_3$ (Tacalcitrol) | |

1α,25-(OH)$_2$D$_3$ (Calcitriol)

ED-71 [1α,25-(OH)$_2$-2β-(3-hydroxypropyl)D$_3$)

TABLE 1B 1,25-(OH)₂D₃ and its synthetic analogs (taken from Nagpal et al., *Endocr. Rev.* 2005; 26:662-687).
"20-Epi Vitamin D Analogs"

| Compound | R | Compound | R |
|---|---|---|---|
| 20-epi-22-ethoxy-23-yne-24a,26a,27a-trihomo-1α,25-(OH)₂D₃ (CB 1093) | OEt | 20-epi-1α,25-(OH)₂D₃ (KH 1060) | |

1α,25-fluoro-25-(OH)-16,23E-diene-26,27-bishomo-20epi-cholecalciferol (Ro-26-6228, BXL-628, RS-980400)

2-methylene-19-nor-(20S)-1α,25-(OH)₂D₃ (2MD)

Other Agents

The disclosed compositions can include other therapeutic agents, such as chemotherapeutics, biologics (e.g., monoclonal antibodies, inhibitory RNA molecules), and the like. Specific examples are disclosed below.

In some examples, the composition includes a pharmaceutically acceptable carrier, diluents, and the like. Specific examples are disclosed below.

Methods of Using Compositions Containing Nanoparticles and VDR Agonist

The present disclosure also provides methods of using the disclosed compositions that include a nanoparticle and a compound that increases the biological activity of the VDR to increase or retain vitamin A, vitamin D, and/or lipid in a cell, such as an epithelial or stellate cell. Thus, provided are methods that can be used to return an active stellate or epithelial cell to its quiescent state, or to maintain a stellate or epithelial cell in a quiescent state.

In some examples, the method includes contacting a therapeutically effective amount of the one or more of the disclosed compositions with a cell (e.g., a VDR positive cell), such as an epithelial or stellate cell, such as an activated epithelial or stellate cell. Such a method can be used to increase or retain vitamin A, vitamin D, and/or lipid in the cell, and thus be used to return an active stellate or epithelial cell to its quiescent state, or to maintain a stellate or epithelial cell in a quiescent state. In some examples, the cell is in a subject, and contacting includes administering a therapeutically effective amount of the composition to the subject, thereby increasing or retaining vitamin A, vitamin D, and/or lipid in the cells of the subject (such as epithelial and/or stellate cells, such as pancreatic stellate cells, liver stellate cells, heart stellate cells, lung stellate cells, and/or kidney stellate cells).

In some examples, the method increases the retention or storage of vitamin A by a cell (such as a stellate or epithelial cell) by at least 10%, at least 20%, at least 25%, at least 40%, at least 50%, at least 75%, at least 80%, at least 90%, or at least 95%, as compared to an absence of the treatment. In one example, the method increases the retention or storage of vitamin D by a cell (such as a stellate or epithelial cell) by at least 10%, at least 20%, at least 25%, at least 40%, at least 50%, at least 75%, at least 80%, at least 90%, or at least 95%, as compared to an absence of the treatment. In one example, the method increases the retention or storage of lipids by a cell (such as a stellate or epithelial cell) by at least 10%, at least 20%, at least 25%, at least 40%, at least 50%, at least 75%, at least 80%, at least 90%, or at least 95%, as compared to an absence of the treatment.

In some examples, the subject to be treated has a liver disease, such as one or more of alcohol liver disease, fatty liver disease, liver fibrosis/cirrhosis, biliary fibrosis/cirrhosis, liver cancer (such as hepatocellular carcinoma, cholangiocarcinoma, angiosarcoma, or hemangiosarcoma), hepatitis, sclerosing cholangitis, Budd-Chiari syndrome, jaundice, hemochromatosis, or Wilson's disease. In some examples, the subject to be treated has a pancreatic disease, such as pancreatic fibrosis, pancreatic ductal adenocarcinoma (PDA), or both. In some examples, the subject to be treated has a kidney disease, such as fibrosis of the kidney or renal cell carcinoma. Thus, the disclosed compositions can be used to treat or prevent one or more of these diseases.

In one example, the subject shows symptoms of fibrosis of the liver, pancreas, or kidney. For example, the subject may be infected with hepatitis B or hepatitis C. In some examples, the administration of a therapeutic composition that includes a nanoparticle and a compound that increases the biological activity of the VDR reduces the symptoms of fibrosis. In some examples, the subject is at risk for developing fibrosis (e.g., is infected with hepatitis B or is an alcoholic or has other liver disease), and the therapeutic composition is administered prophylactically.

In some examples, the disclosed methods can be used to reduce one or more of fibrosis (for example by decreasing the fibrotic content of a fibrotic liver, kidney or pancreas), decrease tumor growth, size or volume, and metastatic lesions, as compared to no treatment with the disclosed compositions. Thus, in some examples, the method reduces fibrosis (for example by decreasing the fibrotic content of a fibrotic liver, kidney or pancreas) by at least 10%, at least 20%, at least 25%, at least 40%, at least 50%, at least 75%, at least 80%, at least 90%, or at least 95%, as compared to an absence of the treatment. In some examples, the method reduces the rate of tumor growth (such as a tumor of the liver, kidney or pancreas) by at least 10%, at least 20%, at least 25%, at least 40%, at least 50%, at least 75%, at least 80%, at least 90%, or at least 95%, as compared to an absence of the treatment. In some examples, the method reduces the size or volume of a tumor (such as a tumor of the liver, kidney or pancreas) by at least 10%, at least 20%, at least 25%, at least 40%, at least 50%, at least 75%, at least 80%, at least 90%, or at least 95%, as compared to an absence of the treatment. In some examples, the method reduces the number, size or volume of a metastasis (such as a metastasis of a liver, kidney or pancreas tumor) by at least 10%, at least 20%, at least 25%, at least 40%, at least 50%, at least 75%, at least 80%, at least 90%, or at least 95%, as compared to an absence of the treatment.

In some examples, the disclosed methods are prophylactic. For example, the method can include administering a subject at risk for developing fibrosis a therapeutic composition that includes a nanoparticle and a compound that increases the biological activity of the VDR. Such prophylactic administration can delay the onset of the symptoms of fibrosis of the liver, kidney or pancreas. For example, prophylactic administration of a composition that includes a nanoparticle and a compound that increases the biological activity of the VDR can be used to prevent the onset of one or more symptoms or features of fibrosis. For example, as an organ undergoes fibrosis, the functional cellular mass of the organ is reduced as it is replaced by scar tissue (collagens and other abnormal matrix components). In addition, fibrosis causes architectural disorganization that can diminish function and lead to pathology, such as portal hypertension and increased risk of hepatocellular carcinoma in the case of the liver. Severe portal hypertension usually manifests as bleeding esophageal/gastric varices and/or ascites. In the kidney and pancreas the features of advanced fibrosis are renal failure and endocrine and/or exocrine pancreatic failure.

Monitoring Therapy

These actions of the compositions provided herein are, in certain embodiments, monitored by blood, serum and plasma markers of liver inflammation, injury, and fibrogenesis, including but not limited to; aspartate aminotransferase, alanine aminotransferase, gamma glutamyl transpeptidase, bilirubin, alpha-2 macroglobulin, haptoglobin, tissue inhibitor of metalloproteinase-1, hyaluronic acid, amino terminal propeptide of type III collagen and other collagen precursors and metabolites, platelet count, apolipoprotein A1, C-reactive protein and ferritin. These tests are used alone in some examples, whereas in other examples they are used in combination. Hepatic fibrosis may also be monitored by the technique of transient elastography (Fibroscan™). A further embodiment includes monitoring the impact of the treatments by direct examination of liver tissue obtained by liver biopsy.

The effects of the disclosed methods on diseases of the pancreas are monitored, in some embodiments, by blood, serum, plasma amylase, or lipase, as well as tests of pancreatic exocrine and endocrine function. In other embodiments, pancreatitis is monitored by imaging techniques, including but not limited to radiological, nuclear medicine, ultrasound, and magnetic resonance.

The effects of the disclosed methods on diseases of the kidney are monitored, in some embodiments, by the measurement of blood, serum, or plasma urea or creatinine, or other tests of renal function, alone or in combination. Kidney disease is monitored, in some embodiments, by imaging techniques, including but not restricted to radiological, nuclear medicine, ultrasound, and magnetic resonance. In alternate embodiments, the impact of the treatments on the kidney is monitored by direct examination of tissue obtained by kidney biopsy.

Combination with Other Therapeutic Agents

The disclosed compositions can be used for treatment in combination with other therapeutic agents, such as chemotherapies and biotherapies. In one example, the other therapeutic agents include one or more nuclear receptor ligands, including but not limited to ligands for peroxisome proliferator-activated receptor-gamma (PPAR-γ, NR1C3), peroxisome proliferator-activated receptor-alpha (PPAR-α, NR1C1) and peroxisome proliferator-activated receptor-delta (PPAR-δ, NR1C2), farnesoid X receptor (FXR, NR1H4), interferon-gamma (IFN-γ), angiotensin converting enzyme inhibitors, angiotensin II receptor antagonists, ursodeoxycholic acid (UDCA), curcumin, anti-oxidants including, but not limited to vitamin E, retinoids such as Vitamin A, and therapies that deliver proteases to the liver to degrade pathological ECM. In some examples, other therapeutic agents are part of the nanoparticle/VDR agonist compositions provided herein.

The terms "co-administration," "administered in combination with," and their grammatical equivalents, are meant to encompass administration of two or more therapeutic agents to a single subject, and are intended to include treatment regimens in which the agents are administered by the same or different route of administration or at the same or different times. In some embodiments the one or more compositions described herein will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

Exemplary Chemotherapies and Biologic Therapies

The disclosed methods can use the disclosed compositions in combination with other therapeutic agents, such as chemotherapies and biotherapies. In some examples, such chemotherapies and/or biotherapies are part of the nanoparticle/VDR agonist compositions provided herein. Chemotherapies and biotherapies can include anti-neoplastic chemotherapeutic agents, antibiotics, alkylating agents and antioxidants, kinase inhibitors, and other agents such as antibodies. Methods and therapeutic dosages of such agents are known to those skilled in the art, and can be determined by a skilled clinician. Other therapeutic agents, for example anti-tumor agents, that may or may not fall under one or more of the classifications below, also are suitable for administration in combination with the described compositions. Selection and therapeutic dosages of such agents are known to those skilled in the art, and can be determined by a skilled clinician.

In one example, a chemotherapy or biotherapy increases killing of cells, such as liver, pancreatic, or kidney cells (or reduces their viability). Such killing need not result in 100% reduction of cells; for example a chemotherapy that results in reduction in the number of viable cells (such as a cancer cell) by at least 10%, at least 20%, at least 30%, at least 40%, at least 50%, at least 75%, at least 90%, or at least 95% (for example as compared to no treatment with the chemotherapy or bio-therapy) can be used in the methods provided herein. For example, a chemotherapy or bio-therapy can reduce the growth of cells (such as cancers cell) by at least 10%, at least 20%, at least 30%, at least 40%, at least 50%, at least 75%, at least 90%, or at least 95% (for example as compared to no chemotherapy or bio-therapy).

Particular examples of chemotherapeutic agents that can be used (and in some examples are part of a composition that includes a nanoparticle and a VDR agonist) include alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; folic acid (for example, methotrexate, pemetrexed, and raltitrexed), purine (for example, cladribine, clofarabine, fludarabine, mercaptopurine, and tioguanine), pyrimidine (for example, capecitabine, cytarabine, fluorouracil, and gemcitabine; plant alkaloids, such as podophyllum (for example, etoposide, and teniposide); microtubule binding agents (such as paclitaxel, docetaxel, vinblastine, vindesine, vinorelbine (navelbine) vincristine, the epothilones, colchicine, dolastatin 15, nocodazole, podophyllotoxin, rhizoxin, and derivatives and analogs thereof), DNA intercalators or cross-linkers (such as cisplatin, carboplatin, oxaliplatin, mitomycins, such as mitomycin C, bleomycin, chlorambucil, cyclophosphamide, and derivatives and analogs thereof), DNA synthesis inhibitors (such as methotrexate, 5-fluoro-5'-deoxyuridine, 5-fluorouracil and analogs thereof); anthracycline family members (for example, daunorubicin, doxorubicin, epirubicin, idarubicin, mitoxantrone, and valrubicin); antimetabolites, such as cytotoxic/antitumor antibiotics, bleomycin, rifampicin, hydroxyurea, and mitomycin; topoisomerase inhibitors, such as topotecan and irinotecan; photosensitizers, such as aminolevulinic acid, methyl aminolevulinate, porfimer sodium, and verteporfin, enzymes, enzyme inhibitors (such as camptothecin, etoposide, formestane, trichostatin and derivatives and analogs thereof), kinase inhibitors (such as imatinib, gefitinib, and erolitinib), gene regulators (such as raloxifene, 5-azacytidine, 5-aza-2'-deoxycytidine, tamoxifen, 4-hydroxytamoxifen, mifepristone and derivatives and analogs thereof); and other agents, such as alitretinoin, altretamine, amsacrine, anagrelide, arsenic trioxide, asparaginase, axitinib, bexarotene, bevacizumab, bortezomib, celecoxib, denileukin diftitox, estramustine, hydroxycarbamide, lapatinib, pazopanib, pentostatin, masoprocol, mitotane, pegaspargase, tamoxifen, sorafenib, sunitinib, vemurafinib, vandetanib, and tretinoin.

In one example, a bio-therapy (which in some examples is part of a composition that includes a nanoparticle and a VDR agonist) includes or consists of an antibody, such as a humanized antibody. Such antibodies can be polyclonal, monoclonal, or chimeric antibodies. As noted above, methods of making antibodies specific for a particular target is routine. In some example, the therapeutic antibody is conjugated to a toxin. Exemplary biotherapies include alemtuzumab, bevacizumab, cetuximab, gemtuzumab, rituximab, panitumumab, pertuzumab, and trastuzumab.

Other examples of bio-therapy (which in some examples are part of a composition that includes a nanoparticle and a VDR agonist) include inhibitory nucleic acid molecules, such as an antisense oligonucleotide, a siRNA, a microRNA (miRNA), a shRNA or a ribozyme. Any type of antisense compound that specifically targets and regulates expression of a target nucleic acid is contemplated for use. An antisense compound is one which specifically hybridizes with and modulates expression of a target nucleic acid molecule. These compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self complementarity to allow for hybridization and formation of a fully or partially double-stranded compound. In some examples, an antisense oligonucleotide is a single stranded antisense compound, such that when the antisense oligonucleotide hybridizes to a target mRNA, the duplex is recognized by RNaseH, resulting in cleavage of the mRNA. In other examples, a miRNA is a single-stranded RNA molecule of about 21-23 nucleotides that is at least partially complementary to an mRNA molecule that regulates gene expression through an RNAi pathway. In further examples, a shRNA is an RNA oligonucleotide that forms a tight hairpin, which is cleaved into siRNA. siRNA molecules are generally about 20-25 nucleotides in length and may have a two nucleotide overhang on the 3' ends, or may be blunt ended. Generally, one strand of a siRNA is at least partially complementary to a target nucleic acid. Antisense compounds specifically targeting a gene can be prepared by designing compounds that are complementary to a target nucleotide sequence, such as an mRNA sequence. Antisense compounds need not be 100% complementary to the target nucleic acid molecule to specifically hybridize and regulate expression of the target. For example, the antisense compound, or antisense strand of the compound if a double-stranded compound, can be at least 75%, at least 80%, at least 85%, at least 90%, at least 95%, at least 99% or 100% complementary to a target nucleic acid sequence. Methods of screening antisense compounds for specificity are well known (see, for example, U.S. Publication No. 2003-0228689). In addition, methods of designing, preparing and using inhibitory nucleic acid molecules are within the abilities of one of skill in the art.

Administration of Therapeutic Agents

In some examples, the disclosed methods include providing a therapeutically effective amount of one or more of the disclosed compositions alone or in combination with another therapeutic agent, such as a chemotherapy or biotherapy, to a subject. Methods and therapeutic dosages of such agents and treatments are known to those of ordinary skill in the art, and for example, can be determined by a skilled clinician. In some examples, the disclosed methods further include providing surgery and/or radiation therapy to the subject in combination with the treatments described herein (for example, sequentially, substantially simultaneously, or simultaneously). Administration can be accomplished by single or multiple doses. Methods and therapeutic dosages of such agents and treatments are known to those skilled in the art, and can be determined by a skilled clinician. The dose required will vary from subject to subject depending on the species, age, weight and general condition of the subject, the particular therapeutic agent being used and its mode of administration.

Therapeutic agents, including the nanoparticle/VDR agonist compositions provided herein, can be administered to a subject in need of treatment using any suitable means known in the art. Methods of administration include, but are not limited to, intradermal, transdermal, intramuscular, intraperitoneal, parenteral, intratumoral, intravenous, subcutaneous, vaginal, rectal, intranasal, inhalation, oral, or by gene gun. Intranasal administration refers to delivery of the compositions into the nose and nasal passages through one or both of the nares and can include delivery by a spraying mechanism or droplet mechanism, or through aerosolization of the therapeutic agent.

Administration of the therapeutic agents by inhalant can be through the nose or mouth via delivery by spraying or droplet mechanisms. Delivery can be directly to any area of the respiratory system via intubation. Parenteral administration is generally achieved by injection. Injectables can be prepared in conventional forms, either as liquid solutions or suspensions, solid forms suitable for solution of suspension in liquid prior to injection, or as emulsions. Injection solutions and suspensions can be prepared from sterile powders, granules, and tablets. Administration can be systemic or local.

Therapeutic agents, including the nanoparticle/VDR agonist compositions provided herein, can be administered in any suitable manner, for example with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure. The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration, including topical administration of the nanoparticle/VDR agonist compositions provided herein, can include ointments, lotions, creams, gels, drops, suppositories, sprays, liquids and powders. Conventional pharmaceutical carriers, aqueous, powder or oily bases, thickeners and the like may be necessary or desirable.

Therapeutic agents for oral administration, including oral administration of the nanoparticle/VDR agonist compositions provided herein, include powders or granules, suspensions or solutions in water or non-aqueous media, capsules, sachets, or tablets. Thickeners, flavorings, diluents, emulsifiers, dispersing aids or binders may be desirable.

Therapeutic agents, including the nanoparticle/VDR agonist compositions provided herein, can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

In some examples, the dose of a composition that includes an agent that increase VDR activity and a nanoparticle is about 1 mg to about 1000 mg, about 10 mg to about 500 mg, or about 50 mg to about 100 mg. In some examples, the dose of the composition is about 1 mg, about 10 mg, about 50 mg, about 100 mg, about 250 mg, about 500, about 700 mg, about 1000 mg, about 2000 mg, about 3000 mg, about 4000 mg, about 5000 mg, about 6000 mg, about 7000 mg, about 9000 mg or about 10,000 mg. In some embodiments, the dose of a the composition is about 1 µg/kg to about 1000 mg/kg, about 1 µg/kg to 1000 µg/kg, about 1 µg/kg to 100 µg/kg, or about 5 mg/kg to about 500 mg/kg, about 10 mg/kg to about 100 mg/kg, about 50 mg/kg to 100 mg/kg, or about 25 to about 50 mg/kg. In some examples, the dose of the composition is about 1 µg/kg, 10 µg/kg, 20 µg/kg, 50 µg/kg, 100 µg/kg, 500 µg/kg, 1 mg/kg, about 5 mg/kg, about 10 mg/kg, about 12.5 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg or about 100 mg/kg. It will be appreciated that these dosages are examples only, and an appropriate dose can be determined by one of ordinary skill in the art using only routine experimentation. In one example the dose is about 20 µg/kg PO.

In one example, therapeutically effective doses of vitamin D2 and D3 range, from about 50 IU to about 50,000 IU. In some embodiments, vitamin D2 and/or D3 is administered in an oral dose of, for example, less than about 75 IU, about 100 IU, about 250 IU, about 500 IU, about 750 IU, about 1,000 IU, about 1,500 IU, about 2,000 IU, about 2,500 IU, about 5,000 IU, about 7,500 IU, about 10,000 IU, about 15,000 IU, about 20,000 IU, about 25,000 IU, about 40,000 IU, or about 50,000 IU, or more. In other embodiments, calcitriol is administered in a dose of from 0.001 to 10 micrograms. For instance, calcitrol is administered, in some embodiments, in a dose of about 0.01 µg, about 0.05 µg, about 0.1 µg, about 0.25 µg, about 0.5 µg, about 1 µg, about 5 µg, or about 10 µg. In some embodiments, larger doses of VDR agonists are administered via a delivery route that targets the organ of interest, for instance the liver, kidney or pancreas.

In certain embodiments, the composition containing the nanoparticle and the agent that increases VDR activity is administered orally, for instance, in single or divided doses. For oral administration, the compositions are, for example, provided in the form of a tablet containing 1.0 to 1000 mg of the active ingredient, such as at least 75 IU, at least 100 IU, at least 250 IU, at least 500 IU, at least 750 IU, at least 800 IU, at least 1,000 IU, at least 1,500 IU, at least 2,000 IU, at least 2,500 IU, at least 5,000 IU, at least 7,500 IU, at least 10,000 IU, at least 15,000 IU, at least 20,000 IU, at least 25,000 IU, at least 40,000 IU, or 5 at least 0,000 IU per day, for example 50 IU to 2000 IU per day, 100 IU to 1000 IU per day, such as 800 IU per day, or more of the active ingredient for the symptomatic adjustment of the dosage to the subject being treated. An effective parenteral dose could be expected to be lower, for example in the range of about 0.001 µg to about 10 µg, depending on the compound.

In another embodiment, if the agent that increase VDR activity in the nanoparticle composition is not a 1α-hydroxy compound, a daily dose between 1.0 and 100 µg per day per 160 pound patient is administered, such as between 5.0 and 50 µg per day per 160 pound patient. In a different embodiment, if the biologically active vitamin D compound is a 1α-hydroxy compound, a daily dose of between 0.1 and 20 µg per day per 160 pound patient is administered, while a preferred dose is between 0.5 and 10 µper day per 160 pound patient. In a particular example, the dose is between 3-10 µg per day.

In one example, the VDR agonist in the nanoparticle composition is cholecalciferol or calcidiol. In some examples, a higher dose than usual is administered, but with less frequency, for example, 50,000 to 500,000 units weekly.

Methods of Screening

Based on the observation that the VDR is a target for identifying agents that can treat or prevent fibrosis, provided herein are screening methods for identifying one or more agents that can treat or prevent fibrosis, such as fibrosis of the liver, pancreas, and/or kidney. In some examples, the method includes contacting a cell (such as a hepatic, pancreatic, lung, heart or renal stellate cell) with one or more test agents. In one example the cell is a hepatic stellate cell, such as a primary cell or an immortalized cell line derived from a hepatic stellate cell or other cell line that retains some phenotypic or functional features of stellate cells. In some examples, a plurality of cells is contacted with one test agent at a time. In some examples, a plurality of cells are contacted with two more different test agents simultaneously, such as 1, 2, 3, 4, 5, 6, 7, 8, 9 or 10 different test agents. The amount of test agent added can be determined by one skilled in the art. In some examples, the amount of test agent(s) added to the cells in vitro (e.g., adding the test agent to cells growing in culture, for example in a tissue culture dish or multi-well plate or other substrate, in growth medium) is at least 1 nM, at least 10 nM, at least 100 nM, at least 1 mM, at least 10 mM, at least 100 mM, or 1000 mM, such as 1 nM to 1 M, 1 nM to 100 nM or 1 nM to 10 nM. In some examples, cells are cultured with at least 1 international unit (IU), such as at least 5 IU, at least 10 IU, at least 10 IU, at least 100 IU, at least 1000 IU, at least 5000 IU, at least 10,000 IU, at least 50,000 IU, at least 100,000 IU or at least 500,000 IU, for example from 5 IU about 50,000 IU, 5 to 10,000 IU, 10 to 1000 IU, or 50,000 to 500,000 IU of one or more test agents. In some examples, the amount of test agent(s) added to the cells in vitro (e.g., adding the test agent to cells growing in culture, for example in a tissue culture dish or multi-well plate or other substrate, in growth medium) is 1 nM to 10 µM screened at increasing half-log concentrations. In particular embodiments, the test agent includes a VDR agonist.

In some examples the cell is also contacted with an amount of TGF-$\beta_1$ sufficient to increase VDR expression by the cell relative to expression in an absence of the TGF-$\beta_1$. In some examples, expression of VDR by the cell increases by at least 2-fold, at least 3-fold, at least 4-fold, at least 5-fold, at least 10-fold, or at least 20-fold, such as 2-fold to 50-fold, 2-fold to 20-fold, 2-fold to 10-fold, 2-fold to 5-fold, 3-fold, 4-fold, 5-fold or 6-fold, as compared to an amount of expression without the added TGF-$\beta_1$. Methods of measuring VDR expression are known in the art, and can include but are not limited to: PCR, RT-qPCR, FISH, Western blotting, fluorescence microscopy of proteins, and the like. In some examples, the method also includes the step of measuring VDR expression following addition of TGF-$\beta_1$. The amount of TGF-$\beta_1$ added can be determined by one skilled in the art. In some examples, the amount of TGF-$\beta_1$ added to the cells in vitro is at least 0.1 ng/ml, at least 1 ng/ml, at least 5 ng/mL, at least 10 ng/ml, at least 100 ng/ml, at least 1 mg/ml, at least 10 mg/ml, at least 100 mg/ml, or 1000 mg/ml, such as 0.1 ng/ml to 1 g/ml, 1 ng/ml to 100 ng/ml, 1 ng/ml to 5 ng/mL, or 1 ng/ml to 10 ng/ml, such as 1 ng/ml.

In some examples, the one or more test agents are added to the cells at the same time as the TGF-$\beta_1$, such as simultaneously, or contemporaneously. In some examples, the test agent is added before TGF-$\beta_1$, for example for a period of at least 1 hour, at least 6 hours, at least 12 hours, or at least 24 hours before TGF-$\beta_1$. In some examples, TGF-$\beta_1$ is added before the test agent, for example for a period of at least 1 hour, at least 6 hours, at least 12 hours, or at least 24 hours before the test agent(s) (such as 4-6 hours before). In some examples, the test agent and TGF-$\beta_1$ are incubated with the cells for at least 30 minutes, such as at least 60 minutes, at least 2 hours, at least 4 hours, at least 6 hours, at least 8 hours, at least 12 hours, at least 16 hours, at least 24 hours, or at least 48 hours, such as 6-24 hours, 6-12 hours, or 8-24 hours, such as 24 hours.

Following incubation with the one or more test agents and TGF-$\beta_1$, the method can include one or more of detecting: (1) production of a VDR agonist or calcitriol by the cell, (2) production of CYP24A1 by the cell, (3) production, post-translational modification of, or expression of SMAD3 by the cell, or (4) binding of VDR to a VDR agonist. Methods of measuring such are well known in the art and the disclosure is not limited to particular detection methods. For example, production of a VDR agonist by the cell can be measured by mass spectrometry, immunoassay or other assay systems (including in vivo cell based and in vitro VDR/coactivator association assays capable of detecting specific chemical structures or families of chemical structures). Production or expression of CYP24A1 and/or SMAD3 by the cell can be measured by any method used to measure nucleic acid or protein expression, such as methods that use CYP24A1-specific antibodies or SMAD3-specific antibodies (e.g., Western blotting, immunohistochemistry, and the like) as well as methods that use CYP24A1-specific or SMAD3-specific probes or primers (e.g., PCR amplification, in situ hybridization, and the like). Methods of measuring binding of VDR to the VDR agonist include but are not limited to measuring ligand induced receptor-co-activator binding (e.g., using AlphaQuest® system from Perkin Elmer), FRET measurements of ligand induced receptor-co-activator binding, competitive ligand binding assay (e.g., using radio-labeled VDR ligands), differential thermal stability of the ligand binding domains and the like.

Test agents can be selected that do one or more of (1) increase production of a VDR agonist or calcitriol by the cell by at least 2-fold, at least 3-fold, at least 4-fold, at least 5-fold, or at least 10-fold relative to the absence of the one or more test agents, (2) increase production or expression of CYP24A1 by the hepatocyte cell by at least 2-fold, at least 3-fold, at least 4-fold, at least 5-fold, or at least 10-fold relative to the absence of the one or more test agents, (3) reduce production or expression of SMAD3 by the hepatocyte cell by at least 1-fold, at least 1.5 fold, at least 2-fold, at least 3-fold, at least 4-fold, at least 5-fold, or at least 10-fold relative to the absence of the one or more test agents, or (4) increase binding of VDR to the VDR agonist by at least 2-fold, at least 3-fold, at least 4-fold, at least 5-fold, or at least 10-fold relative to the absence of the one or more test agents, wherein the selected test agents are agents that can treat or prevent fibrosis.

In some embodiments, the screening method also includes determining whether the VDR agonist produced by the cell can be degraded by Cyp24A1, and in other embodiments, the method also includes selecting test agents that did not result in degradation of a VDR agonist by Cyp24A1.

In some embodiments, the method further includes determining whether the agent has hypercalcemic effects in vitro, and in certain examples the method also includes selecting test agents that did not have hypercalcemic effects in vitro. In still other embodiments, the method further includes determining whether the agent has hypercalcemic effects in vivo, and in certain examples the method also includes selecting test agents that did not have hypercalcemic effects in vivo (e.g., did not cause levels of calcium in the blood to be ≥3 mmol/l).

Additional embodiments include administering one or more of the selected test agents to a mammal having fibrosis, and determining whether the one or more test agents treat or prevent the fibrosis, and in some examples, selecting test agents that treated or prevented the fibrosis. Animal models of fibrosis are well known, such as the $CCl_4$ model of liver injury and fibrosis described in the examples below.

Also provided herein are methods of increasing expression of VDR by a stellate cell in vivo or in vitro. Such methods can include contacting the stellate cell with an amount of a VDR agonist and optionally an amount of TGF-$\beta_1$ sufficient to enhance binding of VDR agonist to the VDR by at least 10-fold.

Example 1

Experimental Procedures

This example provides the materials and methods for the results described in the examples below.

Primary HSCs Isolation and Culture

HSCs were isolated from 10-week old male C57BL/6J mice and Wistar rats by in situ pronase, collagenase perfusion and single-step Histogenz gradient as previously reported (Hendriks et al., 1985; Knook et al., 1982). Isolated HSCs were cultured in DMEM (Mediatech) containing 20% FBS (Hyclone) on 6-well plates for 40 hours prior to end-point assays.

Immunoprecipitation and Western Blot

The whole cell lysates were obtained through RIPA buffer lysis while isolation of nuclear extract was performed as previously reported (Ding et al., 2008). Total and nuclear SMAD3 were immmunoprecipitated from LX-2 whole cell and nuclear extracts, respectively, using anti-SMAD2/3 antibody (Santa Cruz, sc-133098) followed by SDS-PAGE and western blot detection by anti-SMAD3 (Cell Signaling, 9523) and anti-pSMAD3 (Cell Signaling, 9520) specific antibodies.

Cell Culture, Luciferase Assay and RT-qPCR

LX-2 cells, a generous gift from Professor Scott Friedman, Mount Sinai School of Medicine, New York, N.Y., were cultured as described previously (Xu et al., 2005). TGFβ1 (R&D Systems), 1,25(OH)$_2$D$_3$, and calcipotriol (Tocris) were used at concentrations of 1 ng/ml, 100 nM and 100 nM, respectively, except when otherwise indicated. For luciferase assays, DNA transfections were performed using Fugene 6 (Roche) following the manufacturer's instructions. 24 hours following DNA transfections, cells were treated with vehicle, calcipotriol or TGFβ1 or both for another 24 hours prior to Luciferase/β-galactosidase assays (Promega). RT-qPCR, total RNA was purified following TRIzol extraction and treated with DNaseI (Invitrogen). cDNA synthesis was carried out with iScript RT Supermix (Biorad). Quantitative PCR was performed in technical triplicates using SYBR Green reagent (Biorad). The relative standard curve method was used for quantitation (Biorad). Expression levels were calculated by normalization to either Gapdh (mouse) or U36B4 (human) quantities. The sequences of primers are listed in Table 2.

TABLE 2

Primer sequences qRT-PCR Primers

| Gene Name | Species | Sequence | SEQ ID NO |
|---|---|---|---|
| Gapdh | mouse | TCAACAGCAACTCCCACTCTTCCA | 1 |
|  |  | TTGTCATTGAGAGCAATGCCAGCC | 2 |
| Vdr | mouse | GCTGAACCTCCATGAGGAAG | 3 |
|  |  | GGATCATCTTGGCGTAGAGC | 4 |
| Cyp24a1 | mouse | GACCGCAAACAGCTTGATGTGGAT | 5 |

TABLE 2-continued

Primer sequences

| | | | SEQ ID NO |
|---|---|---|---|
| | | ATATTCCTCACATCTTCCGCCCGT | 6 |
| Col1a1 | mouse | ACTGCAACATGGAGACAGGTCAGA | 7 |
| | | ATCGGTCATGCTCTCTCCAAACCA | 8 |
| Tgfβ1 | mouse | TTTGGAGCCTGGACACACAGTACA | 9 |
| | | TGTGTTGGTTGTAGAGGGCAAGGA | 10 |
| Timp1 | mouse | GGTGTGCACAGTGTTTCCCTGTTT | 11 |
| | | TCCGTCCACAAACAGTGAGTGTCA | 12 |
| U36B4 | human | GCAGTGATGTAAAATTTCTTGG | 13 |
| | | AAA GCT CGGTTTTACTCTTCACA | 14 |
| VDR | human | CTGTGGCAACCAAGACTACA | 15 |
| | | CCCACCTGGAACTTGATGAG | 16 |
| CYP24A1 | human | CCTGCTGCAGATTCTCTGGAA | 17 |
| | | AGGGTGTCGTGCTGTTTCTTG | 18 |
| SMAD2 | human | ACCGAAGGCAGACGGTAACAAGTA | 19 |
| | | GACATGCTTGAGCAACGCACTAA | 20 |
| SMAD3 | human | ATGTCAACAGGAATGCAGCAGTGG | 21 |
| | | ATAGCGCTGGTTACAGTTGGGAGA | 22 |
| COL1A1 | human | CGGTGTGACTCGTGCAGC | 23 |
| | | ACAGCCGCTTCACCTACAGC | 24 |
| COL1A2 | human | TCAAACTGGCTGCCAGCAT | 25 |
| | | CAAGAAACACGTCTGGCTAGG | 26 |
| TGFβ1 | human | CGCTAAGGCGAAAGCCCTCAATTT | 27 |
| | | ACAATTCCTGGCGATACCTCAGCA | 28 |
| TIMP1 | human | TCTGCAATTCCGACCTCGTCATCA | 29 |
| | | AAGGTGGTCTGGTTGACTTCTGGT | 30 |

ChIP-qPCR Primers

| Gene Name | Species | Sequence | SEQ ID NO |
|---|---|---|---|
| COL1A1 | human | CATTCCCAGCTCCCCTCTCT | 31 |
| | | AGTCTACGTGGCAGGCAAGG | 32 |
| COL1A2 | human | CCTGAGCCAGTAACCACCTCC | 33 |
| | | CTTTCGAAGCTAACGTGGCAG | 34 |

Transfection of siRNAs

Transfection was carried out at a concentration of 20 nM of indicated siRNAs (in the case of SMAD2/3, 10 nM of each siRNA was combined for transfection) using RNAiMax transfection reagent (Invitrogen). Transfected cells were cultured without perturbation for at least 48 hours prior to terminal assays.

$CCl_4$ Model of Liver Injury and Fibrosis 8 week-old male C57BL/6J mice were IP injected with 0.5 ml/kg body weight $CCl_4$ (1:50 v/v in corn oil from Sigma) or vehicle (DMSO in corn oil) three times a week for 4 weeks. Calcipotriol (20 μg/kg body weight) was administered by oral gavage 5 times a week, commencing 20 days after the first dose of $CCl_4$. The animals were terminated 72 hours after the final $CCl_4$ injection and whole livers and serum were collected for histological, cytological, biochemical and molecular analyses.

Vdr Knockout Mice

C57BL/6J mice heterozygous for targeted ablation of Vdr (Li et al., 1997) were obtained from The Jackson Laboratory (Stock Number 006133). Wild type controls, $Vdr^{+/-}$ and $Vdr^{-/-}$ mice were maintained on a $Vdr^{-/-}$ rescue diet (Amling et al., 1999) containing 21% calcium, and 0.67% phosphorus and 20% lactose supplemented with 4.4 units of vitamin D per gram diet for 6 months prior to sacrifice. Livers were collected for analysis as above.

Fibrotic Score and Quantification of Hepatic Collagen and Hydroxyproline Content 5 μm sections of formalin-fixed liver were stained following standard H&E and Sirius Red methods and reviewed by a pathologist who was blinded to the experimental conditions. Fibrosis was scored using the Ishak modified histological activity index (HAI) scoring system. Fibrosis was also quantified using Image J software on 10 non-contiguous Sirius Red stained sections. All images were obtained using a high-resolution Leica DFC420 digital camera mounted on an Olympus microscope equipped with ×4/0.13, ×10/0.30, ×20/0.50 and ×40/0.75 UplanFL N plan objective lenses and processed with the Leica Application Suite. Hepatic hydroxyproline content was measured using a commercial colorimetric assay from Biovision (K555-100).

ChIP and ChIP-Re-ChIP

LX-2 cells were pretreated with calcipotriol (100 nM) for 16 hours followed by incubation of calcipotriol (100 nM) or TGFβ1 (1 ng/ml) or both for an additional 4 hours. Cells were then harvested for ChIP assay. The experimental procedure for ChIP was as previously described (Barish et al., 2010). Briefly, after fixation, nuclei from LX-2 cells were isolated, lysed and sheared with a Diagenode Bioruptor to yield DNA fragment sizes of 200-1000 base pairs followed by immunoprecipitation using antibodies listed below: normal rabbit IgG (Santa Cruz, sc-2027), VDR (Santa Cruz, sc-1008), SMAD3 (Abcam, ab28379) and histone H3 (Abcam, ab1791). For ChIP-Re-ChIP, after first ChIP, the immunoprecipitated DNA-protein complex was eluted from beads using 10 mM DTT, diluted 100-fold then re-immunoprecipitated with a second antibody, re-ChIP.

ChIP-seq Data Analysis

The procedure was as previously described (Barish et al., 2010). Briefly, short DNA reads were aligned against the human hg18 reference genome (NCBI Build 36.1) using the Illumina Pipeline Suite v 1.7. Reads were aligned using the Bowtie aligner allowing up to 2 mismatches in the read. Only tags that map uniquely to the genome were considered for further analysis. Subsequent peak calling and motif analysis were conducted using HOMER, a software suite for ChIP-Seq analysis. The methods for HOMER, which are described below, have been implemented and are freely available at http://biowhat.ucsd.edu/homer/ (Heinz et al., 2010). One tag from each unique position was considered to eliminate peaks resulting from clonal amplification of fragments during the ChIPSeq protocol. Peaks were identified by searching for clusters of tags within a sliding 200 bp window, requiring adjacent clusters to be at least 1 kb away from each other. The threshold for the number of tags that determine a valid peak was selected for a false discovery rate of <0.0001, as empirically determined by repeating the peak finding procedure using randomized tag positions. Peaks are required to have at least 4-fold more tags (normalized to total count) than input or IgG control samples and 4-fold more tags relative to the local background region (10 kb) to avoid identifying regions with genomic duplications or non-localized binding. Peaks are annotated to gene products by identifying the nearest RefSeq transcriptional start site. Visualization of ChIP-Seq results was achieved by uploading custom tracks onto the UCSC genome browser. Human phenotype analysis was performed using GREAT (Genomic Regions Enrichment of Annotations Tool) at http://great-.stanford.edu/.

Microarray Data Analysis

Total RNA from primary rat or mouse HSCs was isolated using the RNeasy mini kit (Qiagen) according to standard protocols. RNA integrity and quality was assessed using the Agilent Bioanalyzer and prepared for hybridization to Illumina rat or mouse gene expression arrays according to standard Illumina protocols. Feature extraction was performed using the Illumina GenomeStudio software. Normalization and identification of differentially expressed genes from biological duplicates was performed using VAMPIRE at http://sasquatch.ucsd.edu/vampire/.

Accession Numbers

The GEO accession number for the full data sets (ChIP-seq and microarray) is GSE38103.

Example 2

VDR Prevents Liver Fibrosis

Figure 1A:
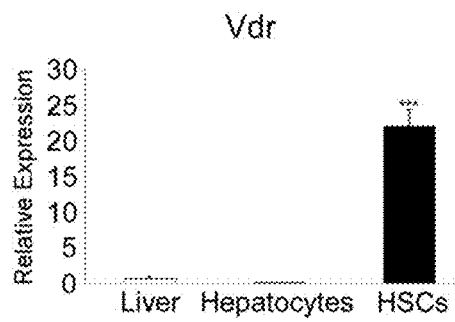
FIGS. 1A-1E. Specific Expression of Functional VDR in HSCs. (A) Relative VDR mRNA expression in murine liver, primary hepatocytes and HSCs (liver expression=1). Levels were quantified by RT-qPCR. Data represents the mean+/−SEM of at least three independent experiments performed in triplicate. Asterisks denote statistically significant differences (Student's t test, *p<0.001). (B) Western blot for VDR in protein lysates from samples in (A). (C) Freshly isolated primary murine HSCs were stained with VDR-specific antibody to monitor expression of VDR. DNA was visualized by DAPI stain. (D) and (E) Relative expression of CYP24A1 mRNA in primary murine HSCs (mHSCs) or LX-2 cells incubated with $1,25(OH)_2D_3$ or calcipotriol (Cal) for 16 hours at indicated concentrations, as measured by RT-qPCR (untreated HSC expression=1). Data represents the mean+/−SEM of at least three independent experiments performed in triplicate. Asterisks denote statistically significant differences (Student's t test, p<0.01, ***p<0.001).
Figure 1B:
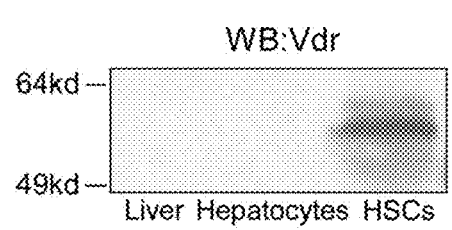
Figure 1D:
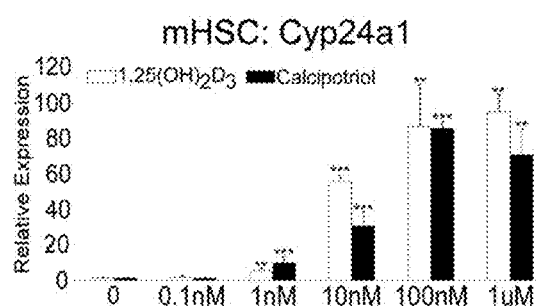
Figure 1C:
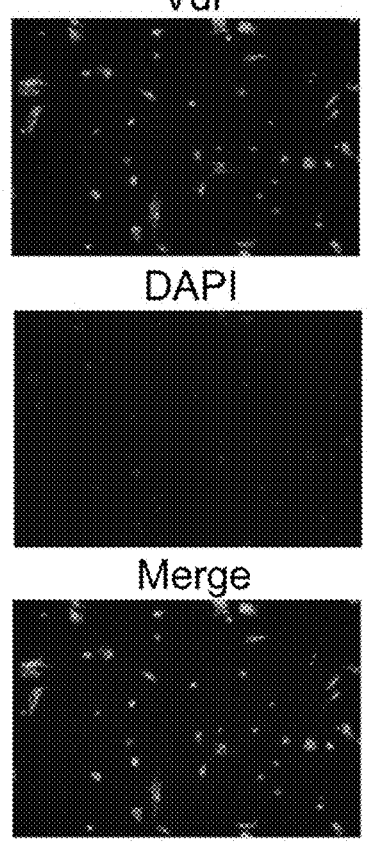
Figure 1E:
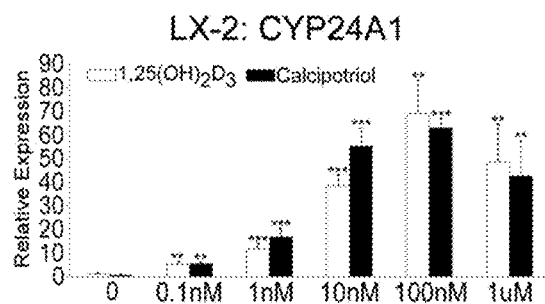

Consistent with previous results (Abramovitch et al., 2011; Gascon-Barre et al., 2003), it was observed that Vdr is expressed in HSCs but is not detectable in either whole liver or purified hepatocytes (FIGS. 1A-C). Moreover, the HSC-expressed VDR is fully functional as determined by ligand induction of CYP24A1 expression by either 1,25 $(OH)_2D_3$ or its low calcemic analogue, calcipotriol (Cal) (Nagpal et al., 2005) (FIG. 2A), in both primary HSCs and LX-2 cells, a well-established TGFβ1 responsive human HSC cell line (Xu et al., 2005) (FIGS. 1D and 1E).

To address whether VDR signaling could suppress fibrotic gene expression and counteract hepatic fibrogenesis in vivo, liver fibrosis was induced by carbon tetrachloride ($CCl_4$), a widely used hepatotoxic agent, at a dose of 0.5 ml/kg administered by intraperitoneal (IP) injection 3 times per week in wild type C57BL/6J mice. By four weeks, $CCl_4$-treated mice exhibited extensive liver bridging fibrosis with substantial collagen deposition, whereas $CCl_4$/calcipotriol-co-treated mice had a significant reduction in fibrosis as demonstrated by quantitation of Sirius red staining, hepatic hydroxyproline content and histological fibrotic scoring (FIGS. 3A-3D). The serum calcium concentration was not significantly altered by calcipotriol treatment (FIG. 2B). Examination of key fibrotic marker genes such as Col1a1, Tgfb1 and Timp1 revealed between 50-70% down-regulation by calcipotriol (FIGS. 3E-3G). Interestingly, when the mice were pre-treated with calcipotriol for 5 weeks prior to $CCl_4$/calcipotriol-co-treatment, the fibrogenic response in liver was nearly completely abrogated (FIGS. 2C-F), suggesting that the VDR agonist possesses not only the ability to attenuate fibrosis but also potential to proactively prevent liver fibrosis in vivo.

This led us to examine whether VDR deficiency could impact liver fibrogenesis. Indeed, 6 month-old $Vdr^{-/-}$ mice exhibited a spontaneous liver injury/fibrosis phenotype as demonstrated by increased collagen deposition with two of four mice developing frank cirrhosis (FIG. 3H, right/top) associated with hepatocyte necrosis and foci of necroinflammation surrounding portal tracts (FIG. 3H, right/bottom, arrow). As there was some variability in the degree of liver fibrosis observed using Sirius red staining of liver sections, liver hydroxyproline content was measured in the two $Vdr^{-/-}$ mice exhibiting the least fibrosis (non-cirrhotic mice) and still found to be significantly greater than that observed in either wild-type or $Vdr^{+/-}$ mice (FIG. 3I). Moreover, $Vdr^{+/-}$ mice exhibited multiple foci of peri-sinusoidal fibrosis in the absence of an inflammatory response (FIG. 3H, center/top, arrows), pathology not observed in control wild-type mice maintained on an identical calcium- and phosphate-supplemented diet (FIG. 3H, left). Histological findings were confirmed by quantitation of hepatic hydroxyproline content as well as examination of key fibrotic marker gene, Col1a1 (FIGS. 3I-3J).

These data indicate that both Vdr alleles are required for the maintenance of normal liver architecture and when completely abrogated, result in loss of control of the local inflammatory response in addition to dysregulation of fibrogenesis.

Example 3

VDR Signaling Suppresses TGFβ-Induced Pro-Fibrotic Genes

Expression profiling was used to explore the potential impact of VDR signaling in TGFβ1 and TGFβ1+1,25$(OH)_2D_3$-treated primary rat HSCs. Notably, 1,25$(OH)_2D_3$ treatment attenuated the culture-induced activation of HSCs, such that the transcriptome of treated cells closely resembled that of freshly isolated quiescent cells (FIG. 4A), and co-treatment of 1,25$(OH)_2D_3$ together with TGF 31 resulted in considerable repression of a large set of TGFβ1 induced genes (for complete list see Table S1 in Ding et al., Cell, 153:610-13, 2013, herein incorporated by reference, a shorter list is provided in Table 3 below).

TABLE 3

Top 50 TGFβ1 Induced Genes Suppressed by VDR Signaling

| TargetID | SYMBOL | Control. AVG_ | TGF beta. AVG | TGFb/ Control | VitD + TGFbetaTGFb/ TGFB + VitD3 | ACCESSION | DEFINITION |
|---|---|---|---|---|---|---|---|
| ILMN_63897 | Ms4g4a_predi | 3327 | 14356 | 4 | 810.7 | 17.7 XM_342027.1 | PREDICTED: *Rattus norvegicus* membrane-spanning 4-domains |
| ILMN_53895 | Ccr5 | 2069.5 | 4680.9 | 2 | 362.3 | 12.9 NM_053960.2 | *Rattus norvegicus* chemokine (C-C) receptor 5 (Ccr5) |
| ILMN_57751 | Chst1_predict | 1813.1 | 4284.5 | 2 | 337.6 | 12.7 XM_575178.1 | PREDICTED: *Rattus norvegicus* carbohydrate (keratan sulfate Gal-6) sulfotransferase 1 (predicted) (Chst1_predicted) |

TABLE 3-continued

Top 50 TGFβ1 Induced Genes Suppressed by VDR Signaling

| TargetID | SYMBOL | Control. AVG_ | TGF beta. AVG | TGFb/ Control | VitD + TGFbeta TGFB + VitD3 | TGFb/ TGFB + VitD3 | ACCESSION DEFINITION |
|---|---|---|---|---|---|---|---|
| ILMN_58099 | LOC499356 | 2562.8 | 3888.4 | 2 | 352.7 | 11.0 | XM_574689.1 PREDICTED: *Rattus norvegicus* similar to SH2-containing leukocyte protein 65 (LOC499356) |
| ILMN_67751 | LOC502907 | 1399.7 | 2318.7 | 2 | 241.9 | 9.6 | XM_578409.1 PREDICTED: *Rattus norvegicus* similar to immunoreceptor Ly49si1 (LOC502907) |
| ILMN_65374 | Oplah | 6494.5 | 16466 | 3 | 1922 | 8.6 | NM_053904.1 *Rattus norvegicus* 5-oxoprolinase (ATP-hydrolysing) (Oplah) |
| ILMN_67938 | Dcir3 | 6230.8 | 11228 | 2 | 1354 | 8.3 | XM_579150,1 PREDICTED: *Rattus norvegicus* dendritic cell inhibitory receptor 3 (Dclr3) |
| ILMN_69656 | Pcsk1 | 3330.8 | 6754.6 | 2 | 912.4 | 7.4 | NM_017091.1 *Rattus norvegicus* proprotein convertase subtilisin/kexin type 1 (Pcsk1) |
| ILMN_58952 | LOC304349 | 664 | 1503.8 | 2 | 211.1 | 7.1 | XM_221990.3 PREDICTED: *Rattus norvegicus* similar to cell surface receptor FDFACT (LOC304349) |
| ILMN_67493 | LOC502904 | 858.7 | 1425.7 | 2 | 213.6 | 6.7 | XM_578406.1 PREDICTED: *Rattus norvegicus* similar to immunoreceptor Ly49si3 (LOC502904) |
| ILMN_60514 | LOC366205 | 193.2 | 926.6 | 5 | 140.7 | 6.6 | XM_345441.2 PREDICTED: *Rattus norvegicus* similar to fibronectin leucine rich transmembrane protein 3 (LOC366205) |
| ILMN_63711 | Ms4a7_predict | 4402.2 | 10637 | 2 | 1708 | 6.2 | XM_215200.2 PREDICTED: *Rattus norvegicus* memrbrane-spanning 4-domains |
| ILMN_58064 | LOC498741 | 1156.2 | 1908.8 | 2 | 314.1 | 6.1 | XM_574019.1 PREDICTED: *Rattus norvegicus* similar to O-acyltransferase (membrane bound) domain containing 1 (LOC498741) |
| ILMN_63172 | Cacnb3 | 906.9 | 2511.6 | 3 | 415.9 | 6.0 | NM_012828.1 *Rattus norvegicus* calcium channel |
| ILMN_51438 | Emr1 | 831.7 | 1893.5 | 2 | 319.1 | 5.9 | XM_579174,1 PREDICTED: *Rattus norvegicus* EGF-like module containing |
| ILMN_54844 | Stab1_predict | 303.7 | 1141.2 | 4 | 204.7 | 5.6 | XM_214279.3 PREDICTED: *Rattus norvegicus* stabilin 1 (predicted) (Stab1_predicted) |
| ILMN_61533 | Ccl12_predicte | 597 | 1047.9 | 2 | 191.1 | 5.5 | XM_213425.2 PREDICTED: *Rattus norvegicus* chemokine (C-C motif) ligand 12 (predicted) (Ccl12_predicted) |
| ILMN_57542 | Pirb | 462.9 | 913.7 | 2 | 171.1 | 5.3 | NM_031713.1 *Rattus norvegicus* paired-tg-like receptor B (Pirb) |
| ILMN_63615 | Bmp2 | 954.6 | 1628.6 | 2 | 305 | 5.3 | NM_017178.1 *Rattus norvegicus* bone morphogenetic protein 2 (Bmp2) |
| ILMN_62796 | Ctsc | 16419.5 | 32328 | 2 | 6319 | 5.1 | NM_017097.1 *Rattus norvegicus* cathepsin C (Ctsc) |
| ILMN_51495 | Hod | 1297 | 2520.2 | 2 | 495.9 | 5.1 | NM_133621.2 *Rattus norvegicus* homeobox only domain (Hod) |
| ILMN_57423 | LOC498751 | 827.8 | 2611.8 | 3 | 516.6 | 5.1 | XM_574030.1 PREDICTED: *Rattus norvegicus* similar to RP23-462P2.7 (LOC498751) |
| ILMN_89162 | LOC497796 | 240.8 | 4341 | 18 | 859 | 5.1 | XM_579296.1 PREDICTED: *Rattus norvegicus* hypothetical gene supported by NM_001009496 (LOC497796) |
| ILMN_52068 | Ptpro | 5656.6 | 12798 | 2 | 2551 | 5.0 | NM_017336.1 *Rattus norvegicus* protein tyrosine phosphatase |
| ILMN_69714 | Gas7 | 1039.2 | 4083.5 | 4 | 832.8 | 4.9 | NM_053484.1 *Rattus norvegicus* growth arrest specific 7 (Gas7) |
| ILMN_58104 | Fchsd2_predic | 2632.5 | 7594.5 | 3 | 1565 | 4.9 | XM_216965.3 PREDICTED: *Rattus norvegicus* FCH and double SH3 domains 2 (predicted) (Fchsd2_predicted) |
| ILMN_52207 | Glipr1_predict | 3986 | 9174 | 2 | 1894 | 4.8 | XM_576223.1 PREDICTED: *Rattus norvegicus* GLI pathogenesis-related 1 (glioma) (predicted) (Glipr1_predicted) |
| ILMN_54794 | LOC310190 | 4496.5 | 12465 | 2 | 2594 | 4.8 | XM_226886.3 PREDICTED: *Rattus norvegicus* similar to hypothetical protein FLJ11127 (LOC310190) |
| ILMN_68980 | Ly49si1 | 261.1 | 622.8 | 2 | 134.7 | 4.6 | XM_579297.1 PREDICTED: *Rattus norvegicus* immunoreceptor Ly49si1 (Ly49si1) |
| ILMN_54950 | LOC501570 | 429.6 | 887.6 | 2 | 192.5 | 4.6 | XM_576974.1 PREDICTED: *Rattus norvegicus* similar to chromosome X open reading frame 21 (LOC501570) |
| ILMN_69073 | Ly49si2 | 538.9 | 1177 | 2 | 256 | 4.6 | XM_579296.1 PREDICTED: *Rattus norvegicus* immunoreceptor Ly49si2 (Ly49si2) |
| ILMN_68037 | Dcir2 | 426.1 | 842.9 | 2 | 184.9 | 4.6 | XM_579146.1 PREDICTED: *Rattus norvegicus* dendritic cell inhibitory receptor 2 (Dcir2) |
| ILMN_64162 | Ms4a6a_predi | 3823.9 | 7658.8 | 2 | 1696 | 4.5 | XM_215145.3 PREDICTED: *Rattus norvegicus* membrane-spanning 4-domain |
| ILMN_60323 | LOC499272 | 234.2 | 620 | 3 | 140.2 | 4.4 | XM_579937.1 PREDICTED: *Rattus norvegicus* LOC499272 (LOC499272) |
| ILMN_49166 | Sh3kbp1 | 4057.3 | 7133.8 | 2 | 1618 | 4.4 | NM_053360.2 *Rattus norvegicus* SH3-domain kinase binding protein 1 (Sh3kbp1) |
| ILMN_70030 | LOC366608 | 469.9 | 892.8 | 2 | 203.6 | 4.4 | XM_3456652 PREDICTED: *Rattus norvegicus* similar to mKIAA0716 protein (LOC366608) |
| ILMN_68422 | Cysltr1 | 429.3 | 801.8 | 2 | 183.5 | 4.4 | NM_053641.1 *Rattus norvegicus* cysteinyl leukotriene receptor 1 (Cysltr1) |
| ILMN_70002 | Cdh1 | 337.9 | 553.9 | 2 | 126.2 | 4.4 | NM_031334.1 *Rattus norvegicus* cadherin 1 (Cdh1) |
| ILMN_57625 | LOC312102 | 5658 | 19362 | 3 | 4469 | 4.3 | XM_231461.3 PREDICTED: *Rattus norvegicus* similar to hypothetical protein B230358A15 (LOC312102) |
| ILMN_67686 | Ms4a6b | 12345 | 21779 | 2 | 5158 | 4.2 | NM_00100697 *Rattus norvegicus* membrane-spanning 4-domains |
| ILMN_67607 | Slamf9_predic | 1044.7 | 1762.9 | 2 | 417.9 | 4.2 | XM_213932.2 PREDICTED: *Rattus norvegicus* SLAM family member 9 (predicted) (Slamf9_predicted) |

TABLE 3-continued

Top 50 TGFβ1 Induced Genes Suppressed by VDR Signaling

| TargetID | SYMBOL | Control. AVG_ | TGF beta. AVG | TGFb/ Control | VitD + TGFbetaTGFb/ TGFB + VitD3 | ACCESSION DEFINITION |
|---|---|---|---|---|---|---|
| ILMN_49493 | LOC499078 | 3963.4 | 9788.1 | 2 | 2325 | 4.2 XM_574362.1 PREDICTED: *Rattus norvegicus* similar to GP49B1 (LOC499076) |
| ILMN_54567 | Ptprc | 1582.3 | 2387 | 2 | 569.1 | 4.2 NM_138507.1 *Rattus norvegicus* protein tyrosine phosphatase |
| ILMN_60110 | RT1-Ba | 4721.8 | 13843 | 3 | 3390 | 4.1 XM_579226.1 PREDICTED: *Rattus norvegicus* RT1 class II |
| ILMN_62867 | LOC305269 | 288.8 | 687.8 | 2 | 170.6 | 4.0 XM_223309.3 PREDICTED: *Rattus norvegicus* similar to stem cell adaptor protein STAP-1 (predicted) (LOC305269) |
| ILMN_60864 | Dsipi | 1943.2 | 4575.5 | 2 | 1152 | 4.0 NM_031345.1 *Rattus norvegicus* delta sleep inducing peptide |
| ILMN_48333 | Nucb2 | 4712.3 | 10527 | 2 | 2733 | 3.9 NM_021663.2 *Rattus norvegicus* nucleobindin 2 (Nucb2) |
| ILMN_63522 | LOC499100 | 281.2 | 594.6 | 2 | 154.4 | 3.9 XM_218456.3 PREDICTED: *Rattus norvegicus* similar to doublesex and mab-3 related transcription factor 7 (LOC499100) |
| ILMN_55697 | Tmem26_pred | 457.8 | 912.3 | 2 | 237.3 | 3.8 XM_228106.3 PREDICTED: *Rattus norvegicus* transmembrane protein 26 (predicted) (Tmem26_predicted) |
| ILMN_54255 | LOC361899 | 557.1 | 1013.7 | 2 | 263.7 | 3.8 XM_341982.2 PREDICTED: *Rattus norvegicus* similar to CG15118-PB (predicted) (LOC361699) |

Figure 4B:
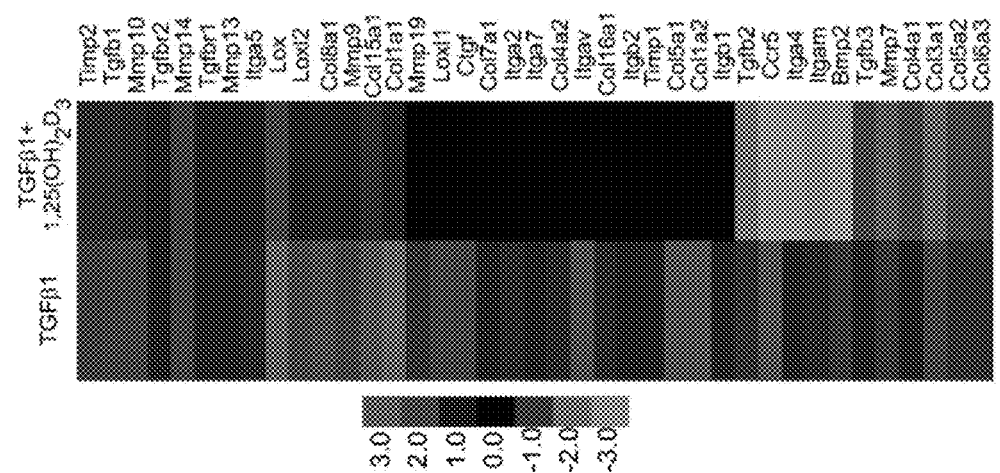
Figure 4A:
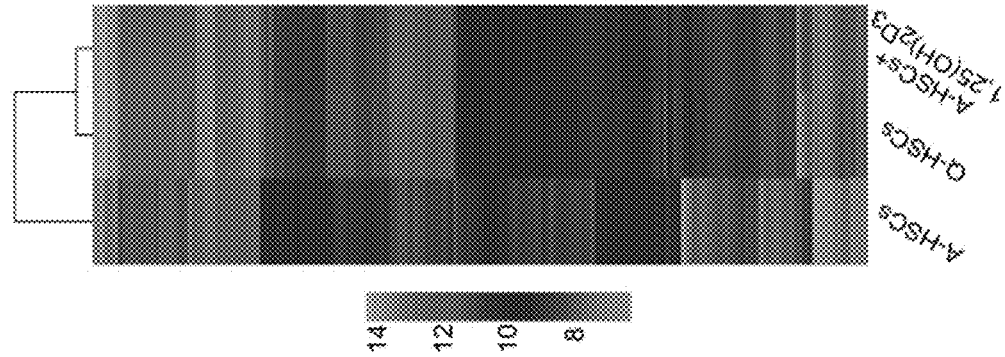

Among these, 39 genes were central to hepatic fibrogenesis, including collagens (Bataller and Brenner, 2005; Tsukada et al., 2006), Tgf superfamily members (Inagaki and Okazaki, 2007), matrix metalloproteinase family members (Mmps) (Arthur, 2000; Han, 2006), tissue inhibitors of metalloproteinase (Timps) (Arthur, 2000; Yoshiji et al., 2002), integrins (Patsenker and Stickel, 2011) and lysyl oxidase family members (Barry-Hamilton et al., 2011; Kagan and Li, 2003; Vadasz et al., 2005) (FIG. 4B).

Next, it was confirmed that in both primary mouse HSCs and LX-2 cells, calcipotriol potently repressed fibrotic gene expression, suggesting that the anti-TGFβ properties of VDR agonists are likely conserved across mammalian species (data not shown). Finally, using RNAi in LX-2 cells it was observed that loss of VDR abolished calcipotriol-mediated repression of TGFβ1 induced gene expression (FIG. 4C), collectively revealing that VDR regulates an anti-TGFβ/fibrotic network in vitro.

Example 4

Defining VDR and SMAD3 Cistromes in HSCs

This example describes methods used to determine whether VDR was a direct or indirect regulator of the anti-fibrotic gene network. As SMAD2 and SMAD3 are required for TGFβ1-induced pro-fibrotic gene expression in HSCs (FIG. 5A), and VDR activation did not significantly affect TGFβ1-induced phosphorylation and subsequent nuclear translocation of SMAD3 (FIG. 5B), a direct regulatory role for VDR was proposed. To explore this possibility, the genome-wide binding sites of VDR and SMAD3 were analyzed in LX-2 cells cultured with both calcipotriol and TGFβ1 using chromatin immunoprecipitation coupled with high-throughput deep sequencing (ChIP-Seq). The resulting cistromes identified 24,984 VDR and 23,581 SMAD3 high-confidence binding sites (FDR<0.0001) (FIGS. 6A and 6E). Consistent with the reported global binding pattern for other transcription factors (Barish et al., 2010; Biddie et al., 2011; Heinz et al., 2010; Trompouki et al., 2011), the majority of VDR and SMAD3 binding sites localize to distant intergenic and intronic regions, whereas only 16-21% are found at gene promoters (FIGS. 6A and 6E).

Figure 7A:
Figure 7B:
Figure 7C:
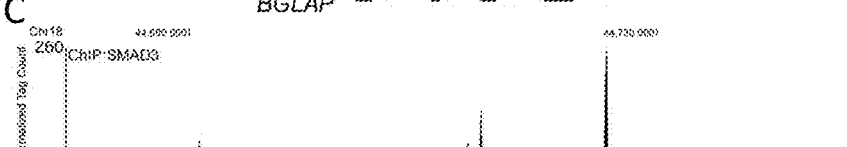
Figure 7D:
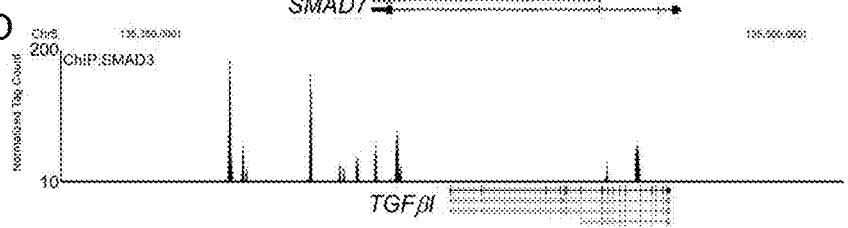

From the list of VDR and SMAD3 binding sites, a number of previously characterized functional vitamin D response elements (VDRE) were confirmed for known vitamin D-inducible genes such as CYP24A1 (FIG. 6B), SPP1, BGLAP (FIGS. 7A-7B), and SMAD-binding elements (SBE) for TGFβ signaling target genes including ID1 (FIG. 6F), SMAD7 and TGFβ1 (FIGS. 7C and 7D). Gene annotation analysis assigned peaks based on the proximity to the closest transcription start site and yielded 11,031 and 9,210 putative target genes within the individual VDR and SMAD3 cistromes, respectively. Gene ontology (GO) analysis of these annotated genes revealed that the most common classified functions for putative VDR and SMAD3 target genes were metabolism (47%) and cell signaling (34%) (FIGS. 6C and 6G).

Finally, the most significantly enriched binding motifs for VDR and SMAD3 were interrogated. Among these sequence signatures, a direct hexamer repeat with a 3 bp spacer (DR3) consensus sequence was the most enriched motif at VDR sites, explaining 74% of VDR binding peaks (FIG. 6D, top), while the consensus SBE sequence, a GTCT motif, accounted for 83% of SMAD3 binding peaks (FIG. 6H, top). Interestingly, the analysis revealed that the GTCT and DR3-type motifs are also co-enriched within nucleosomal distance at VDR and SMAD3 binding sites, respectively, suggesting VDR and SMAD3 communicate via intersecting cistromes (FIGS. 6D and 6H, bottom).

Example 5

Antagonism of TGFβ Signaling Via VDR/SMAD3 Genomic Crosstalk

To address this possibility, bioinformatic analysis was used to quantify the extent of cistrome intersection by calculating the number of sites bound by both VDR and SMAD3. A total of 10,436 genomic sites were co-occupied (FIG. 8A), and the co-occupancy pattern is genome-wide as visualized by a heatmap quantifying VDR sites surrounding SMAD3 binding peaks (FIG. 8B). If this genomic intersection mediates VDR/SMAD3 crosstalk, VDR and SMAD3 could interact with their co-occupied sites simultaneously. Sequential ChIP (ChIP-re-ChIP) experiments confirmed that VDR and SMAD3 can, at least transiently, co-occupy the same genomic sites (FIG. 8C).

Next, if anti-TGFβ signaling is mediated by a VDR/SMAD genomic intersection, then pro-fibrotic genes in HSCs should be overrepresented in jointly-bound regulatory elements. Indeed, GO analysis designating human phenotypes showed significant enrichment of "abnormal scarring" response (67%) for loci co-occupied by VDR and SMAD3 (FIG. 8D) leading to an examination of the potential VDR/SMAD3 co-occupancy with the earlier identified 39 pro-fibrotic genes (FIG. 4B). Within this subset, 34 were found to contain VDR/SMAD3 co-occupied sites (FIG. 8E). Furthermore, many of these genes were found to contain multiple VDR/SMAD3 co-occupied sites (FIG. 8F & Table 4).

9B), further supporting the possibility of genomic antagonism by proximal DNA binding (Barish et al., 2010; Hua et al., 2009).

The presence of VDR/SMAD genomic antagonism can be visualized by plotting the average ChIP-Seq signal intensity of VDR and SMAD3 to the center of their co-occupied sites. This demonstrated that, in the presence of calcipotriol, TGFβ-induced recruitment of SMAD3 was globally compromised by ~1.5 fold, whereas binding of VDR to these sites was globally enhanced by nearly 10 fold (FIGS.

TABLE 3

Fibrotic Genes Coregulated by VDR and SMAD

| TargetID | Symbol | Control Avg Signal | TGFβ Avg Signal | VitD + TGFβ Avg Signal | Accession | VDR/SMAD co-bound sites |
|---|---|---|---|---|---|---|
| ILMN_70153 | Lox | 2260.8 | 7481.1 | 4219.9 | XM_579391.1 | 1 |
| ILMN_55682 | Loxl2 | 495.5 | 966.5 | 597.0 | XM_214225.3 | 2 |
| ILMN_68993 | Loxl1 | 537.2 | 1045.1 | 560.1 | XM_576419.1 | 1 |
| ILMN_48683 | Ctgf | 10532.3 | 20216.0 | 9730.1 | NM_022266.1 | 3 |
| ILMN_53895 | Ccr5 | 2069.5 | 4680.9 | 362.3 | NM_053960.2 | 0 |
| ILMN_62559 | Timp1 | 10124.0 | 13471.4 | 9101.3 | NM_053819.1 | 2 |
| ILMN_55617 | Timp2 | 500.7 | 913.0 | 751.7 | NM_021989.2 | 3 |
| ILMN_51699 | Tgfb1 | 2922.5 | 5480.4 | 4391.0 | NM_021578.1 | 4 |
| ILMN_69134 | Tgfb2 | 814.7 | 1308.4 | 388.0 | NM_031131.1 | 10 |
| ILMN_65300 | Tgfb3 | 226.4 | 288.5 | 178.6 | NM_013174.1 | 1 |
| ILMN_65380 | Tgfbr1 | 277.1 | 365.1 | 331.9 | NM_012775.1 | 2 |
| ILMN_53807 | Tgfbr2 | 289.0 | 347.6 | 358.9 | NM_031132.1 | 9 |
| ILMN_56722 | Mmp10 | 561.7 | 1042.3 | 764.6 | NM_133514.1 | 1 |
| ILMN_64191 | Mmp13 | 150.8 | 202.4 | 180.0 | XM_343345.2 | 2 |
| ILMN_62465 | Mmp14 | 8370.4 | 15560.3 | 14980.5 | NM_031056.1 | 1 |
| ILMN_52716 | Mmp19 | 319.6 | 516.3 | 308.7 | XM_222317.3 | 1 |
| ILMN_67641 | Mmp7 | 277.3 | 469.3 | 164.9 | NM_012864.1 | 1 |
| ILMN_66838 | Mmp9 | 2153.3 | 4197.3 | 2676.4 | NM_031055.1 | 1 |
| ILMN_68793 | Itga2 | 188.5 | 257.9 | 204.2 | XM_345156.2 | 5 |
| ILMN_53120 | Itga4 | 1128.4 | 1464.4 | 380.6 | XM_230033.3 | 0 |
| ILMN_59997 | Itga5 | 880.0 | 1227.3 | 1158.1 | XM_235707.3 | 3 |
| ILMN_50763 | Itga7 | 170.2 | 202.7 | 161.9 | NM_030842.1 | 0 |
| ILMN_49475 | Itgam | 1689.7 | 2297.0 | 658.0 | NM_012711.1 | 1 |
| ILMN_53994 | Itgav | 2145.1 | 4760.5 | 2417.2 | XM_230950.3 | 0 |
| ILMN_63152 | Itgb1 | 8050.9 | 10104.2 | 7987.9 | NM_017022.1 | 9 |
| ILMN_67791 | Itgb2 | 4506.5 | 5580.6 | 4858.4 | XM_228072.3 | 1 |
| ILMN_50271 | Col15a1 | 257.9 | 616.4 | 396.9 | XM_216399.3 | 4 |
| ILMN_67754 | Col16al | 175.4 | 237.2 | 173.3 | XM_345584.2 | 3 |
| ILMN_50637 | Col1a1 | 474.2 | 1429.1 | 557.9 | XM_213440.3 | 3 |
| ILMN_52596 | Col1a2 | 10691.1 | 24123.0 | 9593.3 | NM_053356.1 | 3 |
| ILMN_66092 | Col3a1 | 513.9 | 965.1 | 287.6 | NM_032085.1 | 1 |
| ILMN_63763 | Col4a1 | 1708.1 | 2261.0 | 1315.2 | XM_214400.3 | 3 |
| ILMN_63579 | Col4a2 | 162.6 | 225.3 | 166.2 | XM_225043.3 | 5 |
| ILMN_50151 | Col5a1 | 611.1 | 1418.9 | 673.0 | NM_134452.1 | 8 |
| ILMN_51080 | Col5a2 | 2181.0 | 3452.2 | 1696.8 | XM_343564.2 | 9 |
| ILMN_66976 | Col6a3 | 526.5 | 848.2 | 442.6 | XM_346073.2 | 9 |
| ILMN_51937 | Col7a1 | 185.8 | 229.6 | 190.3 | XM_238554.3 | 1 |
| ILMN_70226 | Col8a1 | 574.2 | 1285.9 | 773.5 | XM_221536.3 | 6 |
| ILMN_63615 | Bmp2 | 954.6 | 1628.6 | 305.0 | NM_017178.1 | 0 |

Luciferase reporter plasmids bearing VDR/SMAD3 co-bound sites on the COL1A1 gene were generated, and it was observed that these genomic elements could at least partially recapitulate the opposing actions of calcipotriol and TGFβ1, indicating that these cis-elements function as enhancers of pro-fibrotic gene expression (FIG. 9A).

Example 6

VDR/SMAD Genomic Antagonism

Informatic analysis of the spatial relationships between VDR and SMAD3 in co-occupied genomic regions confirm that their respective response elements were co-localized within one nucleosomal window (<200 base pairs) (FIG. 10A-10B). In addition, the proposed genomic antagonism was illustrated by examining its impact along a pro-fibrotic gene harbouring VDR/SMAD co-occupied regulatory elements such as COL1A1. Visualization of sequencing tracks revealed that calcipotriol promoted VDR occupancy at all three major VDR/SMAD3 co-bound sites on the COL1A1 gene (FIG. 10C, middle 2 tracks). In contrast, TGFβ-induced SMAD3 binding was typically diminished along the gene upon calcipotriol treatment (FIG. 10C, top 2 tracks, and independently validated by ChIP-qPCR, FIGS. 10D and 10F). Similar loss of SMAD3 coupled with VDR recruitment was also observed at the regulatory regions of other pro-fibrotic genes such as COL1A2, TGFB1, TGFB2, TIMP1, TIMP2 and LOXL2 (FIGS. 11A-F). Furthermore, RNAi-mediated depletion of VDR and SMAD2/3 abrogated the calcipotriol-dependent loss of SMAD3 recruitment and TGFβ1-induced VDR binding to co-occupied regulatory elements respectively, demonstrating VDR and SMADs are required to mediate this genomic antagonism (FIGS. 10E and 10G).

Since recruitment of histone-modifying cofactors such as CBP and p300 and hyperacetylation of histone H3 have been established as landmark events of activation of TGFβ signaling (Massague et al., 2005), it was determined whether VDR/SMAD genomic antagonism could restrain TGFβ signaling by interfering with this epigenetic pathway. The status of histone H3 acetylation as well as recruitment of CBP and p300 to VDR/SMAD co-occupied sites was examined in cells treated with either calcipotriol or TGFβ1 or both. ChIP-qPCR demonstrated that TGFβ1 induced recruitment of p300 and CBP and histone H3 hyperacetylation at the VDR/SMAD co-occupied regulatory region of COL1A1. This effect was lost in cells co-treated with calcipotriol and TGFβ1 (FIG. 12A), indicating that VDR/SMAD genomic antagonism limits TGFβ activation by compromising coactivator recruitment and histone hyperacetylation.

Ligand-dependent corepressor recruitment or "transrepression" has been proposed as the major mechanism for nuclear receptors such as PPARγ and LXR to negatively regulate inflammatory gene expression (Glass and Saijo, 2010). To test whether transrepression contributes to the antagonism, potential induced recruitment of co-repressors was examined including NCoR, SMRT, HDAC3, CoREST, LSD1, and G9a to VDR/SMAD3 co-occupied regulatory regions of pro-fibrotic genes such as COL1A1 and COL1A2 in response to calcipotriol and TGFβ1. However, altered binding of these corepressors to these sites was not detected (FIG. 12B), indicating that the loss of transcriptional activation complexes from these sites is not due to increased co-repressor recruitment.

Example 7

TGFβ Unmasks a Signal Dependent VDR Cistrome

While establishing VDR/SMAD3 genomic antagonism, it was observed that TGFβ/SMAD signaling appears to enhance liganded VDR recruitment to the cis-regulatory regions of COL1A1 (FIGS. 10F and 10G). To determine whether this effect is observed at other VDR binding sites of pro-fibrotic genes, the VDR cistrome±calcipotriol was analyzed in the presence and absence of TGFβ1. It was observed that TGFβ1 promotes binding of liganded, but not unliganded VDR to cis-regulatory regions at all pro-fibrotic genes (FIGS. 11B & 11A-F, lower 4 tracks).

Next, calcipotriol-induced VDR global binding patterns were compared in the presence or absence of TGFβ1. While 6,281 binding sites comprise the de novo VDR cistrome in the absence of TGFB31, a new cistrome comprised of 24,984 sites was induced in the presence of TGFβ1 (FIG. 6A). Interestingly, only 3,537 sites were shared by both cistromes and 85% (21,447 sites) of the TGFβ-induced liganded VDR binding sites were unique (FIG. 13A), indicating that TGFβ results in a dramatic shift of genome-wide binding locations of liganded VDR.

Comparative studies of the two VDR cistromes revealed that TGFβ1+calcipotriol sites (but not calcipotriol-only sites) were highly enriched at SMAD3 binding sites (FIG. 13B). Moreover, binding of VDR to these genomic sites was enhanced by TGFβ signaling (FIG. 13C) and this effect was not likely due to a change of VDR expression (FIG. 13D).

The DNA sequences of different subsets of VDR genomic loci were examined, and it was observed that more than 70% contain de novo VDR regulatory sites (FIG. 13E), indicating that VDR acts directly on the DNA, as opposed to SMAD-dependent tethering. Interestingly, TGFβ induced significant depletion of nucleosomes at VDR-SMAD3 co-bound sites (FIG. 13F), indicating TGFβ-SMAD signaling may promote binding of VDR to its adjacent sites by potentiating local chromatin remodelling and resultant accessibility.

Example 8

The Genomic Circuit Between VDR and SMAD

The findings discussed above suggest a dynamic relationship between VDR and TGFβ-SMAD signaling: perhaps, TGFβ induction of SMAD binding to chromatin creates a new genomic landscape that now becomes accessible to liganded VDR which could enable temporally delayed SMAD repression. To explore this spatio-temporal relationship, the kinetics of SMAD3 and VDR recruitment to co-occupied cis-regulatory elements of fibrotic genes (such as COL1A1) was determined in the presence of either calcipotriol or TGFβ1 or both. Specifically, ChIP-qPCR was employed to monitor binding of VDR and SMAD3 to the cis-regulatory region of COL1A1 at multiple time points (0, 1, 2, 4, 6, 16 hours).

Notably, binding of both liganded VDR and SMAD3 to this site were maximally promoted by TGFβ1 after 4 hours of treatment, followed by a gradual decrease to basal levels after 16 hours (FIGS. 14A-14B), confirming the role of TGFβ1 in facilitating recruitment of VDR to chromatin. Interestingly, the binding curve of SMAD3 upon TGFβ1 stimulation was dramatically shifted by the presence of calcipotriol, with the maximum binding of SMAD3 observed just 1 hour post-TGFβ1 treatment. After 4 hours, SMAD3 recruitment was significantly reduced by 70% (FIG. 14B). Furthermore, normalization of VDR and SMAD3 binding in the presence of both calcipotriol and TGFB31 to their basal levels revealed that the occupancy of VDR and SMAD3 were inversely correlated (FIG. 14C), indicating that TGFβ-induced chromatin accessibility produces a genomic architecture that facilitates VDR to reverse SMAD activation. Together, this VDR/SMAD genomic circuit provides a chromatin based mechanism for VDR to block fibrosis by antagonizing TGFβ signaling in HSCs.

REFERENCES

Abramovitch et al. (2011). Vitamin D inhibits proliferation and profibrotic marker expression in hepatic stellate cells and decreases thioacetamide-induced liver fibrosis in rats. Gut 60, 1728-1737.

Agmon-Levin et al. (2012). Vitamin D in Systemic and Organ-Specific Autoimmune Diseases. Clin Rev Allergy Immunol 2012, 14.

Amling, et al. (1999). Rescue of the skeletal phenotype of vitamin D receptor-ablated mice in the setting of normal mineral ion homeostasis: formal histomorphometric and biomechanical analyses. Endocrinology 140, 4982-4987.

Arthur, M. J. (2000). Fibrogenesis II. Metalloproteinases and their inhibitors in liver fibrosis. Am J Physiol Gastrointest Liver Physiol 279, G245-249.

Barish et al. (2005). A Nuclear Receptor Atlas: macrophage activation. Mol Endocrinol 19, 2466-2477. Epub 25 Jul. 2428.

Barish et al. (2010). Bcl-6 and NF-kappaB cistromes mediate opposing regulation of the innate immune response. Genes Dev 24, 2760-2765.

Barry-Hamilton et al. (2011). Allosteric inhibition of lysyl oxidase-like-2 impedes the development of a pathologic microenvironment. Nat Med 16, 1009-1017.

Bataller, R., and Brenner, D. A. (2005). Liver fibrosis. *J Clin Invest* 115, 209-218.

Baur, et al. (2011). Combined effect of 25-OH vitamin D plasma levels and genetic Vitamin D Receptor (NR 1I1) variants on fibrosis progression rate in HCV patients. Liver Int.

Biddie et al. (2011). Transcription factor AP1 potentiates chromatin accessibility and glucocorticoid receptor binding. Mol Cell 43, 145-155.

Bookout et al. (2006). Anatomical profiling of nuclear receptor expression reveals a hierarchical transcriptional network. Cell 126, 789-799.

Bouillon et al. (2008). Vitamin D and human health: lessons from vitamin D receptor null mice. Endocr Rev 29, 726-776.

Bouwens et al. (1992). Liver cell heterogeneity: functions of non-parenchymal cells. Enzyme 46, 155-168.

Breitkopf, K., Godoy, P., Ciuclan, L., Singer, M. V., and Dooley, S. (2006). TGF-beta/Smad signaling in the injured liver. Z Gastroenterol 44, 57-66.

Chawla et al. (2001). Nuclear receptors and lipid physiology: opening the X-files. Science 294, 1866-1870.

Cohen-Naftaly and Friedman (2011). Current status of novel antifibrotic therapies in patients with chronic liver disease. Therap Adv Gastroenterol 4, 391-417.

Ding et al. (2008). Mediator links epigenetic silencing of neuronal gene expression with x-linked mental retardation. Mol Cell 31, 347-359.

Feng and Derynck (2005). Specificity and versatility in tgf-beta signaling through Smads. Annu Rev Cell Dev Biol 21, 659-693.

Friedman, S. L. (1993). Seminars in medicine of the Beth Israel Hospital, Boston.

The cellular basis of hepatic fibrosis. Mechanisms and treatment strategies. N Engl J Med 328, 1828-1835.

Friedman, S. L. (1999). Evaluation of fibrosis and hepatitis C. Am J Med 107, 27S-30S.

Friedman, S. L. (2003). Liver fibrosis—from bench to bedside. J Hepatol 38 Suppl 1, S38-53.

Friedman, S. L. (2008). Hepatic stellate cells: protean, multifunctional, and enigmatic cells of the liver. Physiol Rev 88, 125-172.

Friedman, S. L., and Bansal, M. B. (2006). Reversal of hepatic fibrosis—fact or fantasy? Hepatology 43, S82-88.

Friedman, S. L., Roll, F. J., Boyles, J., and Bissell, D. M. (1985). Hepatic lipocytes: the principal collagen-producing cells of normal rat liver. Proc Natl Acad Sci USA 82, 8681-8685.

Gascon-Barre et al. (2003). The normal liver harbors the vitamin D nuclear receptor in nonparenchymal and biliary epithelial cells. Hepatology 37, 1034-1042.

Geerts, A. (2001). History, heterogeneity, developmental biology, and functions of quiescent hepatic stellate cells. Semin Liver Dis 21, 311-335.

Glass, C. K., and Saijo, K. (2010). Nuclear receptor transrepression pathways that regulate inflammation in macrophages and T cells. Nat Rev Immunol 10, 365-376.

Goltzman et al. (2004). Effects of calcium and of the Vitamin D system on skeletal and calcium homeostasis: lessons from genetic models. J Steroid Biochem Mol Biol 89-90, 485-489.

Griffin et al. (2001). Dendritic cell modulation by 1alpha,25 dihydroxyvitamin D3 and its analogs: a vitamin D receptor-dependent pathway that promotes a persistent state of immaturity in vitro and in vivo. Proc Natl Acad Sci USA 98, 6800-6805. Epub 2001 May 6822.

Han et al. (2010). A novel bile acid-activated vitamin D receptor signaling in human hepatocytes. Mol Endocrinol 24, 1151-1164.

Han, Y. P. (2006). Matrix metalloproteinases, the pros and cons, in liver fibrosis. J Gastroenterol Hepatol 21 Suppl 3, S88-91.

Heinz et al. (2010). Simple combinations of lineage-determining transcription factors prime cis-regulatory elements required for macrophage and B cell identities. Mol Cell 38, 576-589.

Hendriks et al. (1985). Perisinusoidal fat-storing cells are the main vitamin A storage sites in rat liver. Exp Cell Res 160, 138-149.

Hernandez-Gea, V., and Friedman, S. L. (2011). Pathogenesis of liver fibrosis. Annu Rev Pathol 6, 425-456.

Hua et al. (2009). Genomic antagonism between retinoic acid and estrogen signaling in breast cancer. Cell 137, 1259-1271.

Inagaki, Y., and Okazaki, I. (2007). Emerging insights into Transforming growth factor beta Smad signal in hepatic fibrogenesis. Gut 56, 284-292.

Janssens, W., Mathieu, C., Boonen, S., and Decramer, M. (2011). Vitamin D deficiency and chronic obstructive pulmonary disease: a vicious circle. Vitam Horm 86, 379-399.

Kagan, H. M., and Li, W. (2003). Lysyl oxidase: properties, specificity, and biological roles inside and outside of the cell. J Cell Biochem 88, 660-672.

Kim et al. (2002). Burden of liver disease in the United States: summary of a workshop. Hepatology 36, 227-242.

Knook et al. (1982). Fat-storing cells of the rat liver. Their isolation and purification. Exp Cell Res 139, 468-471.

Lee, U. E., and Friedman, S. L. (2011). Mechanisms of hepatic fibrogenesis. Best Pract Res Clin Gastroenterol 25, 195-206.

Li, M. O., and Flavell, R. A. (2008). TGF-beta: a master of all T cell trades. Cell 134, 392-404.

Li, Y. C., Pirro, A. E., Amling, M., Delling, G, Baron, R., Bronson, R., and Demay, M. B. (1997). Targeted ablation of the vitamin D receptor: an animal model of vitamin D-dependent rickets type II with alopecia. Proc Natl Acad Sci USA 94, 9831-9835.

Lim, L. Y., and Chalasani, N. (2012). Vitamin d deficiency in patients with chronic liver disease and cirrhosis. Curr Gastroenterol Rep 14, 67-73.

Makishima et al. (2002). Vitamin D receptor as an intestinal bile acid sensor. Science 296, 1313-1316.

Massague, J. (2008). TGFbeta in Cancer. Cell 134, 215-230.

Massague et al. (2005). Smad transcription factors. Genes Dev 19, 2783-2810.

Munger et al. (2006). Serum 25-hydroxyvitamin D levels and risk of multiple sclerosis. Jama 296, 2832-2838.

Nagpal, S., Na, S., and Rathnachalam, R. (2005). Noncalcemic actions of vitamin D receptor ligands. Endocr Rev 26, 662-687.

Patsenker, E., and Stickel, F. (2011). Role of integrins in fibrosing liver diseases. Am J Physiol Gastrointest Liver Physiol 301, G425-434.

Petta et al. (2010). Low vitamin D serum level is related to severe fibrosis and low responsiveness to interferon-based therapy in genotype 1 chronic hepatitis C. Hepatology 51, 1158-1167.

Ramagopalan et al. (2011). Rare variants in the CYP27B1 gene are associated with multiple sclerosis. Ann Neurol 70, 881-886.

Reynaert et al. (2002). Hepatic stellate cells: role in microcirculation and pathophysiology of portal hypertension. Gut 50, 571-581.

Rosenbloom et al. (2010). Narrative review: fibrotic diseases: cellular and molecular mechanisms and novel therapies. Ann Intern Med 152, 159-166.

Seki et al. (2007). TLR4 enhances TGF-beta signaling and hepatic fibrosis. Nat Med 13, 1324-1332.

Seki, E., and Schnabl, B. (2012). Role of innate immunity and the microbiota in liver fibrosis: crosstalk between the liver and gut. J Physiol 590, 447-458.

Siegmund et al. (2005). Molecular mechanisms of alcohol-induced hepatic fibrosis. Dig Dis 23, 264-274.

Tanaka et al. (2009). Vitamin D receptor polymorphisms are associated with increased susceptibility to primary biliary cirrhosis in Japanese and Italian populations. J Hepatol 50, 1202-1209.

Terrier et al. (2011). Low 25-OH vitamin D serum levels correlate with severe fibrosis in HIV-HCV co-infected patients with chronic hepatitis. J Hepatol 55, 756-761.

Trompouki et al. (2011). Lineage regulators direct BMP and Wnt pathways to cell-specific programs during differentiation and regeneration. Cell 147, 577-589.

Tsukada et al. (2006). Mechanisms of liver fibrosis. Clin Chim Acta 364, 33-60.

Vadasz et al. (2005). Abnormal deposition of collagen around hepatocytes in Wilson's disease is associated with hepatocyte specific expression of lysyl oxidase and lysyl oxidase like protein-2. J Hepatol 43, 499-507.

von Essen et al. (2010). Vitamin D controls T cell antigen receptor signaling and activation of human T cells. Nat Immunol 11, 344-349.

Williams, R. (2006). Global challenges in liver disease. Hepatology 44, 521-526.

Wynn, T. A. (2008). Cellular and molecular mechanisms of fibrosis. J Pathol 214, 199-210.

Xu et al. (2005). Human hepatic stellate cell lines, LX-1 and LX-2: new tools for analysis of hepatic fibrosis. Gut 54, 142-151.

Yoshiji et al. (2002). Tissue inhibitor of metalloproteinases-1 attenuates spontaneous liver fibrosis resolution in the transgenic mouse. Hepatology 36, 850-860.

In view of the many possible embodiments to which the principles of the disclosure may be applied, it should be recognized that the illustrated embodiments are only examples of the invention and should not be taken as limiting the scope of the invention. Rather, the scope of the disclosure is defined by the following claims. We therefore claim as our invention all that comes within the scope and spirit of these claims.

We claim:

1. A method for treating pancreatic fibrosis in a subject, comprising:
   administering to the subject a therapeutically effective amount of a composition comprising
   a nanoparticle comprising retinyl palmitate on its surface, and
   calcipotriol, which is in or attached to the nanoparticle, thereby treating the pancreatic fibrosis in the subject.

2. The method of claim 1, wherein the administering comprises orally administering the therapeutically effective amount of the composition into the subject.

3. The method of claim 1, wherein the administering comprises intravenously, intrathecally, intramuscularly, intraperitoneally, intra-articularly, intratumorally, or subcutaneously administering a therapeutically effective amount of the composition into the subject.

4. The method of claim 1, wherein the subject is a human subject.

5. The method of claim 1, wherein the subject is a mammalian subject.

* * * * *

UNITED STATES PATENT AND TRADEMARK OFFICE
CERTIFICATE OF CORRECTION

PATENT NO. : 9,872,866 B2
APPLICATION NO. : 14/921230
DATED : January 23, 2018
INVENTOR(S) : Ding et al.

Page 1 of 1

It is certified that error appears in the above-identified patent and that said Letters Patent is hereby corrected as shown below:

On the Title Page

Item (72) Inventors, should read:
-- (72) Inventors: Ning Ding, Riverside, CA (US);
Michael Downes, San Diego, CA (US);
Christopher Liddle, Tura Beach, NSW (AU);
Ronald M. Evans, La Jolla, CA (US);
Nanthakumar Subramaniam, Wentworthville, NSW (AU) --.

Signed and Sealed this
Eighteenth Day of June, 2019

Andrei Iancu
*Director of the United States Patent and Trademark Office*

SEQUENCE LISTING

```
<160> NUMBER OF SEQ ID NOS: 34

<210> SEQ ID NO 1
<211> LENGTH: 24
<212> TYPE: DNA
<213> ORGANISM: Mus musculus

<400> SEQUENCE: 1
tcaacagcaa ctcccactct tcca                                          24

<210> SEQ ID NO 2
<211> LENGTH: 24
<212> TYPE: DNA
<213> ORGANISM: Mus musculus

<400> SEQUENCE: 2
ttgtcattga gagcaatgcc agcc                                          24

<210> SEQ ID NO 3
<211> LENGTH: 20
<212> TYPE: DNA
<213> ORGANISM: Mus musculus

<400> SEQUENCE: 3
gctgaacctc catgaggaag                                               20

<210> SEQ ID NO 4
<211> LENGTH: 20
<212> TYPE: DNA
<213> ORGANISM: Mus musculus

<400> SEQUENCE: 4
ggatcatctt ggcgtagagc                                               20

<210> SEQ ID NO 5
<211> LENGTH: 24
```

```
<212> TYPE: DNA
<213> ORGANISM: Mus musculus

<400> SEQUENCE: 5
gaccgcaaac agcttgatgt ggat                                          24

<210> SEQ ID NO 6
<211> LENGTH: 24
<212> TYPE: DNA
<213> ORGANISM: Mus musculus

<400> SEQUENCE: 6
atattcctca catcttccgc ccgt                                          24

<210> SEQ ID NO 7
<211> LENGTH: 24
<212> TYPE: DNA
<213> ORGANISM: Mus musculus

<400> SEQUENCE: 7
actgcaacat ggagacaggt caga                                          24

<210> SEQ ID NO 8
<211> LENGTH: 24
<212> TYPE: DNA
<213> ORGANISM: Mus musculus

<400> SEQUENCE: 8
atcggtcatg ctctctccaa acca                                          24

<210> SEQ ID NO 9
<211> LENGTH: 24
<212> TYPE: DNA
<213> ORGANISM: Mus musculus

<400> SEQUENCE: 9
tttggagcct ggacacacag taca                                          24

<210> SEQ ID NO 10
<211> LENGTH: 24
<212> TYPE: DNA
<213> ORGANISM: Mus musculus

<400> SEQUENCE: 10
tgtgttggtt gtagagggca agga                                          24

<210> SEQ ID NO 11
<211> LENGTH: 24
<212> TYPE: DNA
<213> ORGANISM: Mus musculus

<400> SEQUENCE: 11
ggtgtgcaca gtgtttccct gttt                                          24

<210> SEQ ID NO 12
<211> LENGTH: 24
<212> TYPE: DNA
<213> ORGANISM: Mus musculus

<400> SEQUENCE: 12
tccgtccaca aacagtgagt gtca                                          24

<210> SEQ ID NO 13
```

```
<211> LENGTH: 22
<212> TYPE: DNA
<213> ORGANISM: Homo sapiens

<400> SEQUENCE: 13
gcagtgatgt aaaatttctt gg                                              22

<210> SEQ ID NO 14
<211> LENGTH: 23
<212> TYPE: DNA
<213> ORGANISM: Homo sapiens

<400> SEQUENCE: 14
aaagctcggt tttactcttc aca                                             23

<210> SEQ ID NO 15
<211> LENGTH: 20
<212> TYPE: DNA
<213> ORGANISM: Homo sapiens

<400> SEQUENCE: 15
ctgtggcaac caagactaca                                                 20

<210> SEQ ID NO 16
<211> LENGTH: 20
<212> TYPE: DNA
<213> ORGANISM: Homo sapiens

<400> SEQUENCE: 16
cccacctgga acttgatgag                                                 20

<210> SEQ ID NO 17
<211> LENGTH: 21
<212> TYPE: DNA
<213> ORGANISM: Homo sapiens

<400> SEQUENCE: 17
cctgctgcag attctctgga a                                               21

<210> SEQ ID NO 18
<211> LENGTH: 21
<212> TYPE: DNA
<213> ORGANISM: Homo sapiens

<400> SEQUENCE: 18
agggtgtcgt gctgtttctt g                                               21

<210> SEQ ID NO 19
<211> LENGTH: 24
<212> TYPE: DNA
<213> ORGANISM: Homo sapiens

<400> SEQUENCE: 19
accgaaggca gacggtaaca agta                                            24

<210> SEQ ID NO 20
<211> LENGTH: 24
<212> TYPE: DNA
<213> ORGANISM: Homo sapiens

<400> SEQUENCE: 20
gacatgcttg agcaacgcac tgaa                                            24
```

```
<210> SEQ ID NO 21
<211> LENGTH: 24
<212> TYPE: DNA
<213> ORGANISM: Homo sapiens

<400> SEQUENCE: 21
atgtcaacag gaatgcagca gtgg                                          24

<210> SEQ ID NO 22
<211> LENGTH: 24
<212> TYPE: DNA
<213> ORGANISM: Homo sapiens

<400> SEQUENCE: 22
atagcgctgg ttacagttgg gaga                                          24

<210> SEQ ID NO 23
<211> LENGTH: 18
<212> TYPE: DNA
<213> ORGANISM: Homo sapiens

<400> SEQUENCE: 23
cggtgtgact cgtgcagc                                                 18

<210> SEQ ID NO 24
<211> LENGTH: 20
<212> TYPE: DNA
<213> ORGANISM: Homo sapiens

<400> SEQUENCE: 24
acagccgctt cacctacagc                                               20

<210> SEQ ID NO 25
<211> LENGTH: 19
<212> TYPE: DNA
<213> ORGANISM: Homo sapiens

<400> SEQUENCE: 25
tcaaactggc tgccagcat                                                19

<210> SEQ ID NO 26
<211> LENGTH: 21
<212> TYPE: DNA
<213> ORGANISM: Homo sapiens

<400> SEQUENCE: 26
caagaaacac gtctggctag g                                             21

<210> SEQ ID NO 27
<211> LENGTH: 24
<212> TYPE: DNA
<213> ORGANISM: Homo sapiens

<400> SEQUENCE: 27
cgctaaggcg aaagccctca attt                                          24

<210> SEQ ID NO 28
<211> LENGTH: 24
<212> TYPE: DNA
<213> ORGANISM: Homo sapiens

<400> SEQUENCE: 28
acaattcctg gcgataccte agca                                          24
```

```
<210> SEQ ID NO 29
<211> LENGTH: 24
<212> TYPE: DNA
<213> ORGANISM: Homo sapiens

<400> SEQUENCE: 29
tctgcaattc cgacctcgtc atca                                              24

<210> SEQ ID NO 30
<211> LENGTH: 24
<212> TYPE: DNA
<213> ORGANISM: Homo sapiens

<400> SEQUENCE: 30
aaggtggtct ggttgacttc tggt                                              24

<210> SEQ ID NO 31
<211> LENGTH: 20
<212> TYPE: DNA
<213> ORGANISM: Homo sapiens

<400> SEQUENCE: 31
cattcccagc tcccctctct                                                   20

<210> SEQ ID NO 32
<211> LENGTH: 20
<212> TYPE: DNA
<213> ORGANISM: Homo sapiens

<400> SEQUENCE: 32
agtctacgtg gcaggcaagg                                                   20

<210> SEQ ID NO 33
<211> LENGTH: 21
<212> TYPE: DNA
<213> ORGANISM: Homo sapiens

<400> SEQUENCE: 33
cctgagccag taaccacctc c                                                 21

<210> SEQ ID NO 34
<211> LENGTH: 21
<212> TYPE: DNA
<213> ORGANISM: Homo sapiens

<400> SEQUENCE: 34
ctttcgaagc taacgtggca g                                                 21
```